(12) United States Patent
Jain et al.

(10) Patent No.: US 9,018,249 B2
(45) Date of Patent: Apr. 28, 2015

(54) SGLT INHIBITORS

(75) Inventors: Rajesh Jain, New Delhi (IN); Sanjay Trehan, New Delhi (IN); Jagattaran Das, New Delhi (IN); Gurmeet Kaur Nanda, New Delhi (IN); Sastry V. R. S. Thungathurthi, New Delhi (IN); Nishan Singh, New Delhi (IN); Sudhir Kumar Sharma, New Delhi (IN)

(73) Assignee: Panacea Biotec Limited, New Delhi (IN)

( * ) Notice: Subject to any disclaimer, the term of this patent is extended or adjusted under 35 U.S.C. 154(b) by 0 days.

(21) Appl. No.: 14/344,628

(22) PCT Filed: Sep. 12, 2012

(86) PCT No.: PCT/IN2012/000612
§ 371 (c)(1),
(2), (4) Date: May 23, 2014

(87) PCT Pub. No.: WO2013/038429
PCT Pub. Date: Mar. 21, 2013

(65) Prior Publication Data
US 2014/0378540 A1   Dec. 25, 2014

(30) Foreign Application Priority Data

Sep. 13, 2011 (IN) .............................. 1677/DEL/2011
Jun. 4, 2012 (IN) .............................. 1709/DEL/2012

(51) Int. Cl.
*A61K 31/352* (2006.01)
*C07D 311/00* (2006.01)
*C07D 309/10* (2006.01)
*C07D 493/08* (2006.01)

(52) U.S. Cl.
CPC ............ *C07D 309/10* (2013.01); *C07D 493/08* (2013.01)

(58) Field of Classification Search
CPC ................................................ C07D 309/10
USPC ........................................ 514/456; 549/397
See application file for complete search history.

(56) References Cited

U.S. PATENT DOCUMENTS 6,774,112 B2    8/2004  Gougoutas

FOREIGN PATENT DOCUMENTS

| WO | 2010016554 A1 | 2/2010 |
|---|---|---|
| WO | 2010023594 A1 | 3/2010 |
| WO | 2010084512 A1 | 7/2010 |
| WO | 2011070592 A2 | 6/2011 |

OTHER PUBLICATIONS

Kinne, RKH et al., SGLT Inhibitors as New Therapeutic Tools in the Treatment of Diabetes, in Diabetes—Perspectives in Drug Therapy, Handbook of Experimental Pharmacology 203, M. Schwanstecher (Editor), Springer-Verlag Berlin Heidelberg, Mar. 14, 2011, pp. 105-126.

International Search Report for PCT/IN2012/000612 dated Sep. 30, 2013.

*Primary Examiner* — Taofiq A Solola
(74) *Attorney, Agent, or Firm* — Lowe Hauptman & Ham, LLP

(57) ABSTRACT

The present invention relates to novel compounds of Formula I, their pharmaceutically acceptable derivatives, tautomeric forms, isomers, polymorphs, prodrugs, metabolites, salts or solvates thereof. The invention also relates to the processes for the synthesis of novel compounds of Formula I, their pharmaceutically acceptable derivatives, tautomeric forms, isomers, polymorphs, prodrugs, metabolites, salts or solvates thereof. The present invention also provides pharmaceutical compositions comprising novel compounds of Formula I and methods of treating or preventing one or more conditions or diseases that may be regulated or normalized via inhibition of Sodium Glucose Cotransporter-2 (SGLT-2).

Formula I

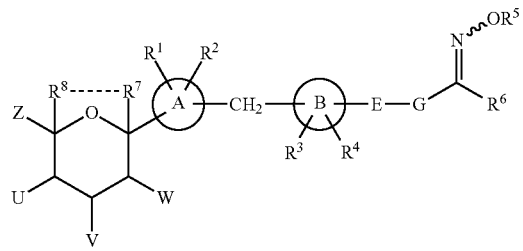

12 Claims, No Drawings

SGLT INHIBITORS

RELATED APPLICATIONS

The present application claims priority from, Indian Application Number 1677/DEL/2011 and 1709/DEL/2012.

FIELD OF THE INVENTION

The present invention relates to novel compounds of Formula I, their pharmaceutically acceptable derivatives, tautomeric forms, isomers, polymorphs, prodrugs, metabolites, salts or solvates thereof. The invention also relates to the processes for the synthesis of novel compounds of Formula I, their pharmaceutically acceptable derivatives, tautomeric forms, isomers, polymorphs, prodrugs, metabolites, salts or solvates thereof. The present invention also provides pharmaceutical compositions comprising novel compounds of Formula I and methods of treating or preventing one or more conditions or diseases that may be regulated or normalized via inhibition of Sodium Glucose Cotransporter-2 (SGLT-2).

BACKGROUND OF THE INVENTION

Diabetes is a metabolic disorder which is rapidly emerging as a global health care problem that threatens to reach pandemic levels. The number of people with diabetes worldwide is expected to rise from 285 million in 2010 to 438 million by 2030. Diabetes results from deficiency in insulin because of impaired pancreatic β-cell function or from resistance to insulin in body, thus leading to abnormally high levels of blood glucose.

Diabetes which results from complete deficiency in insulin secretion is Type 1 diabetes and the diabetes due to resistance to insulin activity together with an inadequate insulin secretion is Type 2 diabetes. Type 2 diabetes (Non insulin dependent diabetes) accounts for 90-95% of all diabetes. An early defect in Type 2 diabetes mellitus is insulin resistance which is a state of reduced responsiveness to circulating concentrations of insulin and is often present years before clinical diagnosis of diabetes. A key component of the pathophysiology of Type 2 diabetes mellitus involves an impaired pancreatic β-cell function which eventually contributes to decreased insulin secretion in response to elevated plasma glucose. The β-cell compensates for insulin resistance by increasing the insulin secretion, eventually resulting in reduced β-cell mass. Consequently, blood glucose levels stay at abnormally high levels (hyperglycemia).

Hyperglycemia is central to both the vascular consequences of diabetes and the progressive nature of the disease itself. Chronic hyperglycemia leads to decrease in insulin secretion and further to decrease in insulin sensitivity. As a result, the blood glucose concentration is increased, leading to diabetes, which is self-exacerbated. Chronic hyperglycemia has been shown to result in higher protein glycation, cell apoptosis and increased oxidative stress; leading to complications such as cardiovascular disease, stroke, nephropathy, retinopathy (leading to visual impairment or blindness), neuropathy, hypertension, dyslipidemia, premature atherosclerosis, diabetic foot ulcer and obesity. So, when a person suffers from diabetes, it becomes important to control the blood glucose level. Normalization of plasma glucose in Type 2 diabetes patients improves insulin action and may offset the development of beta cell failure and diabetic complications in the advanced stages of the disease.

Diabetes is basically treated by diet and exercise therapies. However, when sufficient relief is not obtained by these therapies, medicament is prescribed alongwith. Various anti-diabetic agents being currently used include biguanides (decrease glucose production in the liver and increase sensitivity to insulin), sulfonylureas and meglitinides (stimulate insulin production), α-glucosidase inhibitors (slow down starch absorption and glucose production) and thiazolidinediones (increase insulin sensitivity). These therapies have various side effects: biguanides cause lactic acidosis, sulfonylurea compounds cause significant hypoglycemia, α-glucosidase inhibitors cause abdominal bloating and diarrhea, and thiazolidinediones cause edema and weight gain. Recently introduced line of therapy includes inhibitors of dipeptidyl peptidase-IV (DPP-IV) enzyme, which may be useful in the treatment of diabetes, particularly in Type 2 diabetes. DPP-IV inhibitors lead to decrease in inactivation of incretins glucagon like peptide-1 (GLP-1) and gastric inhibitory peptide (GIP), thus leading to increased production of insulin by the pancreas in a glucose dependent manner. All of these therapies discussed, have an insulin dependent mechanism.

Another mechanism which offers insulin independent means of reducing glycemic levels, is the inhibition of sodium glucose co-transporters (SGLTs). In healthy individuals, almost 99% of the plasma glucose filtered in the kidneys is reabsorbed, thus leading to only less than 1% of the total filtered glucose being excreted in urine. Two types of SGLTs, SGLT-1 and SGLT-2, enable the kidneys to recover filtered glucose. SGLT-1 is a low capacity, high-affinity transporter expressed in the gut (small intestine epithelium), heart, and kidney (S3 segment of the renal proximal tubule), whereas SGLT-2 (a 672 amino acid protein containing 14 membrane-spanning segments), is a low affinity, high capacity glucose transporter, located mainly in the S1 segment of the proximal tubule of the kidney. SGLT-2 facilitates approximately 90% of glucose reabsorption and the rate of glucose filtration increases proportionally as the glycemic level increases. The inhibition of SGLT-2 should be highly selective, because non-selective inhibition leads to complications such as severe, sometimes fatal diarrhea, dehydration, peripheral insulin resistance, hypoglycemia in CNS and an impaired glucose uptake in the intestine.

Humans lacking a functional SGLT-2 gene appear to live normal lives, other than exhibiting copious glucose excretion with no adverse effects on carbohydrate metabolism. However, humans with SGLT-1 gene mutations are unable to transport glucose or galactose normally across the intestinal wall, resulting in condition known as glucose-galactose malabsorption syndrome.

Hence, competitive inhibition of SGLT-2, leading to renal excretion of glucose represents an attractive approach to normalize the high blood glucose associated with diabetes. Lower blood glucose levels would, in turn, lead to reduced rates of protein glycation, improved insulin sensitivity in liver and peripheral tissues, and improved cell function. As a consequence of progressive reduction in hepatic insulin resistance, the elevated hepatic glucose output which is characteristic of Type 2 diabetes would be expected to gradually diminish to normal values. In addition, excretion of glucose may reduce overall caloric load and lead to weight loss. Risk of hypoglycemia associated with SGLT-2 inhibition mechanism is low, because there is no interference with the normal counter regulatory mechanisms for glucose.

The first known non-selective SGLT-2 inhibitor was the natural product phlorizin (glucose, 1-[2-β-D-glucopyranosyloxy)-4,6-dihydroxyphenyl]-3-(4-hydroxyphenyl)-1-propanone). Subsequently, several other synthetic analogues were derived based on the structure of phlorizin. Optimisation of the scaffolds to achieve selective SGLT-2 inhibitors led to the discovery of several considerably different scaffolds.

C-glycoside derivatives have been disclosed, for example, in PCT publications WO2004013118, WO2005085265, WO2006008038, WO2006034489, WO2006037537, WO2006010557, WO2006089872, WO2006002912, WO2006054629, WO2006064033, WO2007136116, WO2007000445, WO2007093610, WO2008069327, WO2008020011, WO2008013321, WO2008013277, WO2008042688, WO2008122014, WO2008116195, WO2008042688, WO2009026537, WO2010147430, WO2010095768, WO2010023594, WO2010022313, WO2011051864, WO2011048148 and WO2012019496 U.S. patents U.S. Pat. Nos. 6,515,117B2, 6,936,590B2 and 7,202,350B2 and Japanese patent application JP2004359630.

The compounds shown below are the SGLT-2 inhibitors which have reached advanced stages of human clinical trials: Bristol-Myers Squibb's "Dapagliflozin" with Formula A, Mitsubishi Tanabe and Johnson & Johnson's "Canagliflozin" with Formula B, Lexicon's "Lx-4211" with Formula C, Boehringer Ingelheim and Eli Lilly's "Empagliflozin" with Formula D, Roche and Chugai's "Tofogliflozin" with Formula E, Taisho's "Luseogliflozin" with Formula F, Pfizer's "Ertugliflozin" with Formula G and Astellas and Kotobuki's "Ipragliflozin" with Formula H.

Formula A

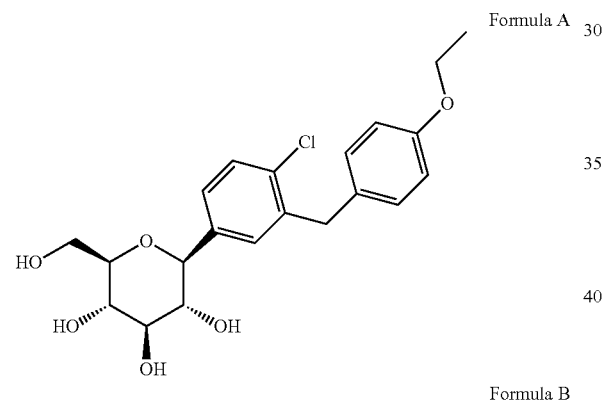

Formula B

Formula C

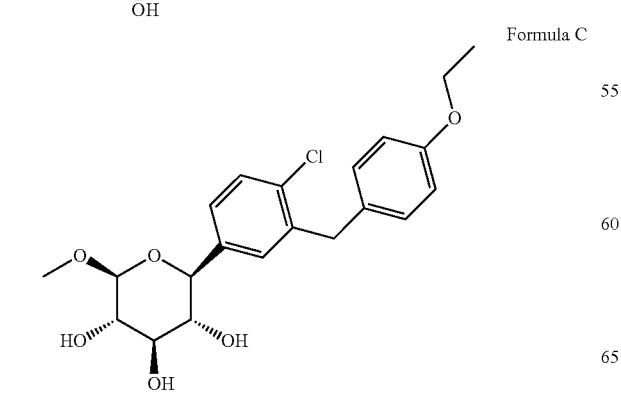

Formula D

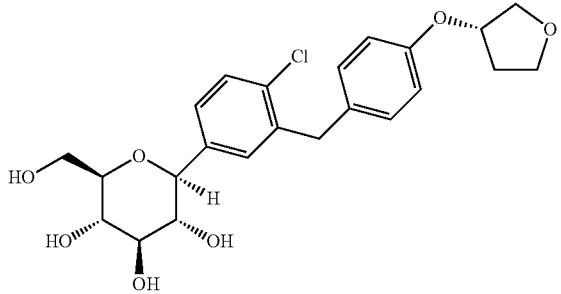

Formula E

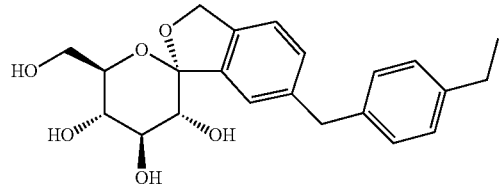

Formula F

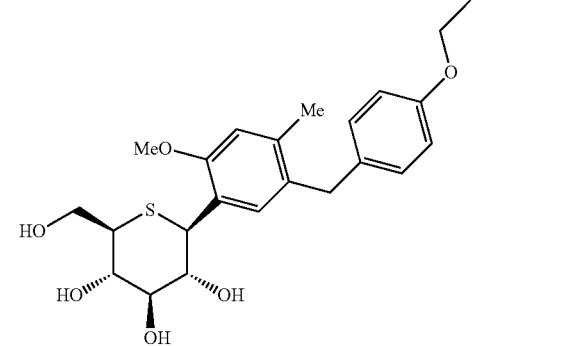

Formula G

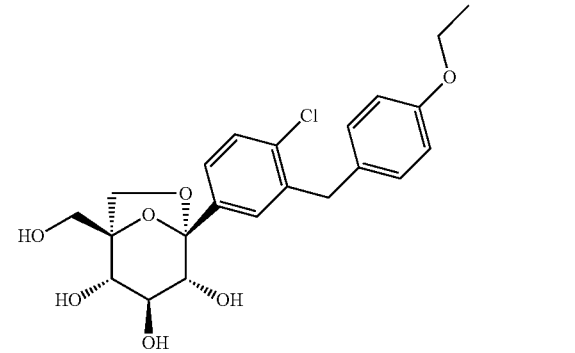

Formula H

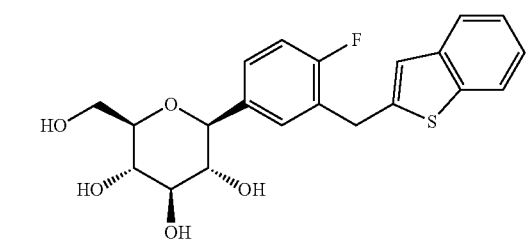

In spite of all these molecules in advanced stages of human clinical trials, there is still no drug available in the market as SGLT-2 inhibitor. Out of the potential candidates entering the clinical stages, many have been discontinued, emphasizing the unmet need. Thus there is an ongoing requirement to screen more scaffolds useful as SGLT-2 inhibitors that can have advantageous potency, stability, selectivity, better half-life, and/or better pharmacodynamic properties. In this regard, a novel class of SGLT-2 inhibitors is provided herein.

SUMMARY OF THE INVENTION

The present invention is defined in the claims and relates to the novel compounds of Formula I,

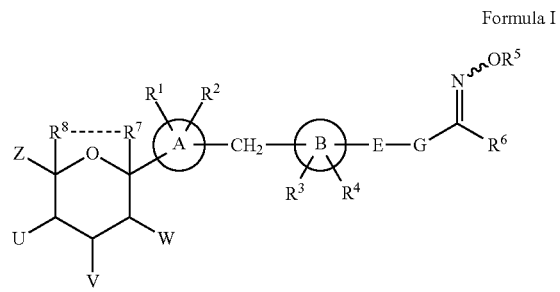

Formula I wherein:
'—' is either a single bond or absent;
ring A represents monocyclic or polycyclic $C_{3-20}$ cycloalkyl, $C_{6-10}$ aryl, 5-10 membered heteroaryl or 3-14 membered heterocyclyl ring;
ring B represents monocyclic or polycyclic $C_{3-20}$ cycloalkyl, $C_{6-10}$ aryl, 5-10 membered heteroaryl or 3-14 membered heterocyclyl ring;
U, V and W are independently selected from —H, $C_{1-12}$ alkyl, $C_{2-12}$ alkenyl, $C_{2-12}$ alkynyl, —OH, —CN, —$N_3$, —$NO_2$, —$OCONH_2$, —F, —Cl, —Br, —I, —COOH, —$CONH_2$, —$CONHNH_2$, —$NH_2$, —$NHCONH_2$, —$NHCSNH_2$, —NH(C=NH)$NH_2$, —$NHNH_2$, —NHCHO, —NHCOOH, —SH, —$SO_3H$, —CH(=NOH), —$COR^a$, —$OR^9$, —$COOR^a$, —$CONR^aR^b$, —$NR^aR^b$, —$NR^aSO_2R^b$, —$NR^aCONR^bR^c$, —$NR^aCOR^b$, —$NR^a$-$COOR^b$, —$OCOR^a$, —$OCOOR^a$, —$OCONR^aR^b$, —$SR^a$, —$S(O)R^a$, —$S(O)_2R^a$, —$SO_2NR^aR^b$, —$CR^a$(=$NOR^b$), —$NHP(O)R^aR^b$; wherein the said $C_{1-12}$ alkyl, $C_{2-12}$ alkenyl and $C_{2-12}$ alkynyl, may optionally be substituted at any available position by one or more suitable substituents selected from $R^{11}$;
provided that at least two out of U, V and W represent —$OR^9$;
Z represents —$(CH_2)_nOR^a$, —$OR^a$, —$OCOR^a$, —$OCOOR^a$, —$OCONR^aR^b$, $C_{1-12}$ alkyl, $C_{2-12}$ alkenyl, $C_{2-12}$ alkynyl, —CN, —$OCONH_2$, —CHO, —COOH, —$CONH_2$, —$CONHNH_2$, —$NH_2$, —NHCOOH, —$CH_2OH$, —OH, —SH, —$SO_3H$, —CH(=NOH), —CH(=NCN), —$COR^a$, —$COOR^a$, —$CONR^aR^b$, —$NR^aR^b$, —$NR^aSO_2R^b$, —$NR^aCONR^bR^c$, —$NR^aNR^bR^c$, —$NR^aCOR^b$, —$NR^aCOOR^b$, —$SR^a$, —$S(O)R^a$, —$S(O)_2R^a$, —$SO_2NR^aR^b$ or —$CR^a$(=$NOR^b$); wherein the said $C_{1-12}$ alkyl, $C_{2-12}$ alkenyl and $C_{2-12}$ alkynyl, may optionally be substituted at any available position by one or more suitable substituents selected from $R^{11}$;
$R^1$, $R^2$, $R^3$ and $R^4$ are independently selected from —H, $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —$N_3$, —$NO_2$, —$OCONH_2$, —F, —Cl, —Br, —I, —CHO, —COOH, —$CONH_2$, —$NH_2$, —$NHCONH_2$, —NHCHO, —NHCOOH, —OH, —$OR^a$, —SH, —$SO_3H$; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $R^{11}$;
$R^5$ represents —H, $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl or 5-10 membered heteroaryl; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $R^{11}$;
$R^6$ represents —H, $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —$NH_2$, —$NHCONH_2$, —NHCHO, —OH, —SH, —$NR^aR^b$, —$NR^aCONR^bR^c$, —$NR^aCOR^b$, —$OR^a$ or —$SR^a$; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $R^{11}$;
E represents O, S, SO, $SO_2$, $NR^{10}$ or a single bond;
G represents $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl or 5-10 membered heteroaryl; each of which may optionally be substituted at any available position by one or more suitable substituents selected from $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —$N_3$, —$NO_2$, —OCN, —NCO, —SCN, —NCS, —$OCONH_2$, —$ONO_2$, —F, —Cl, —Br, —I, —CO—, —CS—, —CHO, —CHS, —COOH, —COSH, —$CONH_2$, —$CONHNH_2$, —$CSNHNH_2$, —$CSNH_2$, —$NH_2$, —$NHCONH_2$, —$NHCSNH_2$, —NH(C=NH)$NH_2$, —$NHNH_2$, —NHCHO, —NHCHS, —NHCOOH, —NHCSOH, —OH, —SH, —$SO_3H$, —CH(=NOH), —CH(=NCN), —$COR^a$, —$COOR^a$, —$CSOR^a$, —$COSR^a$, —$CONR^aR^b$, —$CSNR^aR^b$, —$COCOR^a$, $CONR^aNR^bR^c$, $CSNR^aNR^bR^c$, —$CSNR^bR^c$, —$NR^aR^b$, —$NR^aSO_2R^b$, —$NR^aCONR^bR^c$, —$NR^aCSNR^bR^c$, —$NR^a(C=NR^b)NR^cR^d$, —$NR^aNR^bR^c$, —$NR^aCOR^b$, —$NR^aCSR^b$, —$NR^aCOOR^b$, —$NR^aCSOR^b$, —$OR^a$, —$OCOR^a$, —$OCOOR^a$, —$OCONR^aR^b$, —$OCSR^a$, —$OCSOR^a$, —$ONO_2$, —$OCSNR^aR^b$, —$SR^a$, —$S(O)R^a$, —$S(O)_2R^a$, —$SO_2NR^aR^b$, —$CR^a$(=$NOR^b$), —$CR^a$(=$NCOOR^b$), —$CR^a$(=$NSOR^b$), —$CR^a$(=$NSO_2R^b$), —C(=$NR^a$)—$NR^bR^c$, —C(=$NOR^a$)—$NR^bR^c$, —$CR^a$(=NCN), —$NCR^a$, —$P(O)R^aR^b$, —$P(O)OR^aOR^b$, —$P(O)R^aOR^6$, —$P(O)NR^aOR^b$, —$P(O)NR^aR^b$, —$OP(O)R^aR^b$, —$NHP(O)R^aR^b$; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —$N_3$, —$NO_2$, —OCN, —NCO, —SCN, —NCS, —$OCONH_2$, —$ONO_2$, —F, —Cl, —Br, —I, —CO—, —CS—, —CHO, —CHS, —COOH, —COSH, —$CONH_2$, —$CONHNH_2$, —$CSNHNH_2$, —$CSNH_2$, —$NH_2$, —$NHCONH_2$, —$NHCSNH_2$, —NH(C=NH)$NH_2$, —$NHNH_2$, —NHCHO, —NHCHS, —NHCOOH, —NHCSOH, —OH, —SH, —$SO_3H$, —CH(=NOH), —CH(=NCN);
When E is a single bond or Nitrogen, then E and $R^6$ can be joined together to form a saturated or unsaturated $C_{3-10}$ cycloalkyl or 3-10 membered heterocyclyl ring, which may further be fused to one or more $C_{3-10}$ cycloalkyl, 3-10 membered heterocyclyl, $C_{5-10}$ aryl or 5-10 membered heteroaryl ring. The ring thus formed may further be substituted with substituents selected from $R^{12}$;

G and $R^6$ can be joined together to form a saturated or unsaturated $C_{3-10}$ cycloalkyl or 3-10 membered heterocyclyl ring, which may further be fused to one or more $C_{3-10}$ cycloalkyl, 3-10 membered heterocyclyl, $C_{5-10}$ aryl or 5-10 membered heteroaryl ring. The ring thus formed may further be substituted with substituents selected from $R^{12}$;

$R^7$ represents —H, —OH or —OR$^9$;

$R^8$ represents —H, —CHO, —COOH, —CONH$_2$, —OH, —CH(=NOH), —COR$^a$, —COOR$^a$, —CONR$^a$R$^b$, —CR$^a$(NOR$^b$), —OR$^a$, or —(CH$_2$)$_n$OR$^a$;

or $R^7$ and $R^8$ can be joined together to form a saturated or unsaturated ring, in which one or more methylene groups or methyne groups can be replaced with O, S, NR$^a$ or oxo; the ring thus formed may optionally be substituted at any available position by one or more suitable substituents selected from $R^{12}$;

or $R^8$ and Z can be joined together to form a saturated or unsaturated ring, in which one or more methylene groups or methyne groups can be replaced with O, S, NR$^a$ or oxo; the ring thus formed may optionally be substituted at any available position by one or more suitable substituents selected from $R^{12}$;

$R^9$ represents —H, $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CHO, —CONH$_2$, —COR$^a$, —CONR$^a$R$^b$, —S(O)$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$ or —P(O)NR$^a$R$^b$; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CHO, —CONH$_2$, —COR$^a$, —CONR$^a$R$^b$, —S(O)$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$; further wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $R^{13}$;

$R^{10}$ represents —H, $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CR$^a$(=NOR$^b$), —S(O)R$^a$, —S(O)$_2$R$^a$, —S(O)$_2$NR$^a$R$^b$, —(CH$_2$)$_n$S(O)R$^a$, —(CH$_2$)$_n$S(O)$_2$R$^a$, —P(O)R$^a$R$^b$, —COR$^a$, —CSR$^a$, —COOR$^a$, —CSOR$^a$, —COSR$^a$, —CSSR$^a$, —CONR$^a$R$^b$ or —CSNR$^a$R$^b$; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —NO$_2$, NH$_2$; further wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $R^{13}$;

$R^{11}$ represents $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —NH(C=NH)NH$_2$, —NHNH$_2$, —NHCHO, —NHCHS, —NHCOOH, —NHCSOH, —OH, —SH, —SO$_3$H, —CH(=NOH), —CH(=NCN), —COR$^a$, —CSR$^a$, —COOR$^a$, —CSOR$^a$, —COSR$^a$, —CONR$^a$R$^b$, —CSNR$^a$R$^b$, —COCOR$^a$, —CONR$^a$NR$^b$R$^c$, —CSNR$^a$NR$^b$R$^c$, —CSNR$^a$R$^b$, —NR$^a$R$^b$, —NR$^a$SO$_2$R$^b$, —NR$^a$CONR$^b$R$^c$, —NR$^a$CSNR$^b$R$^c$, —NR$^a$(C=NR$^b$)NR$^c$R$^d$, —NR$^a$NR$^b$R$^c$, —NR$^a$COR$^b$, —NR$^a$CSR$^b$, —NR$^a$COOR$^b$, —NR$^a$CSOR$^b$, —OR$^a$, —OCOR$^a$, —OCOOR$^a$, —OCONR$^a$R$^b$, —OCSR$^a$, —OCSOR$^a$, —ONO$_2$, —OCSNR$^a$R$^b$, —SR$^a$, —S(O)R$^a$, —S(O)$_2$R$^a$, —SO$_2$NR$^a$R$^b$, —CR$^a$(=NOR$^b$), —CR$^a$(=NCOOR$^b$), —CR$^a$(=NSOR$^b$), —CR$^a$(=NSO$_2$R$^b$), —C(=NR$^a$)—NR$^b$R$^c$, —C(=NOR$^a$)—NR$^b$R$^c$, —CR$^a$(=NCN), —NCR$^a$, —P(O)R$^a$R$^b$, —P(O)OR$^a$OR$^b$, —P(O)R$^a$OR$^b$, —P(O)NR$^a$OR$^b$, —P(O)NR$^a$R$^b$, —OP(O)R$^a$R$^b$ or —NHP(O)R$^a$R$^b$; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $R^{13}$;

$R^{12}$ represents $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —NH(C=NH)NH$_2$, —NHNH$_2$, —NHCHO, —NHCHS, —NHCOOH, —NHCSOH, —OH, —SH, —SO$_3$H, —CH(=NOH) or —CH(=NCN); wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $R^{13}$;

$R^{13}$ represents $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —NH(C=NH)NH$_2$, —NHNH$_2$, NHCHO, —NHCHS, —NHCOOH, —NHCSOH, —OH, —SH, —SO$_3$H, —CH(=NOH) or —CH(=NCN);

$R^a$, $R^b$, $R^c$ and $R^d$ are independently selected from —H, $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —NH(C=NH)NH$_2$, —NHNH$_2$, —NHCHO, —NHCHS, —NHCOOH, —NHCSOH, —OH, —SH, —SO$_3$H, —CH(=NOH), —CH(=NCN); each of which may optionally be substituted at any available position by one or more suitable substituents selected from $R^{13}$;

or

R$^a$ and R$^b$ when attached to the same atom, can be joined together to form a monocyclic or polycyclic ring, in which one or more methylene groups or methyne groups can be replaced with O, S, SO, SO$_2$, NR$^a$, PR$^a$, P(=O)R$^a$ or oxo; the ring thus formed may optionally be substituted at any available position by one or more suitable substituents selected from R$^{12}$;

or

R$^b$ and R$^c$ when attached to the same atom, can be joined together to form a monocyclic or polycyclic ring, in which one or more methylene groups or methyne groups can be replaced with O, S, SO, SO$_2$, NR$^a$, PR$^a$, P(=O)R$^a$ or oxo; the ring thus formed may optionally be substituted at any available position by one or more suitable substituents selected from R$^{12}$;

or

R$^c$ and R$^d$ when attached to the same atom, can be joined together to form a monocyclic or polycyclic ring, in which one or more methylene groups or methyne groups can be replaced with O, S, SO, SO$_2$, NRa, PR$^a$, P(=O)R$^a$ or oxo; the ring thus formed may optionally be substituted at any available position by one or more suitable substituents selected from R$^{12}$;

n represents 1, 2, 3, 4 or 5; their pharmaceutically acceptable derivatives, tautomeric forms, isomers, polymorphs, prodrugs, metabolites, salts or solvates thereof.

A further aspect of the present invention provides processes for the preparation of the novel compounds of Formula I, their pharmaceutically acceptable derivatives, tautomeric forms, isomers, polymorphs, prodrugs, metabolites, salts or solvates thereof.

Another aspect of the present invention provides pharmaceutical compositions, containing compounds of Formula I, their pharmaceutically acceptable derivatives, tautomeric forms, isomers, polymorphs, prodrugs, metabolites, salts or solvates thereof in combination with one or more pharmaceutically acceptable carrier(s), adjuvants and vehicles.

Another aspect of the present invention is the use of the compounds of Formula I, their pharmaceutically acceptable derivatives, tautomeric forms, isomers, polymorphs, prodrugs, metabolites, salts or solvates thereof, for the prophylaxis, amelioration and/or treatment of one or more condition (s)/disease(s)/disorder(s), in a subject in need thereof.

Still another aspect of the present invention is the use of the compounds of Formula I, their pharmaceutically acceptable derivatives, tautomeric forms, isomers, polymorphs, prodrugs, metabolites, salts or solvates thereof, for the prophylaxis, amelioration and/or treatment of one or more condition (s)/disease(s)/disorder(s) that may be regulated or normalized via inhibition of SGLT-2.

Yet another aspect of the invention is to provide methods of using the compounds of Formula I of the present invention or compositions comprising the compounds of Formula I for the prophylaxis, amelioration and/or treatment of disease(s)/disorder(s) involving SGLT-2 inhibition which comprises administering to a subject in need thereof the compounds of Formula I or compositions comprising a pharmaceutically effective amount of the compounds of Formula I.

A further aspect of the present invention is the use of a compound of Formula I for the manufacture of a medicament for the prophylaxis, amelioration and/or treatment of one or more condition(s)/disease(s)/disorder(s) involving SGLT-2 inhibition in a subject in need thereof.

The present invention also encompasses prodrugs and active metabolites of the compounds of the Formula I.

Other aspects of the invention will be set forth in the description which follows, and in part will be apparent from the description, or may be learnt by the practice of the invention.

DETAILED DESCRIPTION OF THE INVENTION

The present invention relates to the novel compounds of Formula I,

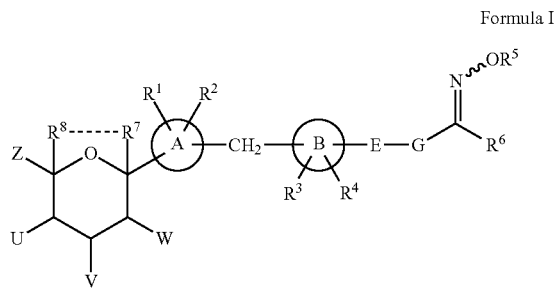

Formula I wherein:

'—' is either a single bond or absent;

ring A represents monocyclic or polycyclic C$_{3-20}$ cycloalkyl, C$_{6-10}$ aryl, 5-10 membered heteroaryl or 3-14 membered heterocyclyl ring;

ring B represents monocyclic or polycyclic C$_{3-20}$ cycloalkyl, C$_{6-10}$ aryl, 5-10 membered heteroaryl or 3-14 membered heterocyclyl ring;

U, V and W are independently selected from —H, C$_{1-12}$ alkyl, C$_{2-12}$ alkenyl, C$_{2-12}$ alkynyl, —OH, —CN, —N$_3$, —NO$_2$, —OCONH$_2$, —F, —Cl, —Br, —I, —COOH, —CONH$_2$, —CONHNH$_2$, —NH$_2$, —NHCONH$_2$, —NHCSNH$_2$, —NH(C=NH)NH$_2$, —NHNH$_2$, —NHCHO, —NH-COOH, —SH, —SO$_3$H, —CH(=NOH), —COR$^a$, —OR$^9$, —COOR$^a$, —CONR$^a$R$^b$, —NR$^a$R$^b$, —NR$^a$SO$_2$R$^b$, —NR$^a$CONR$^b$R$^c$, —NR$^a$COR$^b$, —NR$^a$COOR$^b$, —OCOR$^a$, —OCOOR$^a$, —OCONR$^a$R$^b$, —SR$^a$, —S(O)R$^a$, —S(O)$_2$R$^a$, —SO$_2$NR$^a$R$^b$, —CR$^a$(=NOR), —NHP(O)R$^a$R$^b$; wherein the said C$_{1-12}$ alkyl, C$_{2-12}$ alkenyl and C$_{2-12}$ alkynyl, may optionally be substituted at any available position by one or more suitable substituents selected from R$^{11}$;

provided that at least two out of U, V and W represent —OR$^9$;

Z represents —(CH$_2$)$_n$OR$^a$, —OR$^a$, —OCOR$^a$, —OCOOR$^a$, —OCONR$^a$R$^b$, C$_{1-12}$ alkyl, C$_{2-12}$ alkenyl, C$_{2-12}$ alkynyl, —CN, —OCONH$_2$, —CHO, —COOH, —CONH$_2$, —CONHNH$_2$, —NH$_2$, —NHCOOH, —CH/OH, —OH, —SH, —SO$_3$H, —CH(=NOH), —CH(=NCN), —COR$^a$, —COOR$^a$, —CONR$^a$R$^b$, —NR$^a$R$^b$, —NR$^a$SO$_2$R$^b$, —NR$^a$CONR$^b$R$^c$, —NR$^a$NR$^b$R$^c$, —NR$^a$COR$^b$, —NR$^a$COOR$^b$, —SR$^a$, —S(O)R$^a$, —S(O)$_2$R$^a$, —SO$_2$NR$^a$R$^b$ or —CR$^a$(=NOR$^b$); wherein the said C$_{1-12}$ alkyl, C$_{2-12}$ alkenyl and C$_{2-12}$ alkynyl, may optionally be substituted at any available position by one or more suitable substituents selected from R$^{11}$;

R$^1$, R$^2$, R$^3$ and R$^4$ are independently selected from —H, C$_{1-12}$ alkyl, C$_{2-12}$ alkenyl, C$_{2-12}$ alkynyl, C$_{6-10}$ aryl, C$_{3-20}$ cycloalkyl, 3-14 membered heterocyclyl, 5-10 membered heteroaryl, —CN, —COCN, —N$_3$, —NO$_2$, —OCONH$_2$, —F, —Cl, —Br, —I, —CHO, —COOH, —CONH$_2$, —NH$_2$, —NHCONH$_2$, —NHCHO, —NHCOOH, —OH, —OR$^a$, —SH, —SO$_3$H; wherein the said C$_{1-12}$ alkyl, C$_{2-12}$ alkenyl, C$_{2-12}$ alkynyl, C$_{6-10}$ aryl, C$_{3-20}$ cycloalkyl, 3-14 membered heterocyclyl and 5-10 membered heteroaryl, may optionally be substituted at any available position by one or more suitable substituents selected from $R^{11}$;

$R^5$ represents —H, $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl or 5-10 membered heteroaryl; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $R^{11}$;

$R^6$ represents —H, $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —NH$_2$, —NHCONH$_2$, —NHCHO, —OH, —SH, —NR$^a$R$^b$, —NR$^a$CONR$^b$R$^c$, —NR$^a$COR$^b$, —OR$^a$ or —SR$^a$; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $R^{11}$;

E represents O, S, SO, SO$_2$, NR$^{10}$ or a single bond;

G represents $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl or 5-10 membered heteroaryl; each of which may optionally be substituted at any available position by one or more suitable substituents selected from $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —NH(C=NH)NH$_2$, —NHNH$_2$, —NHCHO, —NHCHS, —NHCOOH, —NHCSOH, —OH, —SH, —SO$_3$H, —CH(=NOH), —CH(=NCN), —COR$^a$, —COOR$^a$, —CSOR$^a$, —COSR$^a$, —CONR$^a$R$^b$, —CSNR$^a$R$^b$, —COCOR$^a$, —CONR$^a$NR$^b$R$^c$, —CSNR$^a$NR$^b$R$^c$, —CSNR$^a$R$^b$, —NR$^a$R$^b$, —NR$^a$SO$_2$R$^b$, —NR$^a$CONR$^b$R$^c$, —NR$^a$CSNR$^b$R$^c$, —NR$^a$(C=NR$^b$)NR$^c$R$^d$, —NR$^a$NR$^b$R$^c$, —NR$^a$COR$^b$, —NR$^a$COR$^b$, —NR$^a$COOR$^b$, —NR$^a$CSOR$^b$, —OR$^a$, —OCOR$^a$, —OCOOR$^a$, —OCONR$^a$R$^b$, —OCSR$^a$, —OCSOR$^a$, —ONO$_2$, —OCSNR$^a$R$^b$, —SR$^a$, —S(O)R$^a$, —S(O)$_2$R$^a$, —SO$_2$NR$^a$R$^b$, —CR$^a$(=NOR$^b$), —CR$^a$(=NCOOR$^b$), —CR$^a$(=NSOR$^b$), —CR$^a$(=NSO$_2$R$^b$), —C(=NR$^a$)—NR$^b$R$^c$, —C(=NOR$^a$)—NR$^b$R$^c$, —CR$^a$(=NCN), —NCR$^a$, —P(O)R$^a$R$^b$, —P(O)OR$^a$OR$^b$, —P(O)R$^a$OR$^b$, —P(O)NR$^a$OR$^b$, —P(O)NR$^a$R$^b$, —OP(O)R$^a$R$^b$, —NHP(O)R$^a$R$^b$; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —NH(C=NH)NH$_2$, —NHNH$_2$, —NHCHO, —NHCHS, —NHCOOH, —NHCSOH, —OH, —SH, —SO$_3$H, —CH(=NOH), —CH(=NCN);

When E is a single bond or Nitrogen, then E and $R^6$ can be joined together to form a saturated or unsaturated $C_{3-10}$ cycloalkyl or 3-10 membered heterocyclyl ring, which may further be fused to one or more $C_{3-10}$ cycloalkyl, 3-10 membered heterocyclyl, $C_{5-10}$ aryl or 5-10 membered heteroaryl ring. The ring thus formed may further be substituted with substituents selected from $R^{12}$;

G and $R^6$ can be joined together to form a saturated or unsaturated $C_{3-10}$ cycloalkyl or 3-10 membered heterocyclyl ring, which may further be fused to one or more $C_{3-10}$ cycloalkyl, 3-10 membered heterocyclyl, $C_{5-10}$ aryl or 5-10 membered heteroaryl ring. The ring thus formed may further be substituted with substituents selected from $R^{12}$;

$R^7$ represents —H, —OH or —OR$^9$;

$R^8$ represents —H, —CHO, —COOH, —CONH$_2$, —OH, —CH(=NOH), —COR$^a$, —COOR$^a$, —CONR$^a$R$^b$, —CR$^a$(=NOR$^b$), —OR$^a$, or —(CH$_2$)$_n$OR$^a$;

or $R^7$ and $R^8$ can be joined together to form a saturated or unsaturated ring, in which one or more methylene groups or methyne groups can be replaced with O, S, NR$^a$ or oxo; the ring thus formed may optionally be substituted at any available position by one or more suitable substituents selected from $R^{12}$;

or $R^8$ and Z can be joined together to form a saturated or unsaturated ring, in which one or more methylene groups or methyne groups can be replaced with O, S, NR$^a$ or oxo; the ring thus formed may optionally be substituted at any available position by one or more suitable substituents selected from $R^{12}$;

$R^9$ represents —H, $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CHO, —CONH$_2$, —COR$^a$, —CONR$^a$R$^b$, —S(O)$_2$R$^a$, —SO$_2$NR$^a$R$^b$, —P(O)R$^a$R$^b$, —P(O)NR$^a$R$^b$, —P(O)R$^a$OR$^b$, —P(O)NR$^a$OR$^b$ or —P(O)NR$^a$R$^b$; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CHO, —CONH$_2$, —COR$^a$, —CONR$^a$R$^b$, —S(O)$_2$R$^a$, —SO$_2$NR$^a$R$^b$, —P(O)R$^a$R$^b$, —P(O)OR$^a$R$^b$, —P(O)R$^a$OR$^b$, —P(O)NR$^a$OR$^b$, —P(O)NR$^a$R$^b$; further wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $R^{13}$;

$R^{10}$ represents —H, $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CR$^a$(=NOR$^b$), —S(O)R$^a$, —S(O)$_2$R$^a$, —S(O)$_2$NR$^a$R$^b$, —(CH$_2$)$_n$S(O)R$^a$, —(CH$_2$)$_n$S(O)$_2$R$^a$, —P(O)R$^a$R$^b$, —COR$^a$, —CSR$^a$, —COOR$^a$, —CSOR$^a$, —COSR$^a$, —CSSR$^a$, —CONR$^a$R$^b$ or —CSNR$^a$R$^b$; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —NO$_2$, NH$_2$; further wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $R^{13}$;

$R^{11}$ represents $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —$N_3$, —$NO_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —NH(C=NH)NH$_2$, —NHNH$_2$, —NHCHO, —NHCHS, —NHCOOH, —NHCSOH, —OH, —SH, —SO$_3$H, —CH(=NOH), —CH(=NCN), —COR$^a$, —CSR$^a$, —COOR$^a$, —CSOR$^a$, —COSR$^a$, —CONR$^a$R$^b$, —CSNR$^a$R$^b$, —COCOR$^a$, —CONR$^a$NR$^b$R$^c$, —CSNR$^a$NR$^b$R$^c$, —CSNR$^a$R$^b$, NR$^a$R$^b$, —NR$^a$SO$_2$R$^b$, —NR$^a$CONR$^b$R$^c$, —NR$^a$CSNR$^b$R$^c$, (C=NR$^b$)NR$^c$R$^d$, —NR$^a$NR$^b$R$^c$, —NR$^a$COR$^b$, —NR$^a$CSR$^b$, —NR$^a$COOR$^b$, —NR$^a$CSOR$^b$, —OR$^a$, —OCOR$^a$, —OCOOR$^a$, —OCONR$^a$R$^b$, —OCSR$^a$, —OCSOR$^a$, —ONO$_2$, —OCSNR$^a$R$^b$, SR$^a$, —S(O)R$^a$, —S(O)$_2$R$^a$, —SO$_2$NR$^a$R$^b$, —CR$^a$(=NOR$^b$), —CR$^a$(=NCOOR$^b$), —CR$^a$(=NSOR$^b$), —CR$^a$(=NSO$_2$R$^b$), —C(=NR$^a$)—NR$^b$R$^c$, —C(=NOR$^a$)—NR$^b$R$^c$, —CR$^a$(=NCN), —NCR$^a$, —P(O)R$^a$R$^b$, —P(O)OR$^a$OR$^b$, —P(O)R$^a$OR$^b$, —P(O)NR$^a$OR$^b$, —P(O)NR$^a$R$^b$, —OP(O)R$^a$R$^b$ or —NHP(O)R$^a$R$^b$; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $R^{13}$;

$R^{12}$ represents $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —$N_3$, —$NO_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —NH(C=NH)NH$_2$, —NHNH$_2$, —NHCHO, —NHCHS, —NHCOOH, —NHCSOH, —OH, —SH, —SO$_3$H, —CH(=NOH) or —CH(=NCN); wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may optionally be substituted at any available position by one or more suitable substituents selected from $R^{13}$;

$R^{13}$ represents $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —$N_3$, —$NO_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —NH(C=NH)NH$_2$, —NHNH$_2$, —NHCHO, —NHCHS, —NHCOOH, —NHCSOH, —OH, —SH, —SO$_3$H, —CH(=NOH) or —CH(=NCN);

$R^a$, $R^b$, $R^c$ and $R^d$ are independently selected from —H, $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —$N_3$, —$NO_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —NH(C=NH)NH$_2$, —NHNH$_2$, —NHCHO, —NHCHS, —NHCOOH, —NHCSOH, —OH, —SH, —SO$_3$H, —CH(=NOH), —CH(=NCN); each of which may optionally be substituted at any available position by one or more suitable substituents selected from $R^{13}$;

or $R^a$ and $R^b$ when attached to the same atom, can be joined together to form a monocyclic or polycyclic ring, in which one or more methylene groups or methyne groups can be replaced with O, S, SO, SO$_2$, NR$^a$, PR$^a$, P(=O)R$^a$ or oxo; the ring thus formed may optionally be substituted at any available position by one or more suitable substituents selected from $R^{12}$;

or $R^b$ and $R^c$ when attached to the same atom, can be joined together to form a monocyclic or polycyclic ring, in which one or more methylene groups or methyne groups can be replaced with O, S, SO, SO$_2$, NR$^a$, PR$^a$, P(=O)R$^d$ or oxo; the ring thus formed may optionally be substituted at any available position by one or more suitable substituents selected from $R^{12}$;

or $R^c$ and $R^d$ when attached to the same atom, can be joined together to form a monocyclic or polycyclic ring, in which one or more methylene groups or methyne groups can be replaced with O, S, SO, SO$_2$, NR$^a$, PR$^a$, P(=O)R$^a$ or oxo; the ring thus formed may optionally be substituted at any available position by one or more suitable substituents selected from $R^{12}$;

n represents 1, 2, 3, 4 or 5; their pharmaceutically acceptable derivatives, tautomeric forms, isomers, polymorphs, prodrugs, metabolites, salts or solvates thereof.

One embodiment of the present invention provides compounds of Formula Ia, wherein

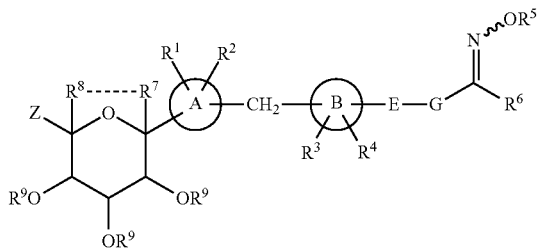

Formula Ia

Z, $R^1$, $R^2$, $R^3$, $R^4$, $R^5$, $R^6$, $R^7$, $R^8$, $R^9$, E, G, ring A and ring B are as defined herein; their pharmaceutically acceptable derivatives, tautomeric forms, isomers, polymorphs, prodrugs, metabolites, salts or solvates thereof.

A further embodiment of the present invention provides compounds of Formula Ib, wherein

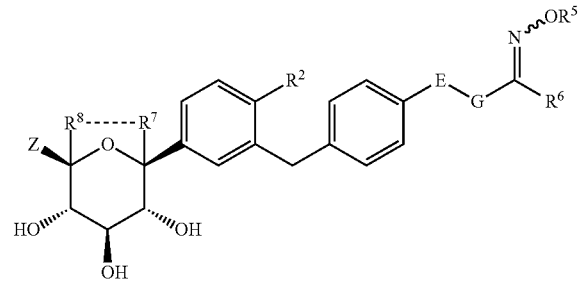

Formula Ib

Z, $R^2$, $R^5$, $R^6$, $R^7$, $R^8$, E and G are as defined herein; preferably $R^2$ is Cl, F, CH$_3$, H, CN, cyclopropyl or ethynyl; their pharmaceutically acceptable derivatives, tautomeric forms, isomers, polymorphs, prodrugs, metabolites, salts or solvates thereof.

In another embodiment of the compounds of the present invention, it is preferred that Z is selected from —$(CH_2)_nOR^a$ or —$OR^a$.

A further embodiment of the present invention provides compounds wherein $R^5$ preferably represents —H, OH or $C_{1-12}$ alkyl.

In another embodiment of the compounds of the present invention, it is preferred that $R^6$ represents —H, $C_{1-12}$ alkyl, —$NR^aR^b$ or $C_{6-10}$ aryl.

In still another embodiment of the compounds of the present invention, it is preferred that
  i. $R^7$ and $R^8$ are joined together to form a saturated ring, in which one or more methylene groups can be replaced with O; wherein the ring thus formed is unsubstituted or substituted at any available position by one or more suitable substituents selected from $R^{11}$; or
  ii. $R^7$ is H and $R^8$ is H; or
  iii. $R^7$ is —$OCH_3$ and $R^8$ is H.
  iv.

Another embodiment of the present invention provides compounds of Formula Ic, wherein Formula Ic

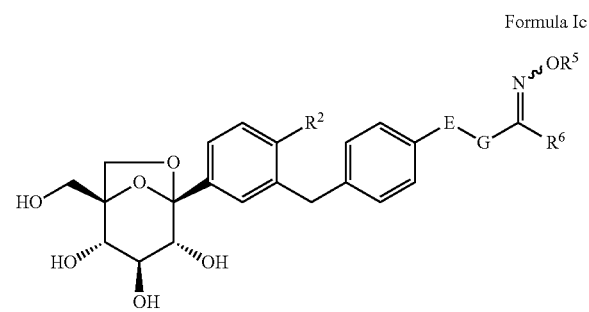

$R^5$, $R^6$, E and G are as defined herein; their pharmaceutically acceptable derivatives, tautomeric forms, isomers, polymorphs, prodrugs, metabolites, salts or solvates thereof.

A still another embodiment of the present invention provides compounds of Formula Id, wherein Formula Id

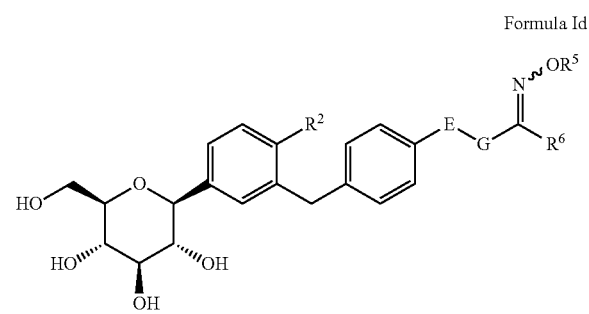

$R^5$, $R^6$, E and G are as defined herein; their pharmaceutically acceptable derivatives, tautomeric forms, isomers, polymorphs, prodrugs, metabolites, salts or solvates thereof.

A further embodiment of the present invention provides compounds of Formula Ie, wherein Formula Ie

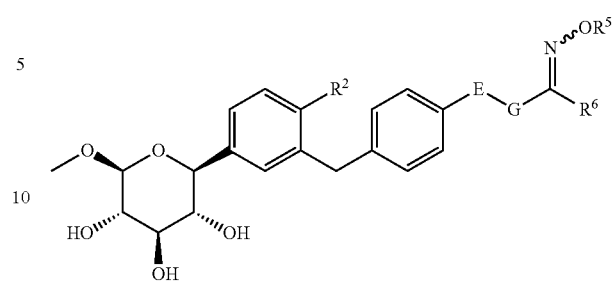

$R^5$, $R^6$, E and G are as defined herein; their pharmaceutically acceptable derivatives, tautomeric forms, isomers, polymorphs, prodrugs, metabolites, salts or solvates thereof.

In another embodiment of the compounds of the present invention, it is preferred that G is alkyl, alkylene, cycloalkyl or aryl.

In another embodiment of the compounds of the present invention, it is preferred that E is O or single bond.

In another embodiment of the compounds of the present invention, G and $R^6$ can be joined together to form a saturated or unsaturated $C_{3-10}$ cycloalkyl ring.

Definitions

Relative to the above description of the compounds of the present invention, the following definitions apply.

The term "alkyl" as used herein alone or as part of another group refers to a straight or branched chain aliphatic hydrocarbon chain, having from 1 to 12 carbon atoms. Examples of alkyl include, but are not limited to methyl, ethyl, n-propyl, isopropyl, n-butyl, n-pentyl, t-butyl and the like. Alkyl groups may further be substituted with one or more suitable substituents.

The term "alkenyl" as used herein alone or as part of another group refers to a straight or branched chain aliphatic hydrocarbon group containing at least one carbon-carbon double bond, having from 2 to 12 carbon atoms. Examples of alkenyl include, but are not limited to ethenyl, 1-propenyl, 2-propenyl, iso-propenyl, 1-butenyl, 2-butenyl, and the like. Alkenyl groups may further be substituted with one or more suitable substituents.

The term "alkynyl" as used herein alone or as part of another group refers to a straight or branched chain aliphatic hydrocarbon group containing at least one carbon-carbon triple bond, having from 2 to 12 carbon atoms. Examples of alkynyl include, but are not limited to ethynyl, propynyl, and butynyl. Alkynyl groups may further be substituted with one or more suitable substituents.

The term "cycloalkyl" refers to cyclic alkyl groups constituting of 3 to 20 carbon atoms having a single cyclic ring or multiple condensed rings, for example, fused or spiro systems, unless otherwise constrained by the definition. Such cycloalkyl groups include, by way of example, single ring structures, for example, cyclopropyl, cyclobutyl, cyclopentyl, cyclohexyl, cyclooctyl, and the like, or multiple ring structures, for example, adamantyl, and bicyclo[2.2.1]heptane, or cyclic alkyl groups to which is fused an aryl group or another cycloalkyl group, for example, indane and the like. Cycloalkyl groups may further be substituted with one or more suitable substituents. The term "cycloalkyl" may optionally contain one or more unsaturated bonds.

The term "aryl" herein refers to six to ten membered monocyclic aromatic group, for example phenyl or naphthyl ring and the like optionally substituted with one or more suitable substituents. The aryl group may optionally be fused with one or two cycloalkyl group(s) or other aryl group(s) resulting in polycyclic ring system. The fused group may be further substituted with one or more suitable substituents.

The term "heteroaryl" unless and otherwise specified refers to a five to ten membered aromatic monocyclic ring structure, containing one to five heteroatoms independently selected from N, O, S or P. "Heteroaryl" also includes, but is not limited to, bicyclic or tricyclic rings, wherein the above defined heteroaryl ring is fused to one or two rings independently selected from the group consisting of an aryl ring, a cycloalkyl ring, a heterocyclyl ring and another monocyclic heteroaryl ring. Examples of heteroaryl groups include, but are not limited to, oxazolyl, imidazolyl, pyrrolyl, 1,2,3-triazolyl, 1,2,4-triazolyl, tetrazolyl, thiazolyl, oxadiazolyl, benzoimidazolyl, thiadiazolyl, pyridinyl, pyridazinyl, pyrimidinyl, thienyl, isoxazolyl, triazinyl, furanyl, benzofuranyl, indolyl, benzothiazolyl, benzoxazolyl, imidazo[1,2-α]pyrimidine, imidazo[1,2-a]pyrazine, tetrahydroquinoline and the like. The heteroaryl group may be further substituted at any available position with one or more suitable substituents. Point of attachment of heteroaryl group to another group may be through carbon or heteroatom.

The term "heterocyclyl" unless otherwise specified refers to a non-aromatic 3 to 14 membered monocyclic cycloalkyl group, fully or partially unsaturated, with one to five heteroatoms independently selected from N, O, S or P. "Heterocyclyl" also includes, but is not limited to, bicyclic or tricyclic rings, wherein the heterocyclyl ring is fused to one or two rings independently selected from the group consisting of an aryl ring, a cycloalkyl ring, a heteroaryl ring or heterocyclyl ring. The heterocyclyl group may be further substituted at any available position with one or more suitable substituents. Examples of heterocyclyl groups include but are not limited to, morpholinyl, oxazolidinyl, tetrahydrofuranyl, dihydrofuranyl, dihydropyridinyl, dihydroisooxazolyl, dihydrobenzofuryl, azabicyclohexyl, dihydroindonyl, piperidinyl or piperazinyl. Point of attachment of heterocyclyl group to another group may be through carbon or heteroatom.

"Halogen" refers to F, Cl, Br or I.

"Hydroxy" or "hydroxyl" refers to the group —OH.

The term "oxo" refers to carbonyl group represented as >C=O.

In all the above definitions, nitrogen, sulphur and phosphorus heteroatom can optionally be quaternerized or oxidized wherever permissible.

Examples of suitable substituents groups include, but are not limited to, alkyl, alkenyl, alkynyl, aryl, cycloalkyl, heterocyclyl, heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —N(C=NH)NH$_2$, —NHNH$_2$, —NHCHO, —NHCHS, —NHCOOH, —NHCSOH, —OH, —SH, —SO$_3$H, —CH(=NOH), —CH(=NCN) and the like.

The term "Protecting Group" or "PG" refers to a group which is in a modified form to preclude undesired side reactions at the protected site. The term protecting group, unless otherwise specified, may be used with groups, for example, hydroxy, amino, carboxy and examples of such groups are found in T. W. Greene. et al. "*Protecting Groups in Organic Synthesis,*" 3$^{rd}$ Ed, Wiley, New York, which is incorporated herein by reference. The species of the carboxylic protecting groups, amino protecting groups or hydroxy protecting groups employed are not critical, as long as the derivatised moieties/moiety is/are stable to conditions of subsequent reactions and can be removed without disrupting the remainder of the molecule. Examples of suitable hydroxy and amino protecting groups include but are not limited to trimethylsilyl, triethylsilyl, o-nitrobenzyloxycarbonyl, p-nitrobenzyloxycarbonyl, t-butyldiphenylsilyl, t-butyldimethylsilyl, acetyl, trifluoroacetyl, benzyloxycarbonyl (CBz), t-butoxycarbonyl (Boc), 9-fluorenylmethylenoxycarbonyl (Fmoc), 2,2,2-trichloroethyloxycarbonyl, allyloxycarbonyl and the like. Examples of suitable carboxy protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl, t-butyl and the like.

"Subject" includes humans, non-human mammals (e.g., dogs, cats, rabbits, cattle, horses, sheep and the like) or non-mammals (e.g., birds and the like).

The term "therapeutically effective amount" means the amount of a compound that, when administered to a subject for treating a disease, is sufficient to effect such treatment for the disease. The "therapeutically effective amount" will vary depending on the compound, the disease and its severity, weight, physical condition and responsiveness of the subject to be treated, among other factors.

A "pharmaceutically acceptable salt" refers to salts prepared from pharmaceutically acceptable non-toxic bases or acids including inorganic or organic bases and inorganic or organic acids. A "pharmaceutically acceptable salt" also encompasses any compound according to the present invention that is utilized in the form of a salt thereof, especially where the salt confers on a compound improved pharmacokinetic properties as compared to the free form of compound or a different salt form of the compound.

Term comprises/comprising and grammatical variations thereof when used in this specification are to be taken to specify the presence of stated features, integers, steps or components or groups thereof, but do not preclude the presence or addition of one or more other features, integers, steps, components or groups thereof.

Asymmetric centres may exist in the compounds of the present invention. The compounds of Formula I may have one or more stereogenic centres and so can exhibit optical isomerism. All such isomers including enantiomers, diastereomers, and epimers are included within the scope of this invention. Furthermore, the invention includes such compounds as single isomers (R and/or S) and as mixtures, including racemates. If desired, racemic mixtures of the compounds may be separated so that the individual enantiomers are isolated. The separation may be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Starting materials of particular stereochemistry may either be commercially available or may be made by the methods described herein and resolved by techniques well known in the art. The independent syntheses of these diastereomers or their chromatographic separations may be achieved as known in the art by appropriate modifications.

Certain compounds according to Formula I, can also exist as tautomers, which have different points of attachment of hydrogen accompanied by one or more double bond shifts. These tautomers, either separately or as mixtures, are also considered to be within the scope of the invention.

The present invention also encompasses geometrical isomers of compounds of Formula I and the mixtures thereof.

The geometrical isomers may exist in E or Z; Syn or anti configurations. These geometrical isomers, either separately or as mixtures, are also considered to be within the scope of the invention.

Certain compounds according to Formula I, may also exist as polymorphs. Various "polymorphs" of a compound of general Formula I forming part of this invention may be prepared by crystallization of a compound of Formula I under different conditions. For example, by using different solvents commonly used or their mixtures for recrystallization; crystallizations at different temperatures; various modes of cooling, ranging from very fast to very slow cooling during crystallizations, heating or melting the compound followed by gradual or fast cooling may also obtain polymorphs. The presence of polymorphs may be determined by solid probe NMR spectroscopy, IR spectroscopy, differential scanning calorimetry, powder X-ray diffraction or such other techniques.

Particularly useful examples of the present invention include but are not limited to the compounds selected from Table 1, including their pharmaceutically acceptable derivatives, tautomeric forms, isomers, polymorphs, prodrugs, metabolites, salts or solvates thereof:

TABLE 1

| Compound No | Structure |
|---|---|
| 1 | 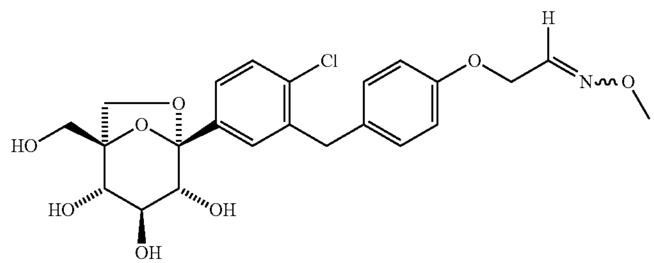 [SMILES: CON=CCOc1ccc(Cc2cc([C@]34OC[C@](CO)(O3)[C@@H](O)[C@H](O)[C@H]4O)ccc2Cl)cc1] |
| 2 | 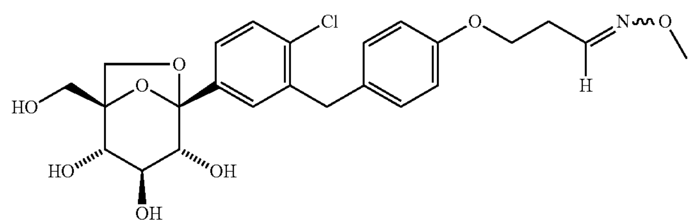 [SMILES: CON=CCCOc1ccc(Cc2cc([C@]34OC[C@](CO)(O3)[C@@H](O)[C@H](O)[C@H]4O)ccc2Cl)cc1] |
| 3 | 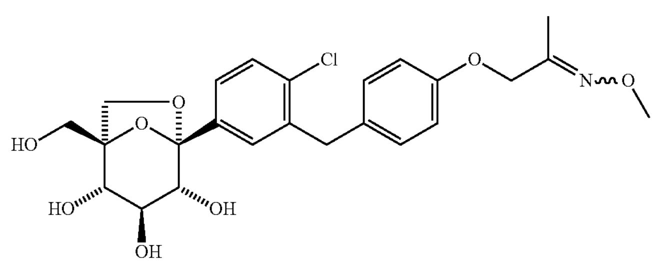 [SMILES: CON=C(C)COc1ccc(Cc2cc([C@]34OC[C@](CO)(O3)[C@@H](O)[C@H](O)[C@H]4O)ccc2Cl)cc1] |
| 4 | 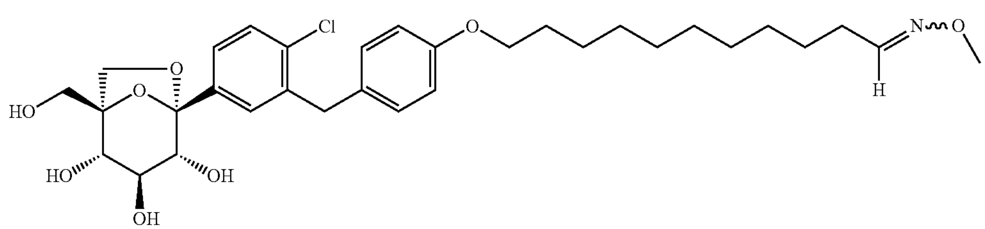 [SMILES: CON=CCCCCCCCCCCOc1ccc(Cc2cc([C@]34OC[C@](CO)(O3)[C@@H](O)[C@H](O)[C@H]4O)ccc2Cl)cc1] |
| 5 | 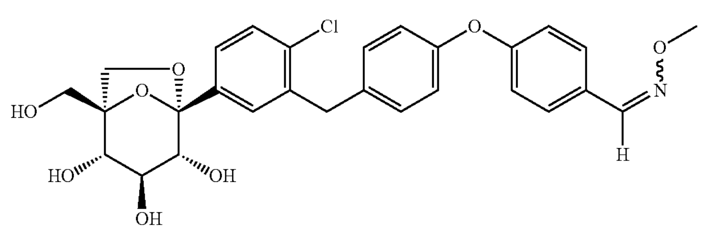 [SMILES: CON=Cc1ccc(Oc2ccc(Cc3cc([C@]45OC[C@](CO)(O4)[C@@H](O)[C@H](O)[C@H]5O)ccc3Cl)cc2)cc1] |

TABLE 1-continued

| Compound No | Structure |
| --- | --- |
| 6 | 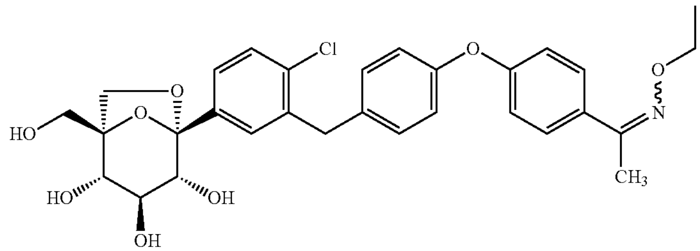 [SMILES: CCON=C(C)c1ccc(Oc2ccc(Cc3cc([C@]45OC[C@](CO)(O4)[C@@H](O)[C@H](O)[C@H]5O)ccc3Cl)cc2)cc1] |
| 7 | 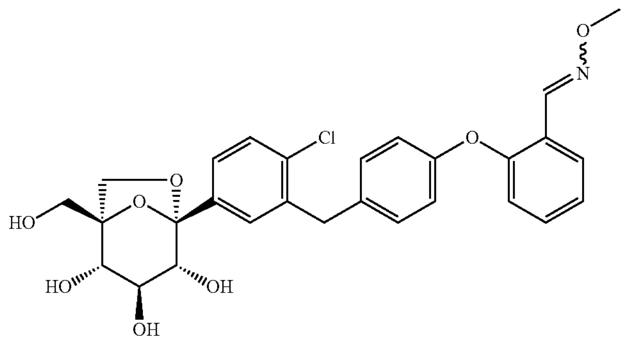 [SMILES: CON=Cc1ccccc1Oc1ccc(Cc2cc([C@]34OC[C@](CO)(O3)[C@@H](O)[C@H](O)[C@H]4O)ccc2Cl)cc1] |
| 8 | 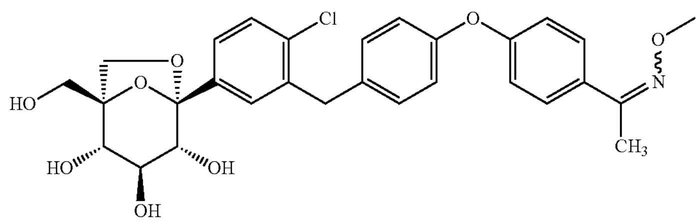 [SMILES: CON=C(C)c1ccc(Oc2ccc(Cc3cc([C@]45OC[C@](CO)(O4)[C@@H](O)[C@H](O)[C@H]5O)ccc3Cl)cc2)cc1] |
| 9 | 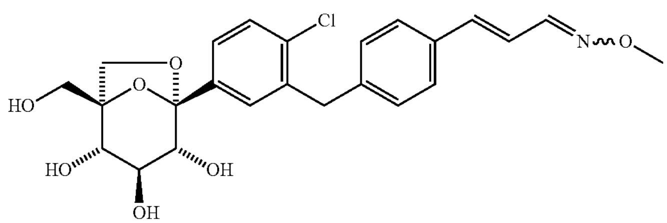 [SMILES: CON=C/C=C/c1ccc(Cc2cc([C@]34OC[C@](CO)(O3)[C@@H](O)[C@H](O)[C@H]4O)ccc2Cl)cc1] |
| 10 | 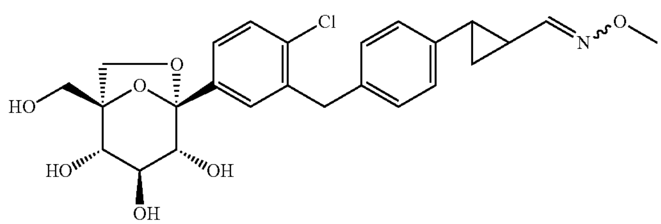 [SMILES: CON=CC1CC1c1ccc(Cc2cc([C@]34OC[C@](CO)(O3)[C@@H](O)[C@H](O)[C@H]4O)ccc2Cl)cc1] |
| 11 | 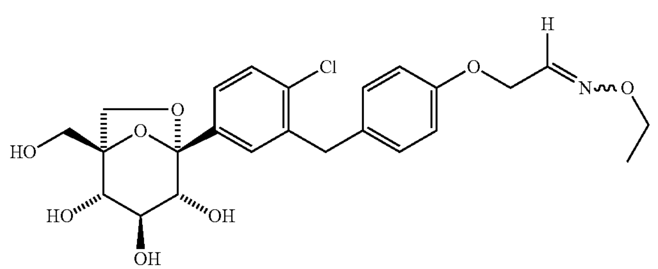 [SMILES: CCON=CCOc1ccc(Cc2cc([C@]34OC[C@](CO)(O3)[C@@H](O)[C@H](O)[C@H]4O)ccc2Cl)cc1] |

TABLE 1-continued

| Compound No | Structure |
|---|---|
| 12 | *(structure image)* |
| 13 | *(structure image)* |
| 14 | *(structure image)* |
| 15 | *(structure image)* |
| 16 | *(structure image)* |
| 17 | *(structure image)* |

TABLE 1-continued

| Compound No | Structure |
|---|---|
| 18 | (glucose)-phenyl-CH2-phenyl-O-CH=N-OCH3 (meta-substituted phenyl on glucose) |
| 19 | (glucose)-(4-Cl-phenyl)-CH2-phenyl-O-CH=N-OCH3 |
| 20 | (glucose)-(4-Cl-phenyl)-CH2-phenyl-O-CH2-C(=N-OH)-NH2 |
| 21 | (glucose)-(4-Cl-phenyl)-CH2-phenyl-O-CH2-CH=N-OCH3 |
| 22 | (glucose)-(4-Cl-phenyl)-CH2-phenyl-O-CH2-C(=N-OMe)-phenyl |
| 23 | (glucose)-(4-Cl-phenyl)-CH2-phenyl-O-CH=N-OC2H5 |

TABLE 1-continued

| Compound No | Structure |
|---|---|
| 24 | 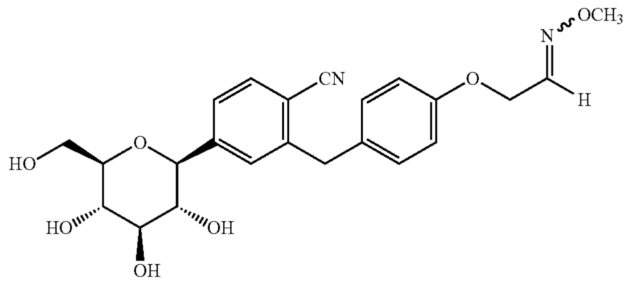 [SMILES: CON=CCOc1ccc(Cc2cc([C@@H]3O[C@H](CO)[C@@H](O)[C@H](O)[C@H]3O)ccc2C#N)cc1] |
| 25 | 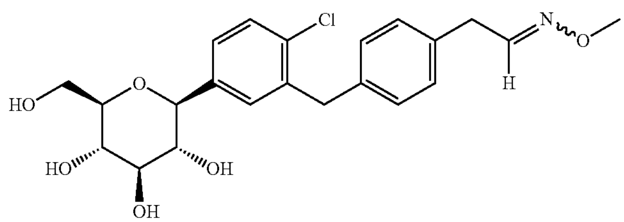 [SMILES: CON=CCc1ccc(Cc2cc([C@@H]3O[C@H](CO)[C@@H](O)[C@H](O)[C@H]3O)ccc2Cl)cc1] |
| 26 | 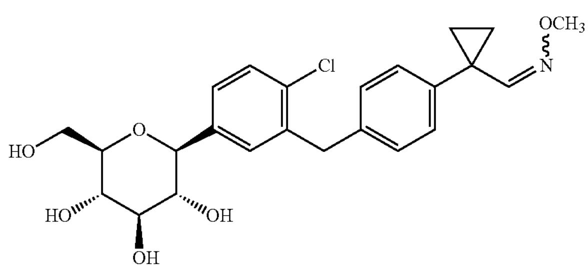 [SMILES: CON=CC1(c2ccc(Cc3cc([C@@H]4O[C@H](CO)[C@@H](O)[C@H](O)[C@H]4O)ccc3Cl)cc2)CC1] |
| 27 | 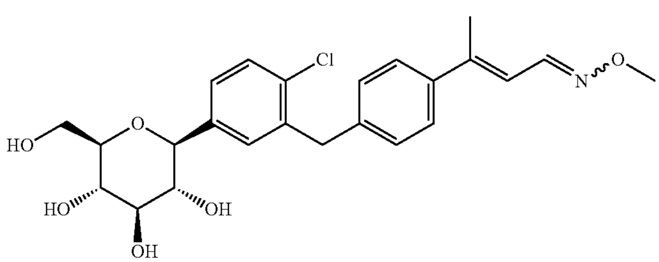 [SMILES: CON=C/C=C(\C)c1ccc(Cc2cc([C@@H]3O[C@H](CO)[C@@H](O)[C@H](O)[C@H]3O)ccc2Cl)cc1] |

TABLE 1-continued

| Compound No | Structure |
|---|---|
| 28 | *(structure: methyl glucoside-aryl-Cl-benzyl-aryl-O-CH₂-CH=N-OCH₃)* |
| 29 | *(structure: methyl glucoside-aryl-Cl-benzyl-aryl-O-CH₂CH₂-CH=N-OCH₃)* |
| 30 | *(structure: methyl glucoside-aryl-Cl-benzyl-aryl-O-CH₂-C(CH₃)=N-OCH₃)* |

The compounds of the present invention may be prepared by the following reaction sequences as depicted in Scheme No 1 to 10. The compounds disclosed may also be prepared by techniques known in the art and familiar to the skilled organic chemist. All of the starting materials are either commercially available or can be prepared by procedures that would be well known to one of ordinary skill in organic chemistry.

"Lg" is used to denote an appropriate leaving group and as such may vary in nature depending on the exact reaction conditions employed. Some typical leaving groups may be fluoro, chloro, bromo, iodo, tosylate, mesylate, triflate and the like, but these should not be construed as limiting as many other leaving groups are also well known to those skilled in the art.

Scheme 1

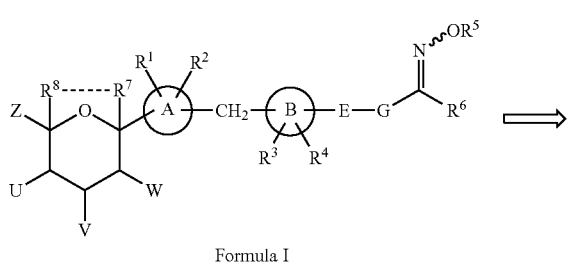

Formula I

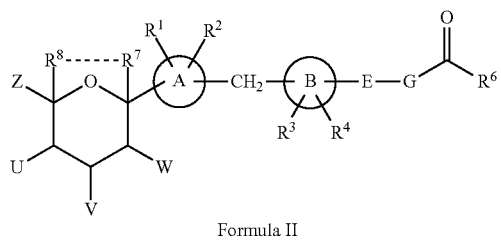

Formula II

The compounds of the Formula I can be prepared from the compounds of Formula II as shown in the Scheme 1 by treating with compounds of Formula III ($R^5ONH_2$) or their salts in the presence of a suitable base such as $K_2CO_3$, $Na_2CO_3$, $NaHCO_3$, pyridine, DIPEA, $NEt_3$ and the like in a solvent selected from but not limited to methanol, ethanol, pyridine, toluene, benzene or a combination thereof; optionally in the presence of NaOAc or ZnO.

Scheme 1'

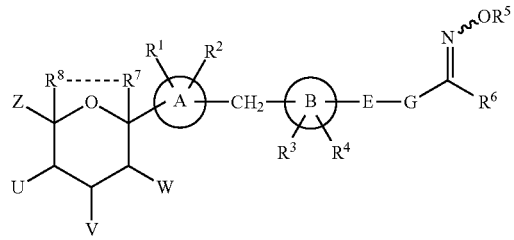

Formula I

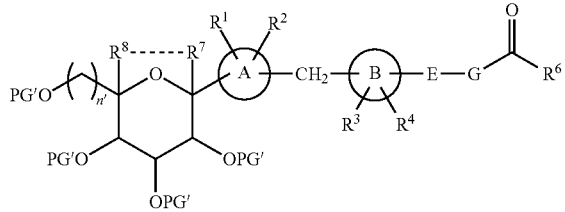

Formula II'

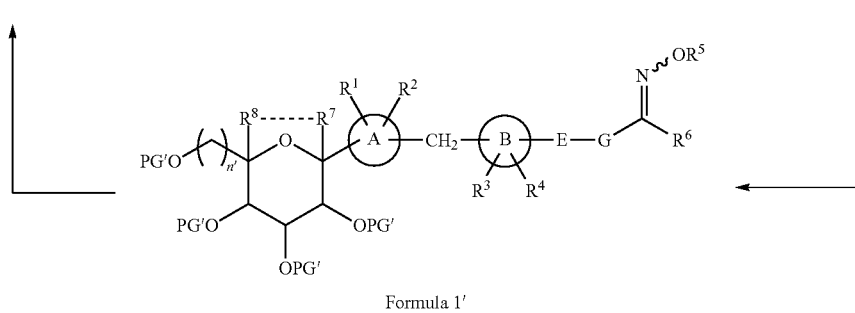

Formula 1' n' = 0 or 1

Alternately, compounds of Formula I can be prepared from compounds of Formula II' in a two step procedure as described in Scheme 1'. The compounds of Formula II' wherein U, V and/or W represent suitably protected hydroxyl groups, for example but not limited to O-acetyl, O-benzyl, O-p-methoxybenzyl and O-silyl, the oxime formation step described above can be followed by a suitable deprotection step to obtain the compounds of Formula I. Depending upon the nature of the protecting group of the compounds of Formula I' (Novel Intermediates), deprotection method can be chosen by person skilled in the art. Such deprotection methods include but not limited to, treatment with alkali hydroxide, $H_2$/Pd—C, TMSI, $BCl_3$, pTSA, TFA, HCl, $H_2SO_4$, HBr, HI, TBAF, HF, DDQ, CAN, $OsO_4$, $NaIO_4$ and $Pd(PPh_3)_4$.

example but not limited to mesylate or tosylate in the presence of a base such as sodium hydride, potassium carbonate, LDA, potassium tert-butoxide, sodium tert-butoxide, LiHMDS and the like in a suitable solvent such as but not limited to THF, DMF, DMSO, acetone or a combination thereof. These types of transformations can be performed by methods as described in U.S. Pat. No. 5,120,849 and *Chem. Pharm. Bull,* 2003, 51, 138-151. The alkylated hydroxy phthalimide intermediate can be converted to compounds of Formula III by treating with reagents such as hydrazine hydrate, 2-aminoethanol and the like in the presence of a suitable solvent for example but not limited to methanol, ethanol or isopropanol.

Scheme 2

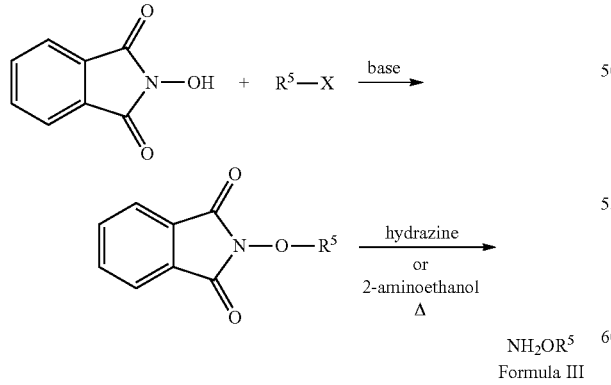

The commercially non available hydroxylamine derivatives of Formula III ($NH_2OR^5$) can be prepared by following Scheme 2. Alkylation of N-hydroxyphthalimide can be done using $R^5$—X, wherein X can be halogen or a leaving group for Scheme 3

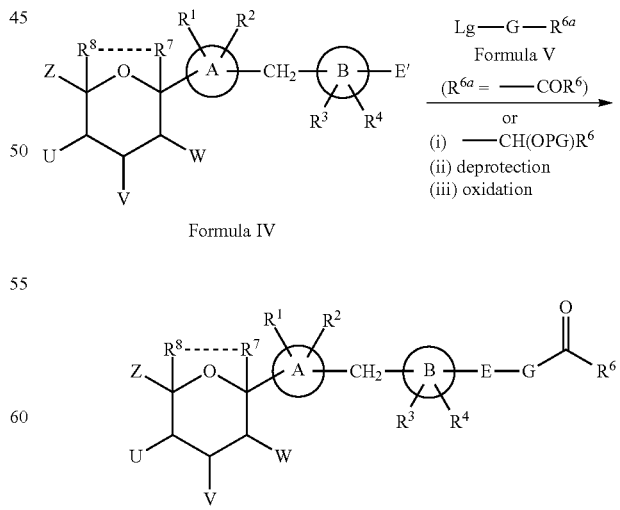

E' = OH, SH or $NHR^{10}$
E = O, S or $NR^{10}$

The compounds of the Formula II (wherein E is O, S or $NR^{10}$) can be synthesized starting from compounds of Formula IV by following the Scheme 3. The compounds of Formula IV, wherein E' is OH, SH or $NHR^{10}$ can be treated with compounds of Formula V under suitable conditions familiar to a person skilled in the art to obtain the compounds of Formula II. Such conditions include but not limited to using a base selected from $K_2CO_3$, $Cs_2CO_3$, NaOH, KOH optionally in presence of a phase transfer catalyst like tetraalkyl ammonium salts and the like in a suitable solvent such as DMF, acetone, DCM, water or a combination thereof. Depending on the nature of $R^{6a}$ in compounds of Formula V formation of compounds of Formula II can be a one step or three step procedure. The three step procedure involves the coupling compounds of Formula IV and Formula V followed by removal of the protecting group and oxidation of the resulting hydroxyl moiety. The deprotection and oxidation reaction conditions can be chosen by a person skilled in the art.

Scheme 4

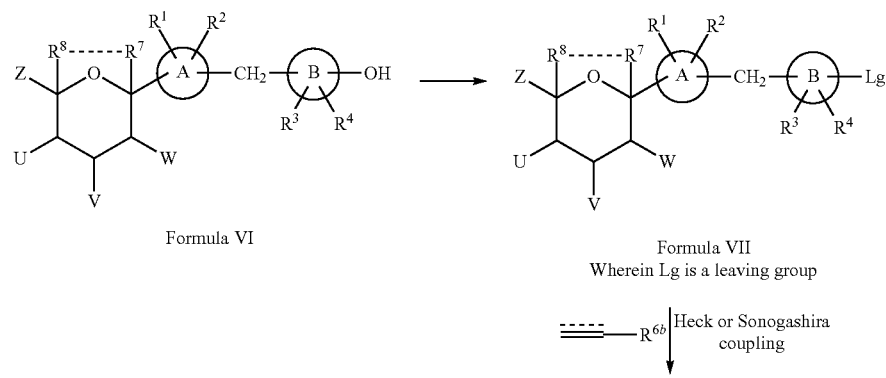

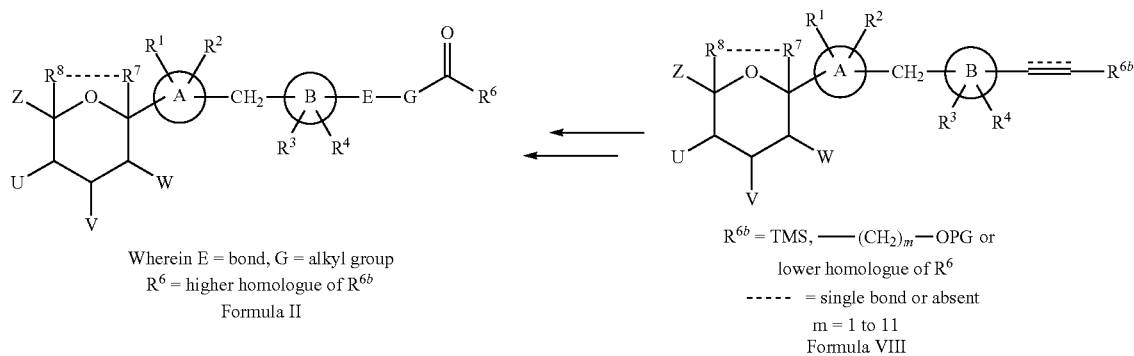

The compounds of Formula II wherein E is a single bond can be prepared by following the Scheme 4. Hydroxy group of the compounds of Formula VI can be converted to a leaving group such as but not limited to trifluoromethanesulfonate by treating with trifluoromethanesulfonic anhydride in presence of a base for example, but not limited to pyridine, $NEt_3$ usually in a suitable solvent such as DCM, THF, ACN and the like to obtain the compounds of Formula VII. The compounds of Formula VIII can be prepared by coupling compounds of Formula VII with ≡—$R^{6b}$ under Heck or Sonogashira coupling conditions. The compounds of Formula VIII containing alkyne group, where in $R^{6b}$ is TMS or lower homologue of $R^6$, can be regioselectively hydrated to form compounds of Formula II. Alternately, the compounds of Formula VIII containing alkyne or alkene group, where in $R^{6b}$ is —$(CH_2)_n$OPG can be converted into compounds of Formula II following a sequence of reactions comprising reduction, deprotection, oxidation, alkylation and oxidation. The exact reaction conditions can be chosen by a person skilled in the art.

The compounds of the Formula VI, wherein $R^8$ and $R^7$ are H and '—' is absent, can be prepared by following the procedure as described in WO2011070592.

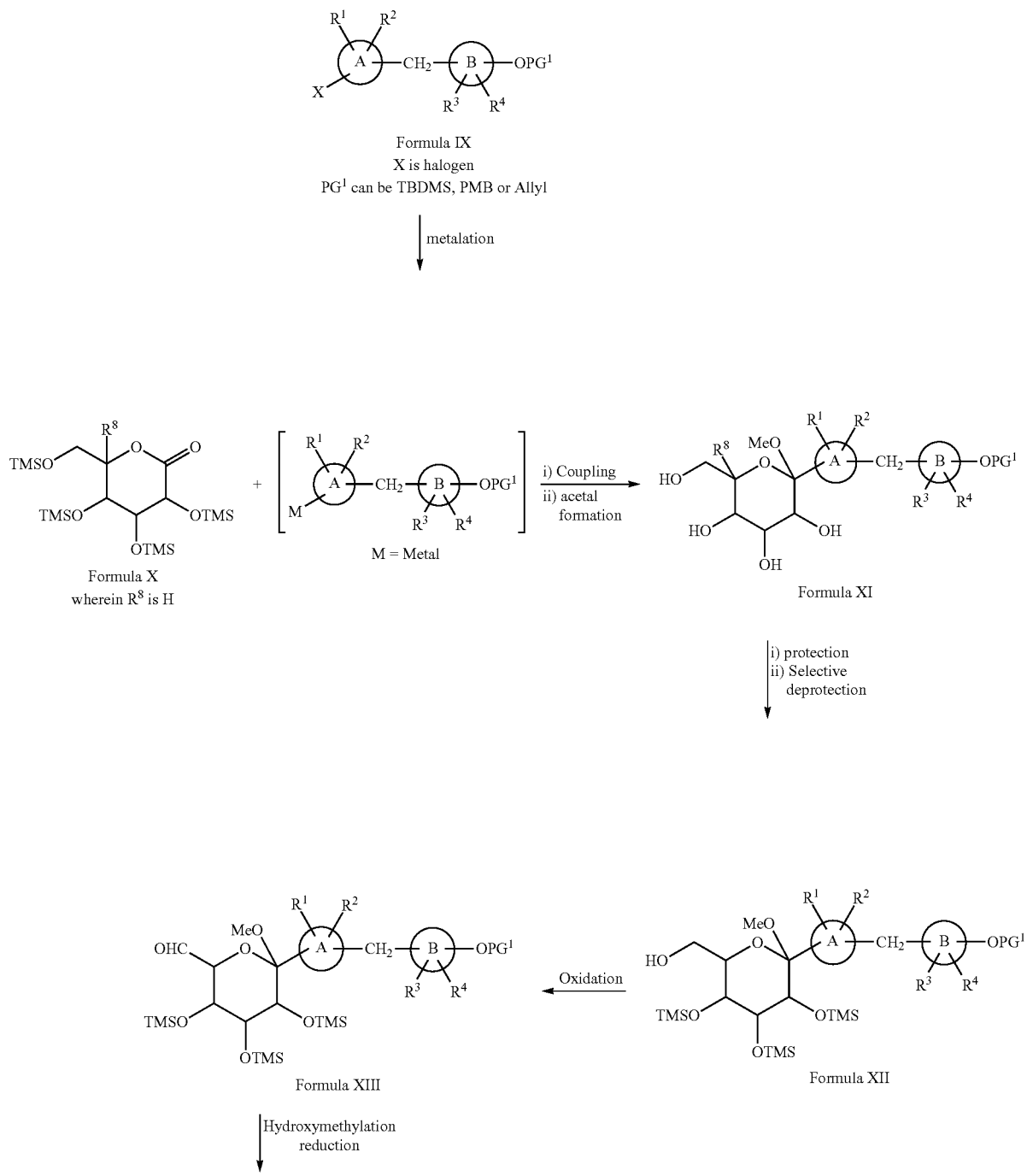

Scheme 5

-continued

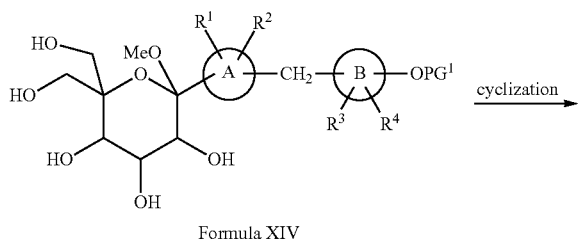

Formula XIV

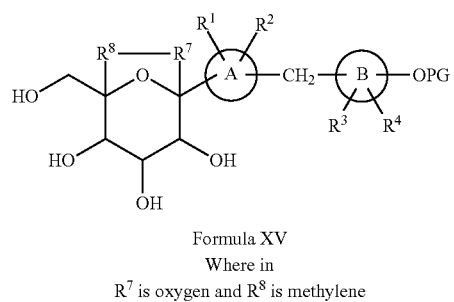

Formula XV
Where in
R⁷ is oxygen and R⁸ is methylene

↓ Protection

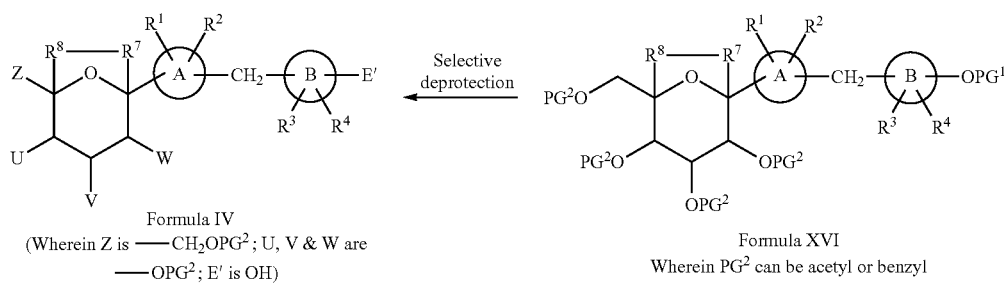

Formula IV
(Wherein Z is —CH₂OPG²; U, V & W are —OPG²; E' is OH)

Formula XVI
Wherein PG² can be acetyl or benzyl

The compounds of the Formula IV, wherein $R^8$ and $R^7$ are methylene and oxygen respectively which are linked through a bond, can be prepared by following the steps provided in Scheme 5. Compounds of Formula IX and Formula X can be prepared by following the procedure given in US20070049537. The compounds of Formula IX can be metalated with reagents such as but not limited to $^n$BuLi, $^s$BuLi, $^t$BuLi, Li, $^i$PrMgCl or $^i$PrMgCl/LiCl in a suitable solvent such as but not limited to toluene, THF, diethyl ether or combination thereof. The resulting metalated species can be treated with compounds of Formula X at temperatures ranging from −100 to 50° C. This step is followed by an acetal formation reaction, for example but not limited to treatment with methanesulfonic acid in presence of methanol to obtain compounds of Formula XI. Compounds of Formula XI can be converted to compounds of Formula XII by protecting all free hydroxyl groups with TMS by using TMSCl in the presence of a base such as but not limited to NEt₃, DIPEA, NMM, imidazole or pyridine in a suitable solvent for example THF, DCM or ACN and the like. Thus obtained tetra silyl intermediate can be treated with silyl deprotecting agents for example but not limited to K₂CO₃, TBAF, a combination of KF-crownether, NBS, SiF₄, BF₃.Et₂O, CF₃SO₃SiMe₃ or aqueous acids in a suitable solvent such as MeOH, DCM, THF, ACN and the like, under tuned conditions to achieve selective deprotection of primary hydroxyl group. Thus obtained compounds of Formula XII can be oxidized to compounds of Formula XIII by using various reagents in combination with DMSO and a base such as but not limited to NEt₃, DIPEA or collidine. The reagents that can be used for this transformation are for example but not limited to Ac₂O, oxalyl chloride, DCC, SO₃.Py. Alternately, the compounds of Formula XII can be oxidized to compounds of Formula XIII by using TPAP, TPAP and NMO, TEMPO, TEMPO and NaOCl, MnO₂, BaMnO₄, CrO₃.Py, PCC, PDC, Dess-Martin periodinane, O-iodoxybenzoic acid, oxone and the like. The compounds of Formula XIII can be converted to compounds of Formula XIV by using formaldehyde or para-formaldehyde in the presence of a suitable base such as but not limited to NaOEt, NaOH, KOH, K₂CO₃ or potassium phosphate in a suitable solvent such as dioxane, methanol, ethanol, THF or a combination thereof.

Alternately the primary hydroxyl group of compounds of Formula XI can be converted into a leaving group such as but not limited to tosylate, mesylate or iodo by treatment with p-tolenesulfonyl chloride, methane sulfonyl chloride or iodine in combination with a suitable base such as pyridine, lutidine, collidine, Na₂CO₃ or K₂CO₃, optionally in presence of a solvent such as but not limited to DCM, DCE, DMF or DMSO. Thus obtained intermediate is heated at temperatures ranging from 60 to 180° C. in pyridine, lutidine or collidine under Kornblum oxidation conditions to afford the aldehyde of Formula XIII. This aldehyde can be treated with formaldehyde or paraformaldehyde in the presence of a suitable base such as but not limited to NaOEt, NaOH, KOH, $K_2CO_3$ or potassium phosphate in a suitable solvent such as dioxane, methanol, ethanol, THF or a combination thereof to furnish compounds of formula XIV. The compounds of Formula XIV can be treated with a suitable acid such as methanesulfonic acid, trifluoroacetic acid, silica gel impregnated with pTSA, HCl, $H_2SO_4$ and the like in a suitable solvent for example but not limited to DCM, DCE, MeOH or acetic acid to furnish the compounds of Formula XV. Thus obtained bicyclic compounds of Formula XV can be protected with acetyl or benzyl groups by using conditions familiar to the person skilled in the art to obtain compounds of Formula XVI. Such conditions include but not limited to the treatment with acetic anhydride, acetyl chloride, benzyl bromide, benzyl chloride in the presence of a suitable base such as but not limited to $NEt_3$, DIPEA, pyridine, DMAP, $K_2CO_3$ or NaOH in a suitable solvent for example DCM, DMF, THF, acetone or a combination there of.

The compounds of Formula XVI can be converted to the compounds of Formula IV by selective deprotection of $PG^1$ by the methods known to a person skilled in the art. These deprotection methods include but not limited to, treatment with acids such as trifluoroacetic acid, HCl, $H_2SO_4$, HBr, HI and the like in a suitable solvent like DCM, dichloroethane, diethylether, diisopropylether, THF, dioxane, acetonitrile, methanol and the like or combination thereof. Alternately, compounds of Formula XVI can be converted to compounds of Formula IV by deprotection reactions involving reagents such as but not limited to TBAF or hydrogen fluoride in solvents such as DCM, dichloroethane, THF, dioxane or pyridine and the like. An oxidative method using reagents for example but not limited to DDQ, CAN or a combination of $OsO_4$, $NaIO_4$ and NMO in a suitable solvent can also be employed to obtain compounds of Formula IV. Another method for this selective deprotection can be metal catalyzed reactions involving $Pd(PPh_3)_4$ or Pd/C in presence of alkali base or 1,3-dimethyl barbituric acid in a suitable solvent such as but not limited to THF, methanol or DME.

Scheme 6

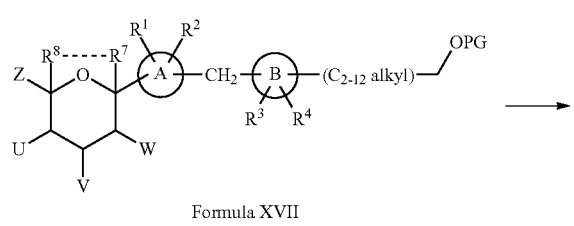

Formula XVII

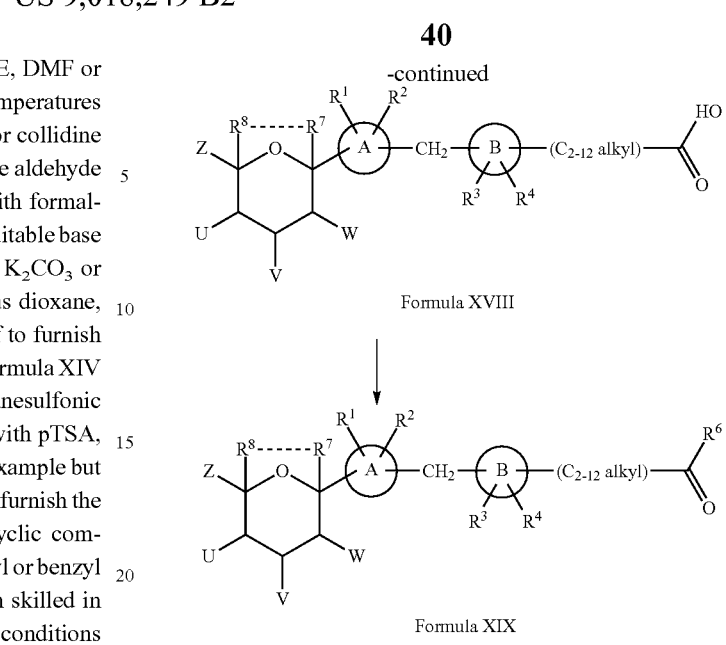

Formula XVIII

Formula XIX

Also, compounds of Formula II wherein E is bond and G is alkyl group (as depicted in Formula XIX), can be synthesized following the Scheme 6. The compounds of the Formula XVII (prepared by following the procedure as described in WO2011070592), can be converted into compounds of Formula XVIII by deprotecting the OPG followed by oxidation of the free hydroxyl group. The deprotection can be carried out by the methods known to a person skilled in the art. Such deprotection methods include but not limited to, treatment with acids such as pTSA, trifluoro acetic acid, HCl, $H_2SO_4$, HBr, HI and the like in a suitable solvent like DCM, dichloroethane, diethylether, diisopropylether, THF, dioxane, acetonitrile, methanol and the like or combination thereof. Alternate reagents include but not limited to TBAF or hydrogen fluoride in solvents such as DCM, dichloroethane, THF, dioxane or pyridine and the like. An oxidative deprotection using reagents for example but not limited to DDQ, CAN or a combination of $OsO_4$, $NaIO_4$ and NMO in a suitable solvent can also be employed. Alternately, the deprotection can be achieved by metal catalyzed reactions involving $Pd(PPh_3)_4$ or Pd/C in presence of alkali base or 1,3-dimethyl barbituric acid in a suitable solvent such as but not limited to THF, methanol or DME. The oxidation of the resulting free hydroxyl group can be done by using various reagents in combination with DMSO and a base such as but not limited to $NEt_3$, DIPEA or collidine. The reagents that can be used for this transformation are for example but not limited to $Ac_2O$, oxalyl chloride, DCC, $SO_3.Py$. Alternately, oxidation can be done by using TPAP, TPAP and NMO, TEMPO, TEMPO and NaOCl, $MnO_2$, $BaMnO_4$, $CrO_3.Py$, PCC, PDC, Dess-Martin periodinane, O-iodoxybenzoic acid, oxone and the like. The compounds of Formula XVIII can be directly converted in to compounds of Formula I by treating with compounds of Formula III as described in Scheme 1'.

Alternatively, the compounds of Formula XIX where $R^6 \neq H$ can be obtained from compounds of Formula XVIII by alkylation reaction using appropriate organometallic reagents, followed by oxidation of the secondary hydroxyl group.

Scheme 7

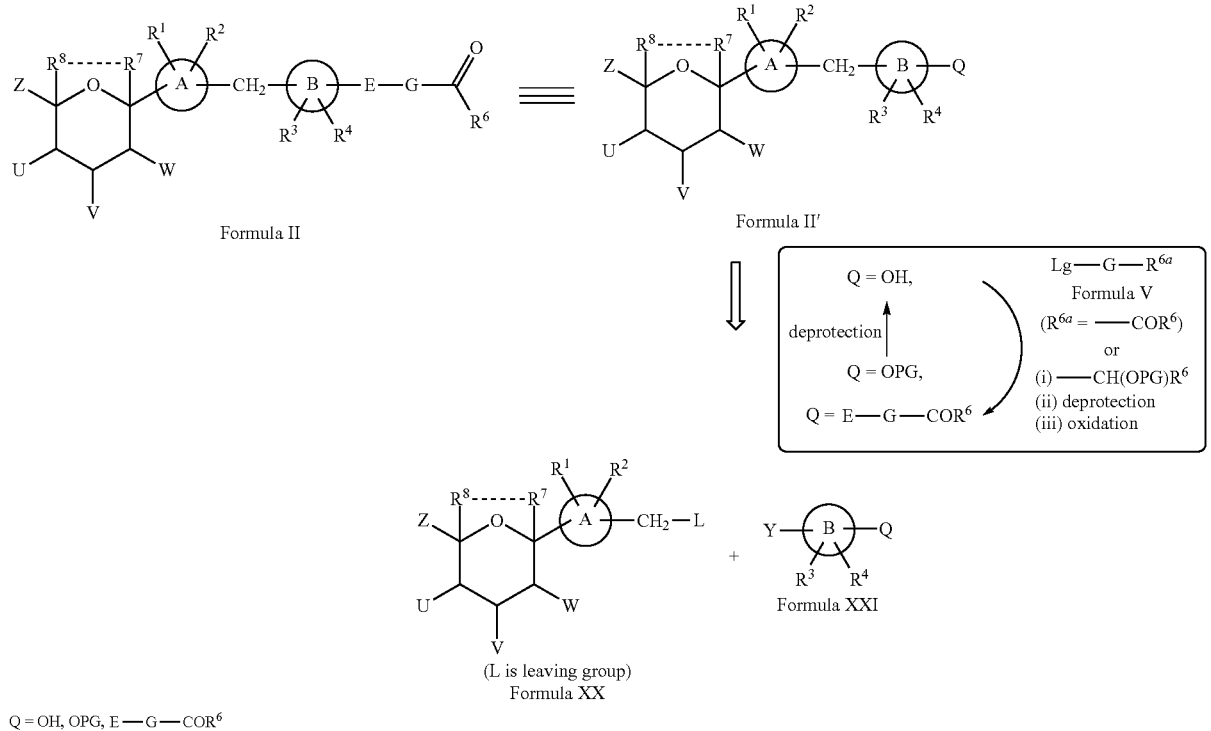

Another method for the synthesis of compounds of Formula II (wherein Q is E-G-COR$^6$) by following the Scheme 7 involves the coupling of compounds of Formula XXI with compounds of Formula XX wherein L represents groups such as but not limited to halogen, triflate or phosphate and Y represents suitably substituted derivatives of Boron, Tin, Zinc, Magnesium or Silicon. The coupling reaction can be conducted in the presence of a metal or its derivatives for example but not limited to Palladium, Nickel, Rhodium, Copper, Iron or Gold.

In the compounds of Formula XXI or II', Q can be interconverted from OPG to OH by standard deprotections conditions familiar to a person skilled in the art. Further, when Q is OH, it can be converted to E-G-COR$^6$ by following the sequence described in Scheme 3.

The compounds of the Formula XXIII can be prepared from compounds of Formula X and compounds of Formula XXII by following Scheme 8. The compounds of Formula XXII (can be prepared according to the procedure given in PCT application WO2008034859) can be metalated by treating with reagents such as but not limited to $^n$BuLi, $^s$BuLi, $^t$BuLi, Li, $^i$PrMgCl or $^i$PrMgCl/LiCl in a suitable solvent such as but not limited to toluene, THF, diethylether or combination thereof. The resulting metalated species can be treated with compounds of Formula X (can be prepared by following the procedure given in US20070049537) at temperatures ranging from −100 to 50° C. In situ treatment of the resulting intermediate with methane sulfonic acid in presence of methanol can lead to the compounds of Formula XXIII.

The free hydroxyl groups of compounds of Formula XXIII can be protected with acetyl groups to obtain compounds of Formula XXIV by treating with acetic anhydride or acetyl chloride in the presence of a suitable base such as but not limited to NEt$_3$, DIPEA, pyridine, DMAP, K$_2$CO$_3$ or NaOH in a suitable solvent for example but not limited to DCM, DMF, THF, ACN or a combination there of. Thus obtained compounds of Formula XXIV can be converted to compounds of Formula XXV by treating with reagents for example, but not limited to triethylsilane or triisopropylsilane in combination with borontrifluoride etherate, AlCl$_3$, trifluoroacetic acid, trifluoromethane sulfonic acid in a suitable solvent such as acetonitrile, DCM, THF and the like.

The compounds of Formula XXV upon treatment with acids for example but not limited to HBr, HI, BBr$_3$ or AlCl$_3$ in a suitable solvent such as DCM, DCE, Chloroform, Acetic acid and the like can furnish compounds of Formula XXVI. Alternately, the compounds of Formula XXV can be subjected to deprotection of OPG$^2$ and the resulting free hydroxyl group can be converted to a leaving group to furnish compounds of Formula XXVI. Such deprotection conditions include oxidative deprotection using reagents for example but not limited to DDQ, CAN or a combination of OsO$_4$, NaIO$_4$ and NMO in a suitable solvent. Alternately, deprotection can also be done by metal catalyzed reactions involving Pd(PPh$_3$)$_4$ or Pd/C in presence of alkali base or 1,3-dimethyl barbituric acid in a suitable solvent such as but not limited to THF, methanol or DME. The free hydroxy group of thus obtained intermediate can be converted to a leaving group such as but not limited to triflate, tosylate, mesylate, halogen or phosphate by treating with trifluoromethanesulfonic anhydride, p-toluenesulfonylchloride, methanesulfonyl chloride or (OEt)$_2$POCl, PBr$_3$, SOCl$_2$ or a combination of CBr$_4$/PPh$_3$ optionally in presence of a suitable base for example, but not limited to pyridine, NMM, DIPEA or triethyl amine in a suitable solvent such as DCM, THF, ACN and the like to furnish the compounds of Formula XXVI.

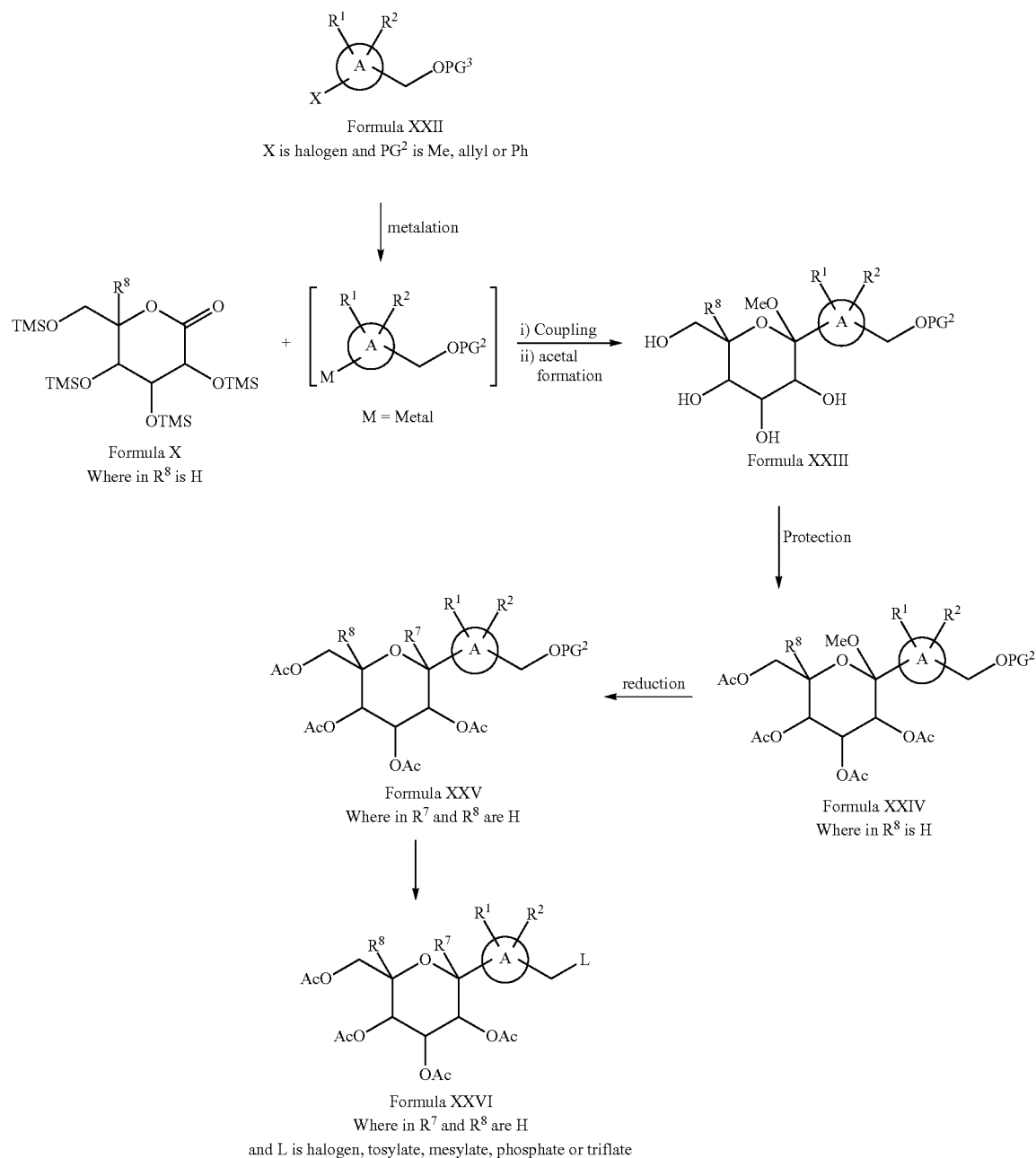

Scheme 8

Formula XXII
X is halogen and PG² is Me, allyl or Ph

Formula X
Where in R⁸ is H

Formula XXIII

Formula XXIV
Where in R⁸ is H

Formula XXV
Where in R⁷ and R⁸ are H

Formula XXVI
Where in R⁷ and R⁸ are H
and L is halogen, tosylate, mesylate, phosphate or triflate The compounds of the Formula XXXII where in $R^8$ and $R^7$ are methylene and oxygen respectively which are linked through a bond, can be prepared from compounds of Formula XXIII by following Scheme 9. Compounds of Formula XXIII can be converted to compounds of Formula XXVII by protecting all free hydroxyl groups with TMS by using TMSCl in the presence of a base such as but not limited to NMM, $NEt_3$, DIPEA, imidazole or pyridine in a suitable solvent for example THF, DCM or ACN and the like. Thus obtained tetra silyl intermediate can be treated with silyl deprotecting agents for example but not limited to $K_2CO_3$, TBAF, a combination of KF-crownether, NBS, $SiF_4$, $BF_3.Et_2O$, $CF_3SO_3SiMe_3$ or aqueous acids in a suitable solvent such as MeOH, DCM, THF, ACN and the like, under tuned conditions to achieve selective deprotection of primary hydroxyl group. Thus obtained compounds of Formula XXVII can be oxidized to compounds of Formula XXVIII by using various reagents in combination with DMSO and a base such as but not limited to $NEt_3$, DIPEA or collidine. The reagents that can be used for this transformation are for example but not limited to $Ac_2O$, oxalyl chloride, DCC, $SO_3$.Py.

Alternately, the compounds of Formula XXVII can be oxidized to compounds of Formula XXVIII by using TPAP, TPAP and NMO, TEMPO and NaOCl, $MnO_2$, $BaMnO_4$, $CrO_3$.Py, PCC, PDC, Dess-Martin periodinane, O-iodoxybenzoic acid, oxone and the like. The compounds of Formula XXVIII can be converted to compounds of Formula XXIX by using formaldehyde or paraformaldehyde in the presence of a suitable base such as but not limited to NaOH, KOH, $K_2CO_3$ or Potassium Phosphate in a suitable solvent such as dioxane, methanol, ethanol, THF or a combination thereof. Alternately, the compounds of Formula XXIII can be converted into compounds of Formula XXIX by selective conversion of primary hydroxyl group in to a leaving group such as but not limited to tosylate, mesylate or Iodo by treatment with p-tolenesulfonyl chloride, methane sulfonyl chloride or iodine in combination with a suitable base such as pyridine, lutidine, collidine, $Na_2CO_3$ or $K_2CO_3$ optionally in presence of a solvent such as but not limited to DCM, DCE, DMF or DMSO. Thus obtained intermediate is heated at temperatures ranging from 60 to 180° C. in pyridine, lutidine or collidine under Kornblum oxidation conditions to afford the aldehyde intermediate. This aldehyde can be treated with formaldehyde or paraformaldehyde in the presence of a suitable base such as but not limited to NaOEt, NaOH, KOH, $K_2CO_3$ or Potassium Phosphate in a suitable solvent such as dioxane, methanol, ethanol, THF or a combination thereof to furnish compounds of formula XXIX.

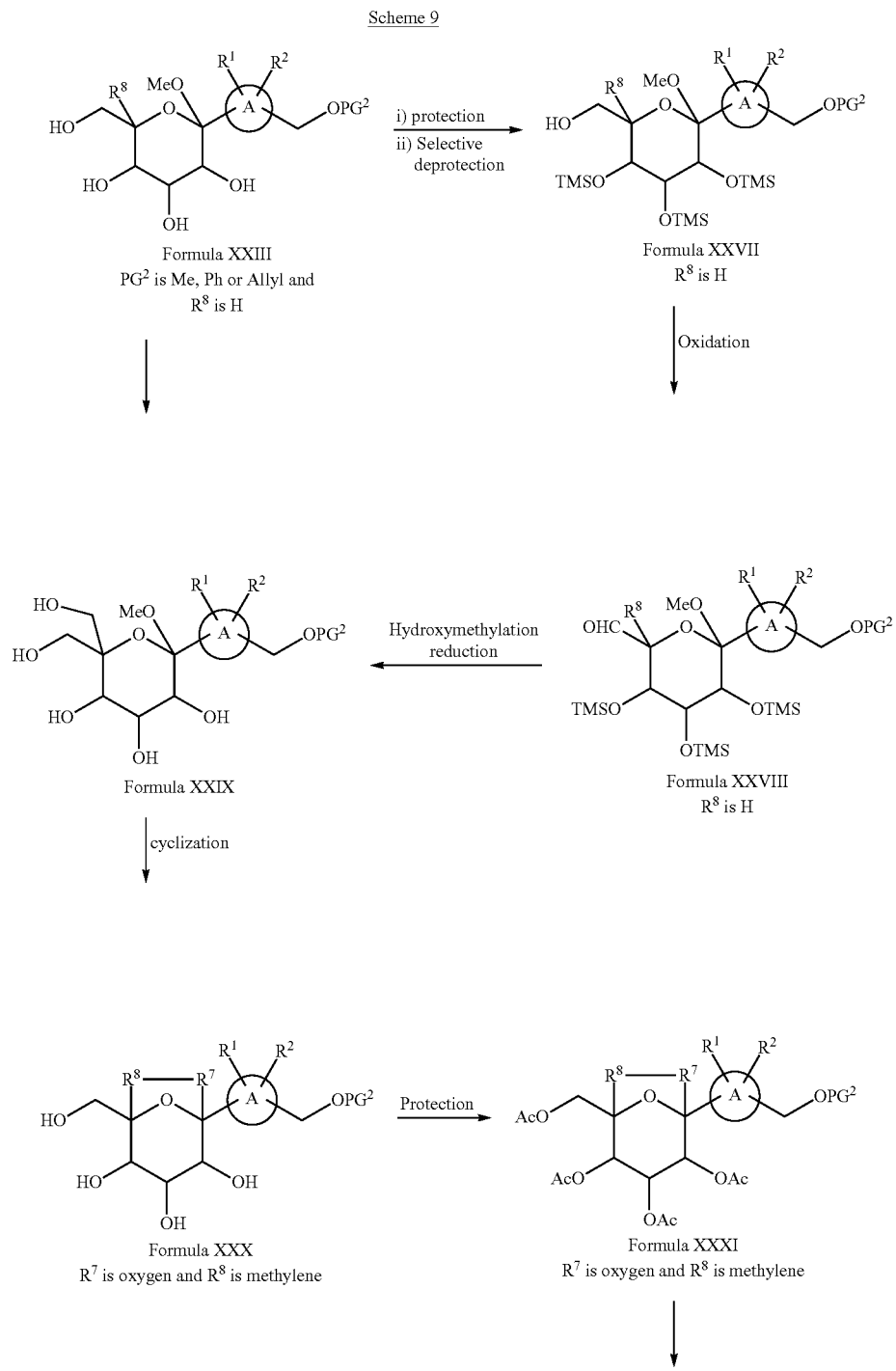

Scheme 9

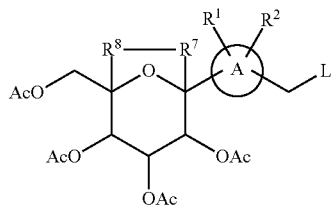

Formula XXXII
$R^7$ is oxygen and $R^8$ is methylene;
L is leaving group like
halogen, mesylate, tosylate,
phosphate or triflate The compounds of Formula XXIX can be treated with a suitable acid such as methanesulfonic acid, trifluoroacetic acid, HCl, $H_2SO_4$ and the like in a suitable solvent for example but not limited to DCM, DCE or acetic acid to furnish the compounds of Formula XXX. The compounds of Formula XXX can be protected with acetyl groups by using acetic anhydride or acetyl chloride in the presence of a suitable base such as but not limited to $NEt_3$, DIPEA, pyridine, DMAP, $K_2CO_3$ or NaOH in a suitable solvent for example DCM, DMF, THF, acetone or a combination there of to furnish compounds of Formula XXXI. The compounds of Formula XXXI upon treatment with acids for example but not limited to HBr, HI, $BBr_3$ or $AlCl_3$ in a suitable solvent such as DCM, DCE, chloroform, acetic acid and the like can furnish compounds of Formula XXXII. Alternately, the compounds of Formula XXXI can be subjected to deprotection of $OPG^2$ and the resulting free hydroxyl group can be converted to a leaving group to furnish compounds of Formula XXXII. Such deprotection conditions include oxidative deprotection using reagents for example but not limited to DDQ, CAN or a combination of $OsO_4$, $NaIO_4$ and NMO in a suitable solvent. Alternately, deprotection can also be done by metal catalyzed reactions involving $Pd(PPh_3)_4$ or Pd/C in presence of alkali base or 1,3-dimethyl barbituric acid in a suitable solvent such as but not limited to THF, methanol or DME. The free hydroxy group of thus obtained intermediate can be converted to a leaving group such as but not limited to triflate, tosylate, mesylate, halogen or phosphate by treating with trifluoromethane sulfonic anhydride, p-toluenesulfonylchloride, methanesulfonyl chloride or $(OEt)_2POCl$, $PBr_3$, $SOCl_2$ or a combination of $CBr_4/PPh_3$ optionally in presence of a suitable base for example, but not limited to pyridine, NMM, DIPEA or triethyl amine in a suitable solvent such as DCM, THF, ACN and the like to furnish the compounds of Formula XXXII.

Scheme 10

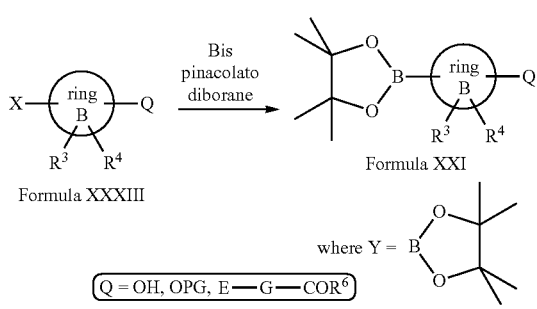

The compounds of Formula XXI can be prepared by following Scheme 10. The compound of Formula XXXIII where in X is halogen can be reacted with bis-pinacolatodiborane in the presence of a catalyst such as $Pd(dppf)Cl_2$, $Pd_2(dba)_3$, $Pd(OAc)_2$, $Pd(PPh_3)_4$ or $PdCl_2$ in presence of KOAc, NaOAc or a phosphate buffer in a suitable solvent such as but not limited to dioxane, THF, toluene or DCE to obtain compounds of Formula XXI.

It is understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations. The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. The salts may be prepared during the final isolation and purification of the compounds or separately by making basic or acidic addition salts. Representative salts of basic compounds of the present invention can be prepared by reacting free base form of the compound with a suitable acid, including, but not limited to acetate, trifluoroacetate, adipate, citrate, aspartate, benzoate, benzenesulphonate, bisulfate, besylate, butyrate, camphorsulphonate, difluconate, hemisulfate, heptanoate, formate, fumarate, lactate, maleate, methanesulfonate, naphthylsulfonate, nicotinate, oxalate, picrate, pivalate, succinate, tartrate, tirchloracetat, glutamate, p-toluenesulphonate, hydrochloric, hydrobromic, sulphuric, phosphoric and the like. Representative salts of acidic compounds of the present invention can be prepared by reacting free acid form of the compound with a suitable base, including, but not limited to ammonium, calcium, magnesium, potassium, sodium salts, salts of primary, secondary and tertiary amines, substituted amines including naturally occurring ones e.g., arginine, betaine, caffeine, choline, glucamine, glucosamine, histidine, lysine, morpholine, piperazine, piperidine, purine, triethylamine and the like. Compounds of the present invention that contain a carboxylic acid (—COOH) or alcohol group, their pharmaceutically acceptable esters of carboxylic acids such as methyl, ethyl and the like, or acyl derivatives of alcohols such as acetate and the like, can be employed. Compounds of the present invention that comprise basic nitrogen atom may be quaternized with alkyl halides, alkyl sulfates and the like. Such salts permit the preparation of both water soluble and oil soluble compounds of the present invention. It should be recognized that the free base or free acid forms will typically differ from their respective salt forms somewhat in physical properties such as solubility in polar solvents, but otherwise the salts are equivalent to their respective free forms for the purpose of the invention.

The "pharmaceutically acceptable solvates" refer to solvates with water (i.e., hydrates) or pharmaceutically acceptable solvents, for example, ethanol and the like.

The invention also encompasses "prodrugs" of the compounds of the present invention which upon in-vivo administration undergo cleavage by metabolic processes before becoming active pharmacological substances. In general such prodrugs are derivatives of functional group of a compound of the invention which are readily convertible in vivo into the compound of the invention. Conventional procedures for the selection and preparation of suitable prodrug derivatives are described, for example, in "Targeted prodrug design to optimize drug delivery", AAPS PharmaSci (2000), 2(1), E6. In certain cases, the prodrug itself can also have biological activity in the disease area.

Preferably, the invention encompasses Oxygen prodrugs (O-prodrugs) of the compounds of the present invention which upon in-vivo administration undergo chemical conversion by metabolic processes before becoming active pharmacological substances. In general such O-prodrugs can be represented in general by O-alkyl ethers (methyl, ethyl, substituted alkyl ethers like methoxymethyl, ethoxyethyl and the like), O-allyl ethers, O-benzyl ethers, O-substituted benzyl ethers, O-esters (e.g., formate, benzoyl, acetate, benzoate and the like), or carbonates (e.g., methyl, methoxymethyl and the like) and the like.

The invention also encompasses active "metabolites" of the compound of the present invention. An active metabolite is an active derivative of a SGLT-2 inhibitor produced when the SGLT-2 inhibitor is metabolized.

The present invention includes all pharmaceutically acceptable isotopically-labeled compounds of Formula I wherein one or more atoms are replaced by atoms having the same atomic number, but an atomic mass or mass number different from the atomic mass or mass number usually found in nature. Examples of isotopes suitable for inclusion in the compounds of the present invention comprises isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Isotopically-labeled compounds of Formula I can generally be prepared by conventional techniques known to those skilled in the art or by processes analogous to those described in the accompanying examples and schemes using an appropriate isotopically-labeled reagent in place of the non-labeled reagent previously employed.

The present invention also includes all the intermediate complexes of the compounds of Formula I, which are active by themselves or can be readily converted to compounds having inhibitory effect on sodium-dependent glucose cotransporter (SGLT), preferably SGLT-2.

The present invention also provides pharmaceutical compositions, comprising compounds of general Formula I or their pharmaceutically acceptable analogs, derivatives, tautomeric forms, isomers, polymorphs, prodrugs, metabolites, salts or solvates thereof together with one or more pharmaceutically acceptable carriers comprising excipients and auxiliaries, which facilitate processing of the active compound into preparations, which can be used pharmaceutically. The pharmaceutical compositions may be in the forms normally employed, such as tablets, capsules, powders, syrups, solutions, suspensions, emulsions, pills, granules, suppositories, pellets, depot formulations and the like, may contain flavourants, sweeteners etc in suitable solid or liquid carriers or diluents, or in suitable sterile media to form injectable solutions or suspensions. Such compositions typically contain from 0.1 to 99.9% by weight of active compound, the remainder of the composition being pharmaceutically acceptable carriers, diluents or solvents.

The pharmaceutical compositions of the present invention can be manufactured by the processes well known in the art, for example, by means of conventional mixing, dissolving, dry granulation, wet granulation, dragee-making, levigating, emulsifying, encapsulating, entrapping, lyophilizing processes or spray drying. The compounds or the pharmaceutical compositions comprising such compounds of the present invention may be administered in the form of any pharmaceutical formulation. The pharmaceutical formulation will depend upon the nature of the active compound and its route of administration. Any route of administration may be used, for example oral, buccal, pulmonary, topical, parenteral (including subcutaneous, intramuscular and intravenous), transdermal, ocular (ophthalmic), by inhalation, intranasal, transmucosal, implant or rectal administration. Preferably the compounds of the present invention are administered orally, parenterally or topically.

An embodiment of the present invention provides a therapeutically effective amount of a compound of Formula I, or its pharmaceutically acceptable derivatives, tautomeric forms, stereoisomers, polymorphs, prodrugs, metabolites, salts or solvates thereof, for use as a pharmaceutical composition.

In another embodiment, the amount of the novel compounds having the Formula I according to the present invention to be incorporated into the pharmaceutical compositions of the present invention can vary over a wide range depending on known factors such as, for example, the disorder to be treated, the severity of the disorder, the patient's body weight, the dosage form, the chosen route of administration and the number of administration per day. Typically, the amount of the compound of Formula I in the pharmaceutical compositions of the present invention will range from approximately 0.01 mg to about 5000 mg. In an embodiment, the daily dose of composition comprising the novel compounds having the Formula I is in the range of about 0.01 mg/kg to about 100 mg/kg based on the body weight of the subject in need thereof which may be administered as a single or multiple doses.

In an embodiment, the novel compounds having the Formula I according to the present invention are particularly useful for the treatment of disease(s) or disorder(s), which are chronic or acute in nature, which favorably respond to or are alleviated by the novel compounds having the Formula I or compositions comprising them. The compositions comprising the novel compounds having the Formula I are useful prophylactically or therapeutically depending upon the pathological condition intended to be prevented or treated respectively.

In one embodiment compounds of the present invention are useful in the prophylaxis, amelioration and/or treatment of one or more condition(s)/disease(s)/disorder(s), in a subject in need thereof.

In another embodiment compounds of the present invention are useful in the prophylaxis, amelioration and/or treatment of one or more condition(s)/disease(s)/disorder(s), which may be regulated or normalized via inhibition of Sodium Glucose Cotransporters (SGLT).

The compounds of the present invention possess activity as selective inhibitors of SGLT-2 and are therefore useful for the prophylaxis, amelioration and/or treatment of variety of diseases, disorders and conditions, including, but not limited to, diabetes (including Type I and Type II), Metabolic Syndrome or 'Syndrome X' including impaired glucose tolerance, insulin resistance, metabolic acidosis or ketosis, disorders of food intake, satiety disorders, obesity, hyperinsulinemia, dyslipidemia (including hyperlipidemia, hypertriglyceridemia, hypercholesterolemia, low HDL levels, high LDL levels), hypertension associated with metabolic disorders, congestive heart failure, edema, hyperuricemia, gout, wound healing and tissue ischemia.

The compounds of the present invention can also be used for the prophylaxis, amelioration and/or treatment of the diseases, disorders and conditions collectively referenced to as "diabetic complications" which include both acute complications and chronic complications. Examples of "acute complications" include hyperglycemia (e.g., ketoacidosis), infections (e.g., skin, soft tissue, biliary system, respiratory system and urinary tract infections), etc. Examples of "chronic complications" include microangiopathy (e.g., nephropathy, retinopathy), arteriosclerosis (e.g., atherosclerosis, heart infarction, brain infarction, lower extremity arterial occlusion), neuropathy (e.g, sensory nerves, motor nerves, autonomic nerves), foot gangrene, etc. Major diabetic complications include diabetic retinopathy, diabetic nephropathy and diabetic neuropathy.

All of the various forms and sub-forms of the disorders mentioned herein are contemplated as part of the present invention.

A further embodiment of the present invention is the use of a compound of Formula I for the manufacture of a medicament for the prophylaxis, amelioration and/or treatment of one or more condition(s)/disease(s)/disorder(s) involving SGLT-2 inhibition in a subject in need thereof.

Another embodiment of the present invention is the compound of Formula I or pharmaceutically acceptable derivatives, tautomeric forms, stereoisomers, polymorphs, prodrugs, metabolites, salts or solvates thereof, for use as a medicament.

In still another embodiment of the present invention is the compound of Formula I for use as a medicament for the prophylaxis, amelioration and/or treatment of one or more condition(s)/disease(s)/disorder(s) involving SGLT-2 inhibition, in a subject in need thereof preferably a mammal including a human.

Another embodiment of the present invention provides methods for the prophylaxis, amelioration and/or treatment of one or more condition(s)/disease(s)/disorder(s) involving SGLT-2 inhibition in a subject in need thereof that comprises administering a therapeutically effective amount of compound of Formula I.

In still another embodiment of the present invention is provided use of the dosage form compositions comprising the novel compounds of Formula I for the treatment of one or more condition(s)/disease(s)/disorder(s) involving SGLT-2 inhibition which comprises administrating to a subject in need thereof a pharmaceutically effective amount of the composition.

An embodiment of the present invention relates to methods of using the compounds of Formula I of the present invention or compositions comprising the compounds of Formula I for the prophylaxis, amelioration and/or treatment of any one or more condition(s)/disease(s)/disorder(s) involving SGLT-2 inhibition, which comprises administering to a subject in need thereof the compounds of Formula I or compositions comprising a pharmaceutically effective amount of the compounds of Formula I.

Another embodiment of the present invention provides a therapeutically effective amount of compound of Formula I, or pharmaceutically acceptable derivatives, tautomeric forms, stereoisomers, polymorphs, prodrugs, metabolites, salts or solvates thereof, for use in prophylaxis, amelioration and/or treatment of one or more condition(s)/disease(s)/disorder(s) involving SGLT-2 inhibition, in a subject in need thereof.

In yet another embodiment, the compounds or their pharmaceutically acceptable salts according to the present invention are useful in the treatment of the aforementioned diseases, disorders and conditions in combination with at least one other therapeutic agent. The compounds of the present invention may be used in combination with one or more other therapeutic agents in the treatment, prevention, suppression or amelioration of diseases or conditions for which compounds of the present invention or other therapeutic agents may have utility, where the combination of drugs together are safer or more effective than either drug alone.

Other therapeutic agents suitable for combination with the compounds of the present invention include, but are not limited to, known therapeutic agents useful in the treatment of the aforementioned disorders including: anti-diabetic agents; agents for prevention of complications of diabetes; anti-hyperglycemic agents; hypolipidemic/lipid lowering agents; anti-obesity agents; anti-hypertensive agents, anti-platelet agents, anti-atherosclerotic agents, anti-inflammatory agents, uricosuric agents, anti-TNF agent or c-AMP raising agents and appetite suppressants.

It is believed that the use of the compounds of the present invention in combination with at least one or more of the aforementioned other therapeutic agents may provide results greater than that possible from each of these medicaments alone or greater than the combined additive effects produced by these medicaments. The present compounds and the other therapeutic agents may be administered in the same dosage form or in a separate dosage form by same or different administration route, in dosages and regimens as generally known in the art. Those agents which potentiate the therapeutic effect of SGLT-2 inhibitors according to the invention may allow the dosage to be reduced.

Examples of suitable anti-diabetic agents for use in combination with the compounds of the present invention include but are not limited to (a) other SGLT inhibitors; (b) insulin sensitizers including (i) PPAR γ agonists such as thiozolidinediones or glitazones (e.g. pioglitazone, rosiglitazone and the like), PPAR δ agonists, PPAR α agonists such as fenofibric acid derivatives (gemfibrozil, clofibrate, fenofibrate and bezafibrate), PPARpan agonists, PPAR γ/δ agonists, PPAR α/γ dual agonists, PPAR α/δ dual agonists, PPAR γ antagonists, PPAR α/γ modulators and PPAR α/γ/δ modulators, (ii) biguanides such as metformin and phenformin, and (iii) protein tyrosine phosphatase-1B (PTP-1B) inhibitors; (c) insulin or insulin mimetics; (d) sulfonylureas and other insulin secretagogues, such as tolbutamide, chlorpropamide, tolazamide, glyburide (glibenclamide), glipizide, gliclazide, gliquidone, glimepiride, and meglitinides, such as repaglinide, mitiglinide, nateglinde and the like; (e) glucose absorption inhibitors like alpha.-glucosidase inhibitors (such as acarbose, voglibose and miglitol); (f) glucagon receptor antagonists; (g) GLP-1, GLP-1 mimetics such as exendin-4 or amylin and GLP-1 receptor agonists (h) GIP and GIP mimetics (i) PACAP, PACAP mimetics, and PACAP receptor agonists; (j) AMPK activators; (k) 11β-HSD inhibitors; (l) DPP-IV inhibitors such as Sitagliptin (Merck), Vildagliptin (Novartis); (m) inhibitors of glucose-6-phosphate, fructose-1,6-biphosphate, glycogen phosphorylase, phosphoenol pyruvate carboxykinase, glycogen synthase kinase, aminopeptidase-N or pyruvate dehydrokinase; (n) glucokinase activators (GKAs); (O) RXR modulators; (p) GPR40 agonists/antagonists, GPR119 agonists or GPR120 agonists; (q) alpha2-antagonists; (r) IBAT inhibitors, HM74a/HM74 agonists, glucocorticoid antagonists, amylin receptor agonists, peptide YY hormone, PEPCK inhibitor, somatotropin release inhibiting factor, CPT-1 inhibitor, insulin receptor kinase stimulants, tripeptidyl peptidase II inhibitors, hepatic gluconeogenesis inhibitors or carboxypeptidase inhibitor.

Examples of suitable agents to be used in combination with the compounds of the present invention, for treatment or prevention of complications of diabetes include but are not limited to GABA-receptor antagonists, Na-channel blockers (e.g. mexiletine hydrochloride, oxacarbazepine or the like), γ-aminobutyric acid receptor antagonists (e.g. topiramat or the like), protein-kinase C inhibitors (e.g. midostaurin or the like), advanced glycation end product inhibitors (e.g. pyridoxamine or the like), transcript factor NF-κB inhibitors (e.g. dexlipotam or the like), lipid peroxide inhibitors (e.g. tirilazad mesylate or the like), α-linked-acid-dipeptidase inhibitors, carnitine derivatives (e.g. levacecamine, levocarnitine or the like), insulin like growth factor-I, platelet-derived growth factor, platelet-derived growth factor analogues, epidermal growth factor, nerve growth factor, biclomol, sulodexide or aldose reductase inhibitors (e.g. ascorbyl gamolenate, tolrestat, epalrestat or the like).

Examples of suitable hypolipidemic/lipid lowering agents for use in combination with the compounds of the present invention include but are not limited to (a) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) bile acid sequestrants (cholestyramine, colestipol, and dialkylaminoalkyl derivatives of a cross-linked dextran), (iii) nicotinyl alcohol, nicotinic acid or a salt thereof, (iv) PPAR agonists as described herein, (v) inhibitors of cholesterol absorption, such as beta-sitosterol and ezetimibe, (vi) acyl CoA cholesterol acyltransferase inhibitors, such as avasimibe, and (vii) anti-oxidants, such as probucol; (b) ileal bile acid transporter inhibitors; (c) HDL raising compounds such as CETP inhibitors or ABC1 regulators (d) lipoxygenase inhibitors; (e) ACAT inhibitors such as avasimibe; (f) fibric acid derivatives i.e. fibrates (e.g. bezafibrate, fenofibrate, gemfibrozil, clofibrate, ciprofibrate, clinofibrate or the like); (g) MTP inhibitors; (h) squalene synthetase inhibitors and squalene epoxidase inhibitors; (i) upregulators of LDL receptor activity; (j) serum cholesterol lowering agents; (k) thyroid hormone receptor agonists (sodium liothyronine, sodium levothyroxine or the like); (l) carnitine palmitoyltransferase inhibitors (etomoxir or the like); (m) probcol and microsomal triglyceride transfer protein inhibitors.

Examples of suitable anti-obesity compounds for use in combination with the compounds of the present invention include but are not limited to (a) fenfluramine, dexfenfluramine, phenteimine, tetrahydrolipostatin, and the like; (b) neuropeptide $Y_1$ or $Y_5$ antagonists; (c) CB-1 receptor inverse agonists and antagonists; (d) $β_3$ adrenergic receptor agonists; (e) melanocortin receptor agonists, in particular melanocortin-4 receptor agonists; (f) ghrelin antagonists; (g) melanin-concentrating hormone (MCH) receptor antagonists; (h) lipase inhibitors like orlistat; (i) serotonin (and dopamine) reuptake inhibitors like sibutramine, topiramate or axokine; (j) thyroid hormone receptor beta drugs; (k) anorectic agents like dexamphetamine, phentermine or mazindol; (l) Leptin analogs.

Examples of suitable appetite suppressants for use in combination with the compounds of the present invention include but are not limited to (a) monoamine reuptake inhibitors; (b) dopamine agonists; (c) leptin analogues; (d) α-melanocyte stimulating hormone; (e) enterostatin agonists; (f) CCK-A agonists; (g) corticotropin releasing hormone; (h) somatostatin; (i) brain-derived neurotrophic factor; (j) orexin receptor agonists.

Examples of suitable anti-hypertensive agents for use in combination with the compounds of the present invention include but are not limited to (a) vasopeptidase inhibitors like Neutral endopeptidase (neprilysin) inhibitors and/or ACE (angiotensin-converting enzyme) inhibitors or dual NEP/ACE inhibitors (enalapril, lisinopril, captopril, quinapril, trandolapril, fosinpril, benazepril, ramipril, enalaprilat, moexipril or perindopril and the like) and/or PKC inhibitors; (b) beta blockers (like metoprolol, propranolol, atenolol, carvedilol or sotalol) and calcium channel blocker (like amlodipine, diltiazem, nifedipine, verapamil or nicardipine); (c) Angiotensin-II receptor blockers (like losartan, candesartan, irbesartan, valsartan, telmisartan or eprosartan); (d) Renin inhibitors e.g., aliskiren; (e) alpha blockers like terazosin, doxazosin or prasozin; (f) diuretics such as hydrochlorothiazide, torasemide, furosemide, spironolactone or indapamide; (g) thrombocyte aggregation inhibitors; (h) endothelin-converting enzyme inhibitors and endothelin receptor antagonists; (i) vasodilating antihypertensive agents e.g. indapamide, todralazine, hydralazine, budralazine or the like; (j) centrally acting antihypertensive agents e.g. reserpine; (k) $α_2$-adrenoreceptor agonists e.g. clonidine, methyldopa, moxonidine or the like.

Examples of suitable anti-inflammatory agents for use in combination with the compounds of the present invention include but are not limited to aspirin, non-steroidal anti-inflammatory drugs, glucocorticoids, azulfidine, and selective cyclooxygenase-2 inhibitors.

Examples of suitable anti-platelet agents for use in combination with the compounds of the present invention include but are not limited to abciximab, ticlopidine, eptifibatide, dipyridamole, aspirin, anagrelide, tirofiban or clopidogrel.

Examples of suitable agents to be used in combination with the compounds of the present invention, for the treatment or prevention of hyperuricemia or gout include but are not limited to (a) uric acid synthesis inhibitors e.g. allopurinol, oxypurinol or the like; (b) uricosuric agents e.g. benzbromarone, probenecid or the like; (c) urinary alkanizers e.g. sodium hydrogen carbonate, potassium citrate or the like.

EXAMPLES

The invention is explained in detail in the following examples which are given solely for the purpose of illustration only and therefore should not be construed to limit the scope of the invention. Those skilled in the art will readily understand that known variations of the conditions and processes of the following preparative procedures can be used to prepare the compounds of the present invention.

All solvents used in reactions were freshly distilled. Solvents were dried prior to use wherever necessary by standard methods (Perrin, D. D.; Armarego, W. L. F. Purification of Laboratory Chemicals, Pergamon Press: Oxford, 1988). Mass spectra (MS) were obtained by electron spray ionization (ESI) eV using Applied biosystem 4000 Q TRAP. $^1$H NMR were recorded on Bruker 400 MHz Avance II NMR spectrometer in CDCl$_3$ (until and unless specified). Chemical shifts are reported as δ values in parts per million (ppm), relative to TMS as internal standard. All Coupling constant (J) values are given in Hz.

Abbreviations

The following abbreviations are employed in the examples and elsewhere herein:

| | | | |
|---|---|---|---|
| $^1$H NMR | proton nuclear magnetic resonance | ACN | Acetonitrile |
| AcOH | acetic acid | Ac$_2$O | acetic anhydride |
| C | centigrade | CAN | ceric ammonium nitrate |
| CDCl$_3$ | deuterated chloroform | CD$_3$OD | deuterated methanol |
| d | doublet | dd | doublet of doublet |
| DCC | N,N'-Dicyclohexylcarbodiimide | DCE | 1,2-Dichloroethane |
| DCM | dichloromethane | DDQ | dichloro dicyano quinine |
| DIPEA | N,N-Diisopropylethylamine | DMAP | 4-Dimethylaminopyridine |
| DMF | dimethylformamide | DMSO | Dimethylsulfoxide |
| ESIMS | electron spray ionization mass spectroscopy | g | gram(s) |
| h | hour(s) | Hz | Hertz |
| $^i$PrMgCl | isopropyl magnesium chloride | J | coupling constant |
| L | liter | LDA | lithium di-isopropyl amide |
| LiHMDS | lithium hexamethyldisilazide | m | Multiplet |
| M | molar | MeOH | Methanol |
| mesylate | methane sulfonate | mg | Milligram |
| MHz | mega hertz | min | Minutes |
| mmol | millimoles | mpk | milligram/kilogram |
| NaOAc | sodium acetate | NBS | N-bromosuccinimide |
| $^n$BuLi | n-butyl lithium | nM | nano molar |
| NMM | N-methylmorpholine | NMO | N-methylmorpholine-N-oxide |
| NMP | N-methyl-2-pyrrolidone | NMR | nuclear magnetic resonance |
| OAc | acetoxy | P(OEt)$_2$OCl | diethoxyphosphoryl chloride |
| PCy$_3$ | tricyclohexylphosphine | PCC | pyridinium chlorochromate |
| PDC | pyridinium dichromate | Pd$_2$(dba)$_3$ | tris(dibenzylideneacetone)dipalladium(0) |
| Pet. Ether | petroleum ether | Pd(dppf)Cl$_2$ | [1,1'-Bis (diphenylphosphino) ferrocene] dichloropalladium(II) |
| pH | potential hydrogen | PG | protecting group |
| PPh$_3$ | triphenylphosphine | PMB | p-methoxybenzyl |
| Py | pyridine | pTSA | p-toluenesulfonic acid |
| r.t. | room temperature | q | Quartet |
| t | triplet | s | Singlet |
| TBDMS | tert-butyldimethylsilyl | TBAF | tetra-n-butylammonium fluoride |
| TEMPO | (2,2,6,6-Tetramethylpiperidin-1-yl)oxyl | $^t$BuLi | tert-butyl lithium |
| THF | tetrahydrofuran | TFA | trifluoro acetic acid |
| TMS | tetramethylsilane | TLC | thin layer chromatography |
| tosylate | p-toluenesulfonate | TMSCl | trimethylsilyl chloride |
| triflate | trifluoromethanesulfonate | TPAP | tetrapropylammonium perruthenate |
| μg | microgram | UGE | urinary glucose excretion |

Intermediate 1

Preparation of (2R,3R,4R,5S,6S)-2-(acetoxymethyl)-6-(3-(bromomethyl)-4-chlorophenyl)tetrahydro-2H-pyran-3,4,5-triyl triacetate Step 1: Preparation of (5-bromo-2-chlorophenyl)methanol 5-bromo-2-chlorobenzoic acid (20 g, 84.92 mmol) in dry THF (50 mL) was added to a solution of sodium borohydride (8 g, 212.34 mmol) in dry THF (128 mL) in 15 min at r.t. To the resulting reaction mixture a solution of Iodine (26.85 g, 106.15 mmol) in dry THF (170 mL) was added in another 15 min. Stirring was continued till the Iodine color disappeared after which the reaction mixture was heated to reflux temperature for 18 h. After completion of the reaction as confirmed by TLC, volatiles were evaporated in vacuo. The residue obtained was dissolved in ethyl acetate (200 mL), washed with a saturated solution of NaHSO$_3$ (200 mL) and brine (200 mL) successively. The organic layer was dried over Na$_2$SO$_4$ and concentrated in vacuo to afford crude product which was purified by column chromatography (silica gel, 3:7 Ethyl acetate:Pet. Ether) to afford the title compound (18.3 g, 97%).

ESIMS (m/z): 222.8 (M+1)

Step 2: Preparation of 4-bromo-1-chloro-2-(chloromethyl)benzene (5-Bromo-2-chlorophenyl)methanol (11.37 g, 51.22 mmol) was taken in aqueous HCl (35%) (1.54 L) and stirred at 70-80° C. for 18 h. After completion of the reaction as confirmed by TLC, the reaction mixture was cooled in an ice bath. The precipitate obtained was collected over Buchner filter, washed with water (2×500 mL) and dried in vacuo to afford the title compound (12.2 g, 99%).

ESIMS (m/z): 240.7 (M+1)

Step 3: Preparation of 4-bromo-1-chloro-2-(phenoxymethyl)benzene

To a solution of 4-bromo-1-chloro-2-(chloromethyl)benzene (12.2 g, 50.85 mmol) and phenol (4.79 g, 50.85 mmol) in DMF (102 mL) under nitrogen atmosphere, K$_2$CO$_3$ was added (35.14 g, 254.25 mmol). The resulting mixture was stirred at r.t. for 18 h. After completion of the reaction as confirmed by TLC, the reaction mixture was passed through celite plug and the filtrate was evaporated. The residue obtained was dissolved in ethyl acetate (100 mL) and washed with water (2×100 mL) and brine (2×100 mL) successively. The organic layer was dried over $Na_2SO_4$ and concentrated in vacuo to afford crude product which was purified by column chromatography (silica gel, 1:9 Ethyl acetate:Pet. Ether) to afford the title compound (14.7 g, 97.3%).

ESIMS (m/z): 297.6 (M−1)

Step 4: Preparation of (2S,3R,4S,5S,6R)-2-(4-chloro-3-(phenoxymethyl)phenyl)-6-(hydroxymethyl)-2-methoxytetrahydro-2H-pyran-3,4,5-triol To a solution of 4-bromo-1-chloro-2-(phenoxymethyl)benzene (10.0 g, 33.61 mmol) in dry Toluene (200 mL) and dry THF (100 L), "BuLi (33.61 mL, 53.77 mmol, 1.6 M solution in pentane) was added at −78° C. The reaction mixture was stirred at the same temperature for 15 min. A solution of (3R,4S,5R,6R)-3,4,5-tris((trimethylsilyl)oxy)-6-(((trimethylsilyl)oxy)methyl)tetrahydro-2H-pyran-2-one (18.80 g, 40.33 mmol, prepared following the procedure given in US20070049537) in dry toluene (170 mL) was introduced into it at the same temperature and stirred for another 3 h. After completion of the reaction as confirmed by TLC, water (90 mL) was added at the same temperature and allowed to stir while raising the temperature to r.t. The reaction mixture was diluted with ethyl acetate (200 mL) and the separated aqueous layer was discarded. The organic layer was dried over $Na_2SO_4$ and concentrated in vacuo. The residue obtained was dissolved in methanol (90 mL) and methanesulfonic acid (2.15 mL, 33.56 mmol) was added at 0° C. The temperature was raised to r.t. gradually and stirred for 16 h. The reaction was quenched by the addition of $NEt_3$ (14 mL, 50.5 mmol) at 0° C. The volatiles were evaporated in vacuo and the residue obtained was dissolved in ethyl acetate (500 mL), washed with water (200 mL) and brine (200 mL) successively. The organic layer was dried over anhydrous $Na_2SO_4$ and volatiles were evaporated in vacuo. The residue obtained was purified by column chromatography (silica gel, 1:9 MeOH:DCM) to provide title compound (9.5 g, 68.8%).

ESIMS (m/z): 410.0 (M−1)

Step 5: Preparation of (2S,3R,4S,5R,6R)-6-(acetoxymethyl)-2-(4-chloro-3-(phenoxymethyl)phenyl)-2-methoxytetrahydro-2H-pyran-3,4,5-triyl triacetate To a solution of (2S,3R,4S,5S,6R)-2-(4-chloro-3-(phenoxymethyl)phenyl)-6-(hydroxymethyl)-2-methoxytetrahydro-2H-pyran-3,4,5-triol (9.5 g, 23.12 mmol), DIPEA (28.86 ml, 168.80 mmol) and DMAP (1.02 g, 8.32 mmol) in THF (87 mL) was added acetic anhydride (17.73 mL, 187.59 mmol) at 0° C. The reaction was stirred at r.t. for 2 h. After the completion of reaction as confirmed by TLC, the reaction mixture was diluted with ethyl acetate (100 mL) and washed with 10% aqueous HCl (50 mL), saturated $NaHCO_3$ (50 mL) and water (50 mL) successively. The organic layer was dried over $Na_2SO_4$ and concentrated in vacuo to afford crude product which was purified by column chromatography (silica gel, 3:7 Ethyl acetate:Pet. Ether) to afford the title compound (12.18 g, 91%).

ESIMS (m/z): 596.2 (M+18)

Step 6: Preparation of (2R,3R,4R,5S,6S)-2-(acetoxymethyl)-6-(4-chloro-3-(phenoxymethyl)phenyl)tetrahydro-2H-pyran-3,4,5-triyl triacetate To a solution of (2S,3R,4S,5R,6R)-6-(acetoxymethyl)-2-(4-chloro-3-(phenoxymethyl)phenyl)-2-methoxytetrahydro-2H-pyran-3,4,5-triyl triacetate (12.00 g, 20.73 mmol), triethylsilane (10.46 mL, 65.51 mmol) and water (373 mg, 20.73 mmol) in ACN (62.18 mL) was added $BF_3.Et_2O$ (5.21 mL, 41.46 mmol) at 0° C. The reaction was stirred at r.t. for 18 h. After the completion of reaction as confirmed by TLC, the reaction mixture was diluted with ethyl acetate (100 mL) and washed with saturated $NaHCO_3$ (50 mL). The organic layer was dried over $Na_2SO_4$ and concentrated in vacuo to afford crude product which was purified by column chromatography (silica gel, 3:7 Ethyl acetate:Pet. Ether) to afford the title compound (10.58 g, 93%).

ESIMS (m/z): 571.7 (M+23)

Step 7: Preparation of (2R,3R,4R,5S,6S)-2-(acetoxymethyl)-6-(3-(bromomethyl)-4-chlorophenyl)tetrahydro-2H-pyran-3,4,5-triyl triacetate To a solution of (2R,3R,4R,5S,6S)-2-(acetoxymethyl)-6-(4-chloro-3-(phenoxymethyl)phenyl)tetrahydro-2H-pyran-3,4,5-triyl triacetate (10.00 g, 18.22 mmol) in acetic acid (31 mL) was added HBr in acetic acid (45.55 mL, 2.5 mL/mmol) and the reaction mixture was stirred at r.t. for 18 h. After the completion of reaction as confirmed by TLC, the reaction mixture was neutralized by the addition of saturated $K_2CO_3$ at 0° C. and extracted with ethyl acetate (2×50 mL). The combined organic layers were washed with water (50 mL) and brine (50 mL) successively. The organic layer was dried over $Na_2SO_4$ and concentrated in vacuo to afford crude product which was purified by column chromatography (silica gel, 3:7 Ethyl acetate:Pet. Ether) to afford the title compound (7.9 g, 81%).

ESIMS (m/z): 554.6 (M+18)

Intermediate 2

Preparation of (1R,2S,3S,4R,5S)-1-(acetoxymethyl)-5-(3-(bromomethyl)-4-chlorophenyl)-6,8-dioxabicyclo[3.2.1]octane-2,3,4-triyl triacetate Step 1: Preparation of ((2R,3R,4S,5R,6S)-6-(4-chloro-3-(phenoxymethyl)phenyl)-6-methoxy-3,4,5-tris((trimethylsilyl)oxy)tetrahydro-2H-pyran-2-yl)methanol To a solution of (2S,3R,4S,5S,6R)-2-(4-chloro-3-(phenoxymethyl)phenyl)-6-(hydroxymethyl)-2-methoxytetrahydro-2H-pyran-3,4,5-triol (25 g, 60.90 mmol), (obtained in step 4 of Intermediate 1) in DCM (180 mL) under nitrogen atmosphere, was added imidazole (41.46 g, 609.01 mmol) and chlorotrimethyl silane (46.37 mL, 365.4 mmol) at 0° C. The reaction mixture was warmed to room temperature and stirred for 2 h. After the completion of the reaction as confirmed by TLC, water (50 mL) was added. The organic layer was separated, dried over $Na_2SO_4$ and concentrated to afford crude (((2S,3R,4S,5R,6R)-2-(4-chloro-3-(phenoxymethyl)phenyl)-2-methoxy-6-((((trimethylsilyl)oxy)methyl)tetrahydro-2H-pyran-3,4,5-triyl)tris(oxy))tris(trimethylsilane) (42.35 g, 100%) as a solid which was used for next step without any purification.

To the above suspension in MeOH (150 mL) under nitrogen atmosphere, was added potassium carbonate (168.08 mg, 1.218 mmol) at 0° C. The reaction mixture was warmed to room temperature and stirred for 2 h. After completion of the reaction as confirmed by TLC, the reaction mixture was cooled to 0° C. and quenched with a solution of acetic acid (0.07 ml, 1.217 mmol) in methanol (2 mL) followed by addition of water (200 mL). The crude compound was extracted with diethyl ether (500 mL). The organic layer was separated, washed with water (200 mL), dried over $Na_2SO_4$, concentrated in vacuo to afford crude product which was purified by column chromatography (silica gel, 4:6 Ethyl acetate:Pet. Ether) to afford the title compound (29 g, 76%) as a white solid.

ESIMS (m/z): 626.3 (M+)

Step 2: Preparation of (2S,3R,4S,5R,6S)-6-(4-chloro-3-(phenoxymethyl)phenyl)-6-methoxy-3,4,5-tris((trimethylsilyl)oxy)tetrahydro-2H-pyran-2-carbaldehyde To a suspension of ((2R,3R,4S,5R,6S)-6-(4-chloro-3-(phenoxymethyl)phenyl)-6-methoxy-3,4, 5-tris((trimethylsilyl)oxy)tetrahydro-2H-pyran-2-yl)methanol (23.0 g, 36.7 mmol) in DMSO (250 mL) was added DCM (20 mL) to make a clear solution. The solution was cooled to 0° C. followed by addition of triethyl amine (122.4 ml, 881.0 mmol) and sulphur trioxide pyridine complex (87.5 g, 550.6 mmol). The reaction mixture was stirred at 0 to 10° C. for 3 h under nitrogen atmosphere. After completion of the reaction as confirmed by TLC, the crude compound was extracted with diethyl ether (1 L). The organic layer was separated, washed with water (2×500 mL), dried over $Na_2SO_4$, concentrated in vacuo to afford crude title compound (22.9 g, 100%) as a viscous oil which was used for next step without any purification.

Step 3: Preparation of (2S,3R,4S,5S)-2-(4-chloro-3-(phenoxymethyl)phenyl)-6,6-bis(hydroxymethyl)-2-methoxytetrahydro-2H-pyran-3,4,5-triol To a solution of (2S,3R,4S,5R,6S)-6-(4-chloro-3-(phenoxymethyl)phenyl)-6-methoxy-3,4,5-tris((trimethylsilyl) oxy)tetrahydro-2H-pyran-2-carbaldehyde (22.9 g, 36.7 mmol) in EtOH (92 mL) under nitrogen atmosphere, was added para-formaldehyde (33.0 g, 1.1 mol) at 55° C. followed by addition of 21% NaOEt in ethanol (23.12 g NaOEt/110 mL EtOH). The reaction mixture was heated at 55° C. overnight. After the completion of the reaction as confirmed by TLC, ethanol was evaporated. The crude compound was extracted with ethyl acetate (700 mL) followed by washing with sodium bisulphate solution (68.67 g, 660.6 mmol) in water (458.7 mL). The organic layer was separated, dried over $Na_2SO_4$ and concentrated in vacuo to afford crude compound, which was purified by column chromatography (silica gel, 6:4 MeOH:DCM) to obtain the compound as a white solid (12 g).

Step 4: Preparation of (3S,4S,5R,6S)-2,2-bis(acetoxymethyl)-6-(4-chloro-3-(phenoxymethyl)phenyl)-6-methoxytetrahydro-2H-pyran-3,4,5-triyl triacetate To a solution of the compound obtained above (12 g, 27.24 mmol) in THF (55 mL) under nitrogen atmosphere, was added DMAP (1.19 g, 9.80 mmol), DIPEA (34.24 mL, 199.68 mmol) and acetic anhydride (20.6 mL, 217.93 mmol) at 0° C. The reaction mixture was warmed to r.t. and stirred for 2 h. After the completion of reaction as confirmed by TLC, the crude compound was extracted with ethyl acetate (500 mL). The organic layer was washed with 10% HCl (200 mL), separated, dried over $Na_2SO_4$ and concentrated in vacuo to afford crude compound which was purified by column chromatography (silica gel, 2.5:7.5 Ethyl acetate:Pet. Ether) to afford (3S,4S,5R,6S)-2,2-bis(acetoxymethyl)-6-(4-chloro-3-(phenoxymethyl)phenyl)-6-methoxytetrahydro-2H-pyran-3,4,5-triyl triacetate (12.0 g, 50%) as a white solid.

ESIMS (m/z): 673.9 (M+23), 651.7 (M+1)

Step 5: Preparation of (2S,3R,4S,5S)-2-(4-chloro-3-(phenoxymethyl)phenyl)-6,6-bis(hydroxymethyl)-2-methoxytetrahydro-2H-pyran-3,4,5-triol To a solution of (3S,4S,5R,6S)-2,2-bis(acetoxymethyl)-6-(4-chloro-3-(phenoxymethyl)phenyl)-6-methoxytetrahydro-2H-pyran-3,4,5-triyl triacetate (12.0 g, 18.44 mmol) obtained above, in THF (60.8 mL), methanol (90 mL) and water (30.6 mL), was added lithium hydroxide monohydrate (929 mg, 22.12 mmol) at 0° C. The reaction mixture was stirred at r.t. for 1 h. After the completion of the reaction as confirmed by TLC, volatiles were evaporated in vacuo and the compound was extracted with ethyl acetate (500 mL). The organic layer was separated, washed with water (100 mL), dried over $Na_2SO_4$ and concentrated to afford the title compound (8.12 g, 100%) as a white solid.

ESIMS (m/z): 463.8 (M+23)

Step 6: Preparation of (1S,2S,3S,4R,5S)-5-(4-chloro-3-(phenoxymethyl)phenyl)-1-(hydroxymethyl)-6,8-dioxabicyclo[3.2.1]octane-2,3,4-triol To a solution of (2S,3R,4S,5S)-2-(4-chloro-3-(phenoxymethyl)phenyl)-6,6-bis(hydroxymethyl)-2-Methoxytetrahydro-2H-pyran-3,4,5-triol (8.0 g, 18.16 mmol) in DCM (45 mL) under nitrogen atmosphere was added TFA (4.17 mL, 54.4 mmol) at 0° C. The reaction mixture was warmed to r.t. and stirred for 3-4 h. After the completion of the reaction as confirmed by TLC, the reaction mixture was quenched with saturated solution of sodium bicarbonate. The crude compound was extracted with DCM (100 mL). The organic layer was separated, dried over $Na_2SO_4$ and concentrated in vacuo to afford crude title compound (7.45 g, 100%) as a white solid which was used without further purification for the next step.

ESIMS (m/z): 409.3 (M+1), 431.4 (M+23)

Step 7: Preparation of (1R,2S,3S,4R,5S)-1-(acetoxymethyl)-5-(4-chloro-3-(phenoxymethyl)phenyl)-6,8-dioxabicyclo[3.2.1]octane-2,3,4-triyl triacetate To a solution of (1S,2S,3S,4R,5S)-5-(4-chloro-3-(phenoxymethyl)phenyl)-1-(hydroxymethyl)-6,8-dioxabicyclo [3.2.1]octane-2,3,4-triol (7.0 g, 17.13 mmol) in THF (80 mL) under nitrogen atmosphere, was added DMAP (750.4 mg, 6.13 mmol), DIPEA (22.3 mL, 125.16 mmol) and acetic anhydride (12.88 mL, 136.58 mmol) at 0° C. The reaction mixture was warmed to r.t. and stirred for 2 h. After the completion of reaction as confirmed by TLC, the crude compound was extracted with ethyl acetate (600 mL). The organic layer was washed with 10% HCl (200 mL), separated, dried over $Na_2SO_4$ and concentrated in vacuo to afford crude compound which was purified by column chromatography (silica gel, 2:8 Ethyl acetate:Pet. Ether) to afford the title compound (8.2 g, 82%) as a white solid.

ESIMS (m/z): 601.9 (M+23)

Step 8: Preparation of (1R,2S,3S,4R,5S)-1-(acetoxymethyl)-5-(3-(bromomethyl)-4-chlorophenyl)-6,8-dioxabicyclo[3.2.1]octane-2,3,4-triyl triacetate To a solution of (1R,2S,3S,4R,5S)-1-(acetoxymethyl)-5-(4-chloro-3-(phenoxymethyl)phenyl)-6,8-dioxabicyclo

[3.2.1]octane-2,3,4-triyl triacetate (5.5 g, 9.54 mmol), in acetic acid (23.62 mL) under nitrogen atmosphere, was added 37% HBr/AcOH (47.7 mL). The reaction mixture was stirred at r.t. for 3 h. After the completion of the reaction as confirmed by TLC, the reaction mixture was cooled to 0° C. and quenched very slowly with saturated solution of potassium carbonate until effervescence ceases. The crude compound was extracted with ethyl acetate (2×300 mL). The organic layer was separated, dried over Na$_2$SO$_4$ and concentrated in vacuo to afford crude compound which was purified by column chromatography (silica gel, 3:7 Ethyl acetate:Pet ether) to afford the title compound (4.28 g, 79%) as a white solid.

Example 1

Preparation of 2-(4-(2-chloro-5-((2S,3R,4R,5S,6R)-3,4,5-trihydroxy-6-(hydroxymethyl)tetrahydro-2H-pyran-2-yl)benzyl)phenoxy)acetaldehyde O-methyl oxime

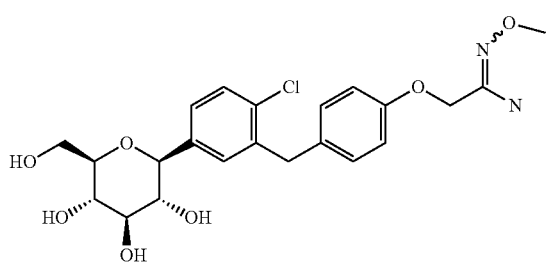 [SMILES: CON=C(N)COc1ccc(Cc2cc([C@@H]3O[C@H](CO)[C@@H](O)[C@H](O)[C@H]3O)ccc2Cl)cc1]

Step 1: Preparation of (2S,3R,4S,5S,6R)-2-(3-(4-((tert-butyldimethylsilyl)oxy)benzyl)-4-chlorophenyl)-6-(hydroxymethyl)-2-methoxytetrahydro-2H-pyran-3,4,5-triol To a solution of (4-(5-bromo-2-chlorobenzyl)phenoxy)(tert-butyl)dimethylsilane (67.0 g, 0.163 mol, prepared by following the procedure given in US20070049537) in dry THF (1.0 L), $^t$BuLi (228 mL, 0.342 mol, 1.6 M solution in pentane) was added at −78° C. The reaction mixture was stirred at the same temperature for 30 mM. A solution of (3R,4S,5R,6R)-3,4,5-tris((trimethylsilyl)oxy)-6-(((trimethylsilyl)oxy)methyl)tetrahydro-2H-pyran-2-one (77.8 g, 0.167 mol, prepared following the procedure given in US20070049537) in dry THF (272 mL) was introduced into it at the same temperature and stirred for another 4 h. A solution of methanesulfonic acid (18.35 mL, 0.283 mol) in methanol (586 mL) was added and the temperature was raised to r.t. gradually and stirred for 16 h. The reaction was quenched by the addition of saturated aqueous solution of NaHCO$_3$ (500 mL) and volatiles were evaporated in vacuo. The residue obtained was dissolved in ethylacetate (1 L), washed with water (500 mL) and brine (500 mL) successively. The organic layer was dried over anhydrous Na$_2$SO$_4$ and volatiles were evaporated in vacuo. The residue was purified by column chromatography (silica gel, 1:9 MeOH:DCM) to provide title compound (47.37 g, 55.4%) as off-white solid.

ESIMS (m/z): 524.2 (M−1)

Step 2: Preparation of (2S,3R,4S,5R,6R)-6-(acetoxymethyl)-2-(3-(4-((tert-butyldimethylsilyl)oxy)benzyl)-4-chlorophenyl)-2-methoxytetrahydro-2H-pyran-3,4,5-triyl triacetate To a solution of (2S,3R,4S,5S,6R)-2-(3-(4-((tert-butyldimethylsilyl)oxy)benzyl)-4-chlorophenyl)-6-(hydroxymethyl)-2-methoxytetrahydro-2H-pyran-3,4,5-triol (47.0 g, 0.090 mol) in dry THF (286 mL), DIPEA (114.28 mL, 0.660 mol) and DMAP (3.94 g, 0.032 mol) were added. Acetic anhydride (55 mL, 0.582 mol) was added to the resulting solution at 0° C. The reaction mixture was stirred at r.t. for 2 h. Ethylacetate (1 L) was added to the reaction mixture, washed it with 2% HCl solution (2×100 mL), water (500 mL) and brine (500 mL) successively. The organic layer was dried over anhydrous Na$_2$SO$_4$ and volatiles were evaporated in vacuo. The residue obtained was purified by column chromatography (silica gel, 1:9 MeOH:DCM) to provide title compound (53.9 g, 86.93%) as off-white solid.

ESIMS (m/z): 715.0 (M+23)

Step 3: Preparation of (2R,3R,4R,5S,6S)-2-(Acetoxymethyl)-6-(4-chloro-3-(4-hydroxybenzyl)phenyl)tetrahydro-2H-pyran-3,4,5-triyl triacetate To a solution of (2S,3R,4S,5R,6R)-6-(acetoxymethyl)-2-(3-(4-((tert-butyldimethylsilyl)oxy)benzyl)-4-chlorophenyl)-2-methoxytetrahydro-2H-pyran-3,4,5-triyl triacetate (44.0 g, 0.064 mol) in acetonitrile (200 mL), water (1.15 mL, 0.064 mol), triethylsilane (32.45 mL, 0.203 mol) and borontrifluoroetherate (15.94 mL, 0.127 mol) were added at 10° C. The resulting mixture was stirred at r.t. for 16 h. Additional amounts of triethylsilane (3.25 mL, 0.020 mol) and borontrifluoroetherate (1.59 mL, 0.013 mol) were added at 10° C. and heated at 30° C. for 6 h. Ethylacetate (1 L) was added to the reaction mixture, washed it with saturated NaHCO$_3$ solution (2×500 mL), water (500 mL) and brine (500 mL) successively. The organic layer was dried over anhydrous Na$_2$SO$_4$ and volatiles were evaporated in vacuo. The residue obtained was purified by column chromatography (silica gel, 4:6 Ethyl acetate:Pet.Ether) to provide title compound (30 g, 86.27%) as off-white solid.

ESIMS (m/z): 548.2 (M−1)

Step 4: Preparation of (2-bromoethoxy)(tert-butyl)dimethylsilane

To a solution of 2-bromoethanol (3.4 mL, 48.34 mmol) in dry DCM (25 mL) imidazole (9.86 g, 143 mmol) and tert-butylchlorodimethylsilane (10.9 gm, 72.52 mmol) were added at 0° C. The reaction mixture was stirred at r.t. for 24 h. After completion of reaction, as confirmed by TLC, the reaction mixture was diluted with ethylacetate (350 mL) and washed with water (4×20 mL). The organic layer was dried over anhydrous Na$_2$SO$_4$ and volatiles were evaporated in vacuo. The residue obtained was purified by column chromatography (silica gel, 0.2:9.8 Ethyl acetate:Pet. Ether) to afford title compound (204 mg, 77.5%) as liquid.

ESIMS (m/z): 239.1 (M+1).

Step 5: Preparation of (2R,3R,4R,5S,6S)-2-(acetoxymethyl)-6-(3-(4-(2-((tert-butyldimethyl silyl)oxy)ethoxy)benzyl)-4-chlorophenyl)tetrahydro-2H-pyran-3,4,5-triyl triacetate To a solution of (2R,3R,4R,5S,6S)-2-(Acetoxymethyl)-6-(4-chloro-3-(4-hydroxybenzyl)phenyl)tetrahydro-2H-pyran-3,4,5-triyl triacetate (500 mg, 0.91 mmol) in dry DMF (10 mL), was added (2-bromoethoxy)(tert-butyl)dimethylsilane (436 mg, 1.82 mmol) and cesium carbonate (890 mg, 2.73 mmol). The reaction was stirred at r.t. for 36 h. After completion of reaction, as confirmed by TLC, the reaction mixture was diluted with ethyl acetate (150 mL) and washed with water (3×10 mL). The organic layer was dried over anhydrous Na₂SO₄ and volatiles were evaporated in vacuo. The residue obtained was purified by column chromatography (silica gel, 4:6 Acetone:Pet. Ether) to afford title compound (392 mg, 60.85%) as white solid.

ESIMS (m/z): 707.9 (M+1)

Step 6: Preparation of (2R,3R,4R,5S,6S)-2-(acetoxymethyl)-6-(4-chloro-3-(4-(2-hydroxy ethoxy) benzyl)phenyl)tetrahydro-2H-pyran-3,4,5-triyl triacetate To a solution of (2R,3R,4R,5S,6S)-2-(acetoxymethyl)-6-(3-(4-(2-((tert-butyldimethylsilyl)oxy)ethoxy)benzyl)-4-chlorophenyl)tetrahydro-2H-pyran-3,4,5-triyltriacetate (2.59 g, 3.66 mmol) in THF:Water (1:1, 36 mL) was added acetic acid (54 mL) at 0° C. The reaction mixture was stirred at r.t. for 24 h. After completion of reaction, as confirmed by TLC, the reaction mixture was evaporated in vacuo and the residue obtained was purified by column chromatography (silica gel, 4:6 Ethyl acetate:Pet. Ether) to afford title compound (1.8 g, 82%).

ESIMS (m/z): 593.7 (M+1)

Step 7: Preparation of (2R,3R,4R,5S,6S)-2-(acetoxymethyl)-6-(4-chloro-3-(4-(2-oxoethoxy)benzyl) phenyl)tetrahydro-2H-pyran-3,4,5-triyl triacetate Oxalyl chloride (0.042 mL, 0.51 mmol) was added to a solution of DMSO (0.071 mL, 1.01 mmol) in dry DCM (0.5 mL) at −78° C. under nitrogen atmosphere. The reaction mixture was stirred for 5 min. at the same temperature and then a solution of (2R,3R,4R,5S,6S)-2-(acetoxymethyl)-6-(4-chloro-3-(4-(2-hydroxyethoxy)benzyl)phenyl)tetrahydro-2H-pyran-3,4,5-triyl triacetate (150 mg, 0.25 mmol), in dry DCM (2 mL) was added. The reaction mixture was stirred at the same temperature for 1 h. NEt₃ (0.211 mL, 1.518 mmol) was added and the reaction mixture was allowed to come to r.t. The crude compound was extracted with DCM (20 mL). The organic layer was separated, washed with water (15 mL). The combined organic layers were dried over Na₂SO₄ and concentrated in vacuo to afford the title compound which was used as such in next step.

ESIMS (m/z): 612.9 (M+23)

Step 8: Preparation of (2R,3R,4R,5S,6S)-2-(acetoxymethyl)-6-(4-chloro-3-(4-(2-(methoxy imino) ethoxy)benzyl)phenyl)tetrahydro-2H-pyran-3,4,5-triyl triacetate To a solution of (2R,3R,4R,5S,6S)-2-(acetoxymethyl)-6-(4-chloro-3-(4-(2-oxoethoxy)benzyl)phenyl)tetrahydro-2H-pyran-3,4,5-triyl triacetate (145 mg, 0.25 mmol), in ethanol (10 mL) under nitrogen atmosphere, were added pyridine (0.099 mL, 1.28 mmol), sodium acetate (201.3 mg, 2.45 mmol) and O-methylhydroxylamine hydrochloride (102 mg, 1.22 mmol). The reaction mixture was refluxed for 5 h. After completion of the reaction as confirmed by TLC, the solvent was evaporated. The crude compound was extracted with ethyl acetate (50 mL). The organic layer was separated, washed with water (2×10 mL), dried over Na₂SO₄ and concentrated in vacuo to afford crude product which was purified by column chromatography (silica gel, 1.8:8.2 Acetone:Pet. Ether) to afford title compound (100 mg, 64.4%).

ESIMS (m/z): 620.6 (M+1)

Step 9: Preparation of 2-(4-(2-chloro-5-((2S,3R,4R,5S,6R)-3,4,5-trihydroxy-6-(hydroxymethyl)tetrahydro-2H-pyran-2-yl)benzyl)phenoxy)acetaldehyde O-methyl oxime To a solution of (2R,3R,4R,5S,6S)-2-(acetoxymethyl)-6-(4-chloro-3-(4-(2-(methoxyimino)ethoxy)benzyl)phenyl) tetrahydro-2H-pyran-3,4,5-triyl triacetate (100 mg, 0.161 mmol) in THF (0.6 mL), methanol (0.8 mL) and water (0.3 mL) was added lithium hydroxide monohydrate (13.5 mg, 0.322 mmol) at 0° C. The reaction was stirred at r.t. for 1 h. Volatiles were evaporated in vacuo and the residue obtained was purified by column chromatography (silica gel, 1:9 MeOH:DCM) to provide the title compound (70 mg, 96.2%) as white solid.

ESIMS (m/z): 452.8 (M+1)

¹H NMR (400 MHz, CD₃OD): δ 3.25-3.46 (m, 4H), 3.67 (dd, J=12 and 5.2 Hz, 1H), 3.82-3.89 (m, 4H), 3.98-4.09 (m, 3H), 4.56 (d, J=5.6 Hz, 1H), 4.77 (d, J=3.6 Hz, 1H), 6.79-6.85 (m, 2H), 6.89 and 7.51 (two t, J=3.6 and 5.6 Hz, 1H, isomers), 7.09-7.12 (m, 2H), 7.25-7.34 (m, 3H), 7.30 (d, J=1.9 Hz, 1H)

Example 2

Preparation of 2-(4-(2-chloro-5-((2S,3R,4R,5S,6S)-3,4,5-trihydroxy-6-methoxytetrahydro-2H-pyran-2-yl)benzyl)phenoxy)acetaldehyde O-methyl oxime

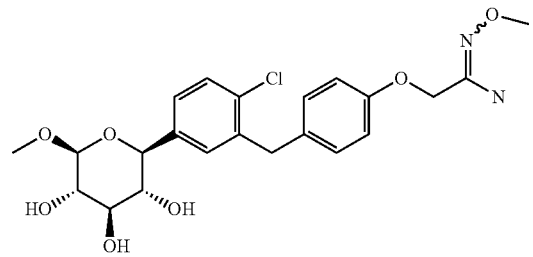

Step 1: Preparation of ((3aS,5S,6R,6aS)-6-((tert-butyldimethylsilyl)oxy)-2,2-dimethyl tetrahydrofuro[2,3-d][1,3]dioxol-5-yl)(3-(4-((tert-butyldimethylsilyl)oxy)benzyl)-4-chlorophenyl)methanol A solution of (4-(5-bromo-2-chlorobenzyl)phenoxy)(tert-butyl)dimethylsilane (14.2 g, 34.57 mmol, prepared following the procedure given in US20070049537) in dry THF (90 mL) was cooled to −78° C. and ⁿBuLi (30.7 mL, 46.05 mmol, 1.5 M solution in hexane) was added drop wise while stirring and stirring was continued for further 30 min. A solution of (3aS,5R,6R,6aS)-6-((tert-butyldimethylsilyl)oxy)-2,2-dimethyltetrahydrofuro[2,3-d][1,3]dioxole-5-carbaldehyde (7.0 g, 23.05 mmol, prepared according to the procedure given in NUCLEOSIDE, NUCLOETIDES & NUCLEIC ACIDS, 20(4-7), 649-652 (2001)) in dry THF (13 mL) was added dropwise to the reaction mixture and stirred at the same temperature for 2 h. Reaction temperature was raised slowly to 0° C. and then stirred at r.t. for 16 h. After completion of reaction, as confirmed by TLC, reaction mixture was quenched by the addition of saturated NH₄Cl solution and extracted with ethyl acetate (3×300 mL). The combined organic layers were dried over Na₂SO₄ and the volatiles were evaporated in vacuo. The residue obtained was purified by column chromatography (silica gel, 0.2:9.8 Acetone:Pet. Ether) to afford the title compound (3.66 g, 25%)

ESIMS (m/z): 657.0 (M+23)

Step 2: Preparation of (3S,4R,5S,6S)-6-(3-(4-acetoxybenzyl)-4-chlorophenyl)tetrahydro-2H-pyran-2,3,4,5-tetrayl tetraacetate A solution of ((3aS,5S,6R,6aS)-6-((tert-butyldimethylsilyl)oxy)-2,2-dimethyl tetrahydrofuro[2,3-d][1,3]dioxol-5-yl)(3-(4-((tert-butyldimethylsilyl)oxy)benzyl)-4-chlorophenyl)methanol (3.66 g, 5.76 mmol) in 3:2 acetic acid and water (30 mL) was refluxed at 110° C. for 22 h. After completion of reaction, as confirmed by TLC, reaction mixture was concentrated in vacuo. Toluene (3×10 mL) was added and distilled and the residue obtained was dissolved in pyridine (15 mL). The resulting mixture was treated with acetic anhydride (4.0 mL, 42.62 mmol) at r.t. for 16 h. After completion of reaction, as confirmed by TLC, water was added and stirred for 1 h. The reaction mixture was diluted with ethyl acetate (100 mL) and washed with saturated NaHCO$_3$ solution (50 mL) and brine (50 mL). The organic layers were dried over Na$_2$SO$_4$ and the volatiles were removed in vacuo. The residue obtained was purified by column chromatography (silica gel, 2:8 Acetone:Pet.Ether) to afford the title compound (2.03 g, 70%)

ESIMS (m/z): 598.3 (M+23)

Step 3: Preparation of (3S,4R,5S,6S)-2-bromo-6-(4-chloro-3-(4-hydroxybenzyl)phenyl)tetrahydro-2H-pyran-3,4,5-triyl triacetate To (3S,4R,5S,6S)-6-(3-(4-acetoxybenzyl)-4-chlorophenyl)tetrahydro-2H-pyran-2,3,4,5-tetrayl tetraacetate (2.03 g, 4.03 mmol) a 33% solution of HBr in AcOH (6 mL) was added at r.t. and stirred for 0.1 h. The reaction mixture was diluted with DCM (20 mL) and stirred for 30 min. Water was added to the resulting mixture and stirred for another 1 h. It was diluted with DCM (50 mL), washed with water (50 mL), saturated NaHCO$_3$ solution (50 mL) and brine (50 mL). The organic layer was dried over Na$_2$SO$_4$ and the volatiles were evaporated in vacuo to afford the title compound (2.02 g, 90%)

ESIMS (m/z): 554.9 (M+1)

Step 4: Preparation of (2S,3S,4R,5S,6S)-2-(4-chloro-3-(4-hydroxybenzyl)phenyl)-6-methoxytetrahydro-2H-pyran-3,4,5-triyl triacetate To a solution of (3S,4R,5S,6S)-2-bromo-6-(4-chloro-3-(4-hydroxybenzyl)phenyl)tetrahydro-2H-pyran-3,4,5-triyl triacetate (2.02 g, 3.62 mmol) in methanol (15 mL) was added ZnO (294.5 mg, 3.62 mmol) at 60° C. The reaction mixture was stirred at 60° C. for 1 h. After completion of reaction, as confirmed by TLC, reaction mixture was passed through sintered funnel to remove the solids. The filterate was evaporated in vacuo and the residue obtained was purified by column chromatography (silica gel, 2:8 Acetone:Pet. Ether) to afford title compound (1.1 g, 65%)

ESIMS (m/z): 506.0 (M−1)

Step 5: Preparation of (2S,3S,4R,5S,6S)-2-(3-(4-(2-(tert-butyldimethylsilyloxy)ethoxy)benzyl)-4-chlorophenyl)-6-methoxytetrahydro-2H-pyran-3,4,5-triyl triacetate To a solution of (2S,3S,4R,5S,6S)-2-(4-chloro-3-(4-hydroxybenzyl)phenyl)-6-methoxytetrahydro-2H-pyran-3,4,5-triyl triacetate (300 mg, 0.593 mmol) in dry DMF (6 mL), was added (2-bromoethoxy)(tert-butyl)dimethylsilane (423 mg, 1.78 mmol) and cesium carbonate (578 mg, 1.78 mmol). The reaction mixture was stirred at r.t. for 36 h. After completion of reaction, as confirmed by TLC, the reaction mixture was diluted with ethylacetate (100 mL) and washed with water (3×10 mL). The organic layer was dried over anhydrous Na$_2$SO$_4$ and volatiles were evaporated in vacuo. The residue obtained was purified by column chromatography (silica gel, 2:8 Ethyl acetate:Pet. Ether) to afford title compound (310 mg, 78.8%) as white solid.

ESIMS (m/z): 684.8 (M+23)

Step 6: Preparation of (2S,3S,4R,5S,6S)-2-(4-chloro-3-(4-(2-hydroxyethoxy)benzyl)phenyl)-6-methoxytetrahydro-2H-pyran-3,4,5-triyl triacetate To a solution (2S,3S,4R,5S,6S)-2-(3-(4-(2-(tert-butyldimethylsilyloxy)ethoxy)benzyl)-4-chlorophenyl)-6-methoxytetrahydro-2H-pyran-3,4,5-triyl triacetate (300 mg, 0.452 mmol) in THF:Water (1:1, 3.2 mL) was added acetic acid (4.8 mL) at 0° C. The reaction mixture was stirred at r.t. for 24 h. After completion of reaction, as confirmed by TLC, the reaction mixture was evaporated in vacuo and the residue obtained was purified by column chromatography (silica gel, 1:1 Ethyl acetate:Pet. Ether) to afford title compound (176 mg, 80%).

ESIMS (m/z): 571.5 (M+23)

Step 7: Preparation of (2S,3S,4R,5S,6S)-2-(4-chloro-3-(4-(2-oxoethoxy)benzyl)phenyl)-6-methoxytetrahydro-2H-pyran-3,4,5-triyl triacetate Oxalyl chloride (0.068 mL, 0.80 mmol) was added to a solution of DMSO (0.113 mL, 1.60 mmol) in dry DCM (1 mL) at −78° C. under nitrogen atmosphere. The reaction mixture was stirred for 5 min. at the same temperature and then a solution of (2S,3S,4R,5S,6S)-2-(4-chloro-3-(4-(2-hydroxyethoxy)benzyl)phenyl)-6-methoxytetrahydro-2H-pyran-3,4,5-triyl triacetate (220 mg, 0.403 mmol), in dry DCM (3 mL) was added. The reaction mixture was stirred at the same temperature for 1 h. NEt$_3$ (0.334 mL, 2.40 mmol) was added and the reaction mixture was allowed to come to r.t. The crude compound was extracted with DCM (30 mL). The organic layer was separated, washed with water (15 mL). The combined organic layers were dried over Na$_2$SO$_4$ and concentrated in vacuo to afford the title compound, which was used as such in next step.

ESIMS (m/z): 564.9 (M+18)

Step 8: Preparation of (2S,3S,4R,5S,6S)-2-(4-chloro-3-(4-(2-(methoxyimino)ethoxy)benzyl)phenyl)-6-methoxytetrahydro-2H-pyran-3,4,5-triyl triacetate To a solution of (2S,3S,4R,5S,6S)-2-(4-chloro-3-(4-(2-oxoethoxy)benzyl)phenyl)-6-methoxytetrahydro-2H-pyran-3,4,5-triyl triacetate (200 mg, 0.365 mmol), in ethanol (10 mL) under nitrogen atmosphere, were added pyridine (0.147 mL, 1.82 mmol), sodium acetate (299 mg, 3.65 mmol) and O-methylhydroxylamine hydrochloride (152 mg, 1.82 mmol). The reaction mixture was refluxed for 5 h. After completion of the reaction as confirmed by TLC, the solvent was evaporated. The crude compound was extracted with ethyl acetate (3×25 mL). The organic layer was separated, washed with water (3×10 mL), dried over Na$_2$SO$_4$ and concentrated in vacuo to afford crude product which was purified by column chromatography (silica gel, 1.5:8.5 Acetone:Pet. Ether) to afford the title compound (140 mg, 64.5%).

ESIMS (m/z): 578.5 (M+1)

Step 9: Preparation of 2-(4-(2-chloro-5-((2S,3R,4R, 5S,6S)-3,4,5-trihydroxy-6-methoxytetrahydro-2H-pyran-2-yl)benzyl)phenoxy)acetaldehyde O-methyl oxime To a solution of (2S,3S,4R,5S,6S)-2-(4-chloro-3-(4-(2-(methoxyimino)ethoxy)benzyl)phenyl)-6-methoxytetrahydro-2H-pyran-3,4,5-triyl triacetate (140 mg, 0.242 mmol) in THF (0.8 mL), methanol (1.2 mL) and water (0.4 mL) was added lithium hydroxide monohydrate (20.4 mg, 0.485 mmol) at 0° C. The reaction was stirred at r.t. for 1 h. Volatiles were evaporated in vacuo and the residue obtained was purified by column chromatography (silica gel, 1:9 MeOH:DCM) to provide the title compound (70 mg, 64.2%).

ESIMS (m/z): 452.9 (M+1)

$^1$H NMR (400 MHz, CD$_3$OD): δ 3.27-3.29 (m, 2H), 3.38-3.45 (m, 1H), 3.46 (s, 3H), 3.82 and 3.89 (two s, 3H, isomers), 4.01 (d, J=11.6 Hz, 4H), 4.06 (d, J=11.6 Hz, 4H), 4.12 (d, J=9.6 Hz, 1H), 4.29 (d, J=8.0 Hz, 1H), 4.57 (d, J=5.6 Hz, 1H), 4.77 (d, J=3.6 Hz, 1H), 6.81-6.87 (m, 2H), 6.90 and 7.52 (two t, J=5.7 and 4.0 Hz, 1H, isomers), 7.11-7.13 (m, 2H), 7.23-7.27 (m, 2H), 7.35 (d, J=8.0 Hz, 1H)

Example 3

Preparation of 1-(4-(2-chloro-5-((1S,2S,3S,4R,5S)-2, 3,4-trihydroxy-1-(hydroxymethyl)-6,8-dioxabicyclo [3.2.1]octan-5-yl)benzyl)phenoxy)propan-2-one O-methyl oxime

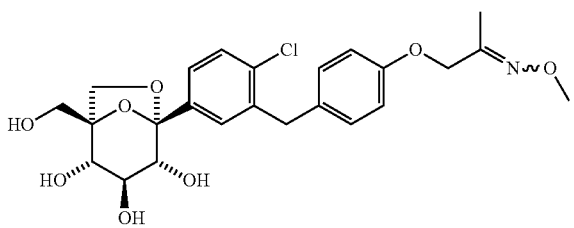 [SMILES: CON=C(C)COc1ccc(Cc2cc([C@]34OC[C@](CO)(O3)[C@@H](O)[C@H](O)[C@H]4O)ccc2Cl)cc1]

Step 1: Preparation of 2-(4-(allyloxy)benzyl)-4-bromo-1-chlorobenzene

To a solution of 4-(5-bromo-2-chlorobenzyl)phenol (6 g, 20.16 mmol, prepared as described in WO2006120208) in dry DMF (25 mL), was added Cs$_2$CO$_3$ (18.2 g, 60.6 mmol) and allyl bromide (4.2 mL, 50.6 mmol) at 0° C. and the reaction mixture was stirred at r.t. for 2 h. After the completion of the reaction as monitored by TLC, the reaction mixture was diluted with ethyl acetate (200 mL) and washed with water (3×30 mL). The combined organic layers were dried over Na$_2$SO$_4$ and the volatiles were evaporated in vacuo. The residue obtained was purified by column chromatography (silica gel, 0.4:9.6 Ethyl acetate:Pet. Ether) to afford the title compound (6.1 g, 89.6%).

Step 2: Preparation of (2S,3R,4S,5S,6R)-2-(3-(4-(allyloxy)benzyl)-4-chlorophenyl)-6-(hydroxy methyl)-2-methoxytetrahydro-2H-pyran-3,4,5-triol To a solution of 2-(4-(allyloxy)benzyl)-4-bromo-1-chlorobenzene (2.0 g, 5.92 mmol, prepared as described in Intermediate 1) in dry THF (50 mL), under nitrogen atmosphere, was added "BuLi (4.8 mL, 7.7 mmol, 1.6 M solution in hexanes) at −78° C. The reaction mixture was stirred at the same temperature for 30 min. A solution of (3R,4S,5R,6R)-3,4,5-tris((trimethylsilyl)oxy)-6-(((trimethylsilyl)oxy)methyl)tetrahydro-2H-pyran-2-one (3.6 g, 7.7 mol, prepared following the procedure given in US20070049537) in dry THF (40 mL) was added dropwise at the same temperature and stirred for another 3 h. After the completion of the reaction as confirmed by TLC, a solution of methanesulfonic acid (0.76 mL, 11.8 mmol) in methanol (30 mL) was added and the temperature was gradually raised to r.t. and stirred for 16 h. The reaction was quenched by the addition of triethylamine (3.3 mL) and volatiles were evaporated in vacuo. The residue obtained was dissolved in ethylacetate (300 mL) and washed with water (3×20 mL). The organic layers were dried over anhydrous Na$_2$SO$_4$ and volatiles were evaporated in vacuo. The residue obtained was purified by column chromatography (silica gel, 0.4:9.6 MeOH:DCM) to provide title compound (1.2 g, 45%).

ESIMS (m/z): 451.5 (M+1)

Step 3: Preparation of ((2R,3S,4S,5R,6S)-6-(3-(4-(allyloxy)benzyl)-4-chlorophenyl)-3,4,5-trihydroxy-6-methoxytetrahydro-2H-pyran-2-yl)methyl 4-methylbenzenesulfonate To a solution of (2S,3R,4S,5S,6R)-2-(3-(4-(allyloxy)benzyl)-4-chlorophenyl)-6-(hydroxymethyl)-2-methoxytetrahydro-2H-pyran-3,4,5-triol (1.2 g, 2.66 mmol) in leutidine (18.6 mL, 159.8 mmol), was added tosyl chloride (3.0 g, 15.98 mmol) at 0° C. The reaction mixture was stirred at r.t. for 12 h. After the completion of reaction as monitored by TLC, the reaction mixture was diluted with ethylacetate (50 mL) and washed with 5% HCl (3×10 mL). The organic layers were dried over anhydrous Na$_2$SO$_4$ and volatiles were evaporated in vacuo. The residue obtained was purified by column chromatography (silica gel, 0.7:9.3 MeOH:DCM) to provide title compound (1.42 g, 89%).

Step 4: Preparation of (2S,3S,4S,5R,6S)-6-(3-(4-(allyloxy)benzyl)-4-chlorophenyl)-3,4,5-trihydroxy-6-methoxytetrahydro-2H-pyran-2-carbaldehyde To a solution of ((2R,3S,4S,5R,6S)-6-(3-(4-(allyloxy)benzyl)-4-chlorophenyl)-3,4,5-trihydroxy-6-methoxytetrahydro-2H-pyran-2-yl)methyl 4-methylbenzenesulfonate (4.5 g, 7.49 mmol) in dry DMSO (30 mL), was added collidine (6.95 mL, 52.44 mmol) and the mixture was heated at 150° C. for 45 min. After the completion of the reaction as monitored by TLC, the reaction mixture was used as such for the next step.

Step 5: Preparation of (2S,3R,4S,5S)-2-(3-(4-(allyloxy)benzyl)-4-chlorophenyl)-6,6-bis(hydroxymethyl)-2-methoxytetrahydro-2H-pyran-3,4,5-triol The above reaction mixture was diluted with EtOH (67 mL) and heated to 55° C. To it was added para-formaldehyde (5.62 g, 187.25 mmol), followed by dropwise addition of 21% solution of sodium ethoxide in EtOH (22 mL). The resulting mixture was heated at 55° C. for 20 h. After the completion of the reaction as monitored by TLC, the reaction was quenched with a solution of NaHSO$_3$ (15.5 g, 149.8 mmol in 110 mL of water) and stirred for 20 min. The solvent was evaporated under reduced pressure and then diluted with ethyl acetate (300 mL) and washed with water (2×30 mL). The combined organic layers were dried over anhydrous Na$_2$SO$_4$ and volatiles were evaporated in vacuo. The residue obtained was purified by column chromatography (silica gel, 0.7:9.3 MeOH:DCM) to provide title compound (0.6 g, 16.5% over two steps).

ESIMS (m/z): 480.5 (M+)

Step 6: Preparation of (1S,2S,3S,4R,5S)-5-(3-(4-(allyloxy)benzyl)-4-chlorophenyl)-1-(hydroxymethyl)-6,8-dioxabicyclo[3.2.1]octane-2,3,4-triol To a solution of (2S,3R,4S,5S)-2-(3-(4-(allyloxy)benzyl)-4-chlorophenyl)-6,6-bis(hydroxymethyl)-2-methoxytetrahydro-2H-pyran-3,4,5-triol (0.5 g, 1.04 mmol) in dry DCM (20 mL), was added trifluoracetic acid (4.6 mL, 62.43 mmol) dropwise at 0° C. and the reaction mixture was stirred at r.t. for 1 h. After the completion of the reaction as monitored by TLC, the reaction mixture was diluted with ethyl acetate (100 mL) and washed sequentially with water (2×10 mL) and NaHCO$_3$ (2×10 mL). The combined organic layers were dried over anhydrous Na$_2$SO$_4$ and volatiles were evaporated in vacuo. The crude compound was used as such in the next reaction (440 mg, 94.3%).

ESIMS (m/z): 448.0 (M+)

Step 7: Preparation of (1R,2S,3S,4R,5S)-1-(acetoxymethyl)-5-(3-(4-(allyloxy)benzyl)-4-chlorophenyl)-6,8-dioxabicyclo[3.2.1]octane-2,3,4-triyl triacetate To a solution of (1S,2S,3S,4R,5S)-5-(3-(4-(allyloxy)benzyl)-4-chlorophenyl)-1-(hydroxymethyl)-6,8-dioxabicyclo[3.2.1]octane-2,3,4-triol (650 mg, 1.44 mmol) in dry THF (20 mL), was added DIPEA (1.75 mL, 10.08 mmol) followed by DMAP (66 mg, 0.525 mmol). The reaction was cooled to 0° C. and acetic anhydride (0.68 mL, 7.24 mmol) was added dropwise. The reaction was stirred at r.t. for 1 h. After the completion of the reaction as observed by TLC, the reaction was diluted with ethyl acetate (100 mL) and washed with water (3×10 mL).The combined organic layers were dried over anhydrous Na$_2$SO$_4$ and volatiles were evaporated in vacuo. The residue obtained was purified by column chromatography (silica gel, 1.7:8.3 Acetone:Pet. Ether) to provide title compound (0.6 g, 67.5%).

ESIMS (m/z): 635.2 (M+18)

Step 8: Preparation of (1R,2S,3S,4R,5S)-1-(acetoxymethyl)-5-(4-chloro-3-(4-hydroxybenzyl)phenyl)-6,8-dioxabicyclo[3.2.1]octane-2,3,4-triyl triacetate To a solution of (1R,2S,3S,4R,5S)-1-(acetoxymethyl)-5-(3-(4-(allyloxy)benzyl)-4-chlorophenyl)-6,8-dioxabicyclo[3.2.1]octane-2,3,4-triyl triacetate (0.6 g, 0.973 mmol) in dry THF (10 mL), was added Pd(PPh$_3$)$_4$ (337 mg, 0.29 mmol) followed by 1,3-dimethyl barbituric acid (1.57 g, 9.73 mmol). The reaction mixture was then refluxed at 90° C. for 1 h. After the completion of reaction as monitored by TLC, the reaction was quenched with saturated solution of NaHCO$_3$ (10 mL), diluted with ethyl acetate (100 mL) and then washed with water (3×10 mL). The combined organic layers were dried over anhydrous Na$_2$SO$_4$ and volatiles were evaporated in vacuo. The residue obtained was purified by column chromatography (silica gel, 5:5 Ethyl acetate:Pet. Ether) to provide title compound (0.53 g, 94%).

ESIMS (m/z): 594.6 (M+18)

Step 9: Preparation of (1R,2S,3S,4R,5S)-1-(acetoxymethyl)-5-(3-(4-(2-(tert-butyldimethyl silyloxy)propoxy)benzyl)-4-chlorophenyl)-6,8-dioxabicyclo[3.2.1]octane-2,3,4-triyl triacetate To a solution of (1R,2S,3S,4R,5S)-1-(acetoxymethyl)-5-(4-chloro-3-(4-hydroxybenzyl)phenyl)-6,8-dioxabicyclo[3.2.1]octane-2,3,4-triyl triacetate (500 mg, 0.86 mmol) in dry DMF (10 mL), was added (1-bromopropan-2-yloxy)(tert-butyl)dimethylsilane (327 mg, 1.3 mmol) and cesium carbonate (847 mg, 2.6 mmol). The reaction mixture was was stirred at 60° C. for 14 h. After completion of reaction, as confirmed by TLC, the reaction mixture was diluted with ethylacetate (150 mL) and washed with water (3×10 mL). The organic layer was dried over anhydrous Na$_2$SO$_4$ and volatiles were evaporated in vacuo. The residue obtained was purified by column chromatography (silica gel, 2:8 Ethyl acetate:Pet. Ether) to afford title compound (350 mg, 53.8%) as white solid.

ESIMS (m/z): 767.2 (M+18)

Step 10: Preparation of (1R,2S,3S,4R,5S)-1-(acetoxymethyl)-5-(4-chloro-3-(4-(2-hydroxypropoxy)benzyl)phenyl)-6,8-dioxabicyclo[3.2.1]octane-2,3,4-triyl triacetate A solution (1R,2S,3S,4R,5S)-1-(acetoxymethyl)-5-(3-(4-(2-(tert-butyldimethylsilyloxy)propoxy)benzyl)-4-chlorophenyl)-6,8-dioxabicyclo[3.2.1]octane-2,3,4-triyl triacetate (350 mg, 0.46 mmol) in Acetic acid:THF:Water (3:1:1, 5.0 mL) was stirred at r.t. for 48 h. After completion of the reaction, as confirmed by TLC, sat. solution of NaHCO$_3$ (10 mL) was added dropwise to the reaction mixture and organic layer was extracted with EtOAc (3×50 mL). The combined organic layers were dried over Na$_2$SO$_4$ and evaporated in vacuo. The residue obtained was purified by column chromatography (silica gel, 1:1 Ethyl acetate:Pet. Ether) to afford title compound (190 mg, 65.7%).

ESIMS (m/z): 652.7 (M+18)

Step 11: Preparation of (1R,2S,3S,4R,5S)-1-(acetoxymethyl)-5-(4-chloro-3-(4-(2-oxopropoxy)benzyl)phenyl)-6,8-dioxabicyclo[3.2.1]octane-2,3,4-triyl triacetate Oxalyl chloride (0.05 mL, 0.59 mmol) was added to a solution of DMSO (0.08 mL, 1.9 mmol) in dry DCM (1 mL) at −78° C. under nitrogen atmosphere. The reaction mixture was stirred for 5 min. at the same temperature and then a solution of (1R,2S,3S,4R,5S)-1-(acetoxymethyl)-5-(4-chloro-3-(4-(2-hydroxypropoxy)benzyl)phenyl)-6,8-dioxabicyclo[3.2.1]octane-2,3,4-triyl triacetate (190 mg, 0.29 mmol), in dry DCM (3 mL) was added. The reaction mixture was stirred at the same temperature for 30 min. Et$_3$N (0.25 mL, 1.79 mmol) was added and the reaction mixture was allowed to come to r.t. The crude compound was extracted with DCM (30 mL). The organic layer was separated, washed with water (15 mL). The combined organic layers were dried over Na$_2$SO$_4$ and concentrated in vacuo to afford the title compound, which was used as such in next step.

Step 12: Preparation of (1R,2S,3S,4R,5S)-1-(acetoxymethyl)-5-(4-chloro-3-(4-(2-(methoxy imino)propoxy)benzyl)phenyl)-6,8-dioxabicyclo[3.2.1]octane-2,3,4-triyl triacetate To a solution of (1R,2S,3S,4R,5S)-1-(acetoxymethyl)-5-(4-chloro-3-(4-(2-oxopropoxy)benzyl)phenyl)-6,8-dioxabicyclo[3.2.1]octane-2,3,4-triyl triacetate (180 mg, 0.28 mmol), in ethanol (8 mL) under nitrogen atmosphere, were added pyridine (0.114 mL, 1.42 mmol) and O-methylhydroxylamine hydrochloride (72 mg, 0.85 mmol). The reaction mixture was refluxed for 2 h. After completion of the reaction as confirmed by TLC, water (10 mL) was added to the reaction mixture and the crude compound was extracted with ethyl acetate (3×25 mL). The organic layers were dried over Na₂SO₄ and concentrated in vacuo to afford crude product which was purified by column chromatography (silica gel, 1.5:8.5 Acetone:Pet. Ether) to afford the title compound (120 mg, 63.8%).
ESIMS (m/z): 662.8 (M+1)

Step 13: Preparation of 1-(4-(2-chloro-5-((1S,2S,3S,4R,5S)-2,3,4-trihydroxy-1-(hydroxymethyl)-6,8-dioxabicyclo[3.2.1]octan-5-yl)benzyl)phenoxy)propan-2-one-O-methyl oxime To a solution of (1R,2S,3S,4R,5S)-1-(acetoxymethyl)-5-(4-chloro-3-(4-(2-(methoxy imino)propoxy)benzyl)phenyl)-6,8-dioxabicyclo[3.2.1]octane-2,3,4-triyl triacetate (120 mg, 0.18 mmol) in THF (0.8 mL), methanol (1.2 mL) and water (0.4 mL) was added lithium hydroxide monohydrate (15.2 mg, 0.36 mmol) at 0° C. The reaction mixture was stirred at r.t. for 1 h. Volatiles were evaporated in vacuo and the residue obtained was purified by column chromatography (silica gel, 1:9 MeOH:DCM) to provide the title compound (60 mg, 67%).
ESIMS (m/z): 494.6 (M+1)
¹H NMR (400 MHz, CD₃OD): δ 1.89 (s, 3H), 3.53 (d, J=7.9 Hz, 1H), 3.57-3.68 (m, 3H), 3.75-3.78 (m, 1H), 3.81-3.84 (m, 1H), 3.89 (s, 3H), 4.03 (s, 2H), 4.13 (d, J=7.5 Hz, 1H), 4.56 (s, 2H), 6.78-6.87 (m, 2H), 7.07-7.12 (m, 2H), 7.33-7.36 (m, 1H), 7.37-7.39 (m, 1H), 7.44-7.45 (m, 1H).

Example 4

Preparation of 2-(4-(2-chloro-5-((2S,3R,4R,5S,6R)-3,4,5-trihydroxy-6-(hydroxymethyl)tetrahydro-2H-pyran-2-yl)benzyl)phenyl)acetaldehyde O-methyl oxime

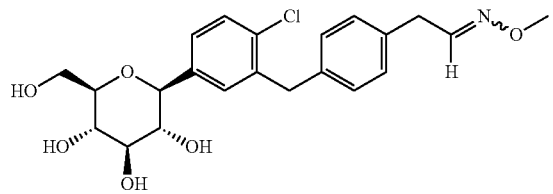 [SMILES: CON=CCc1ccc(Cc2cc([C@@H]3O[C@H](CO)[C@@H](O)[C@H](O)[C@H]3O)ccc2Cl)cc1]

Step 1: Preparation of (2R,3R,4R,5S,6S)-2-(acetoxymethyl)-6-(4-chloro-3-(4-(2-oxoethyl)benzyl)phenyl)tetrahydro-2H-pyran-3,4,5-triyl triacetate Oxalyl chloride (0.086 mL, 1.01 mmol) was added to a solution of DMSO (0.14 mL, 2.0 mmol) in dry DCM (1 mL) at −78° C. under nitrogen atmosphere. The reaction mixture was stirred for 5 min. at the same temperature and then a solution of (2R,3R,4R,5S,6S)-2-(acetoxymethyl)-6-(4-chloro-3-(4-(2-hydroxyethyl)benzyl)phenyl)tetrahydro-2H-pyran-3,4,5-triyl triacetate (0.35 g, 0.6 mmol, prepared by following the procedure as described in WO2011070592), in dry DCM (3 mL) was added. The reaction mixture was stirred at the same temperature for 20 min. NEt₃ (0.41 mL, 3.0 mmol) was added and the reaction mixture was allowed to come to r.t. Pet.ether (3 mL) was added to the reaction mixture and the solid was filtered. The filtrate was concentrated in vacuo to afford the title compound, which was used as such in next step.

Step 2: Preparation of (2R,3R,4R,5S,6S)-2-(acetoxymethyl)-6-(4-chloro-3-(4-(2-(methoxyimino)ethyl)benzyl)phenyl)tetrahydro-2H-pyran-3,4,5-triyl triacetate To a solution of (2R,3 R,4R,5S,6S)-2-(acetoxymethyl)-6-(4-chloro-3-(4-(2-oxoethyl)benzyl)phenyl)tetrahydro-2H-pyran-3,4,5-triyl triacetate (0.35 mg, 0.61 mmol), in ethanol (10 mL) under nitrogen atmosphere, were added pyridine (0.24 mL, 3.04 mmol), and O-methylhydroxylamine hydrochloride (151 mg, 1.82 mmol). The reaction mixture was refluxed for 2 h. After completion of the reaction as confirmed by TLC, the solvent was evaporated. The crude compound was diluted with ethyl acetate (25 mL). The organic layer was washed with water (3×10 mL), dried over Na₂SO₄ and concentrated in vacuo to afford crude product which was purified by column chromatography (silica gel, 1.0:9.0 Acetone:Pet. Ether) to afford the title compound (80 mg, 22%).
ESIMS (m/z): 604.8 (M+)

Step 3: Preparation of 2-(4-(2-chloro-5-((2S,3R,4R,5S,6R)-3,4,5-trihydroxy-6-(hydroxymethyl)tetrahydro-2H-pyran-2-yl)benzyl)phenyl)acetaldehyde O-methyl oxime To a solution of (2R,3R,4R,5S,6S)-2-(acetoxymethyl)-6-(4-chloro-3-(4-(2-(methoxyimino)ethyl)benzyl)phenyl)tetrahydro-2H-pyran-3,4,5-triyl triacetate (80 mg, 0.132 mmol) in THF (0.5 mL), methanol (0.7 mL) and water (0.3 mL) was added lithium hydroxide monohydrate (11 mg, 0.26 mmol) at 0° C. The reaction was stirred at r.t. for 1 h. Volatiles were evaporated in vacuo and the residue obtained was purified by column chromatography (silica gel, 0.5:9.5 MeOH:DCM) to provide the title compound (44 mg, 77%).
ESIMS (m/z): 436.8 (M+)
¹H NMR (400 MHz, CD₃OD): δ 3.04-3.07 (m, 2H), 3.16-3.18 (m, 2H), 3.20-3.23 (m, 2H), 3.39 (d, J=5.5 Hz, 1H), 3.45-3.49 (m, 1H), 3.57 and 3.66 (two singlets, 3H), 3.64-3.69 (m, 2H), 3.86-3.91 (m, 3H), 6.55 and 7.20 (two triplets, J=5.6 Hz, 1H), 6.88-6.9 (m, 1H), 6.92-6.95 (m, 2H), 7.05-7.08 (m, 1H), 7.12-7.17 (m, 2H).

Example 5

Preparation of 2-(4-(2-chloro-54(1S,2S,3S,4R,5S)-2,3,4-trihydroxy-1-(hydroxymethyl)-6,8-dioxabicyclo[3.2.1]octan-5-yl)benzyl)phenoxy)cyclopent-2-enone O-methyl oxime

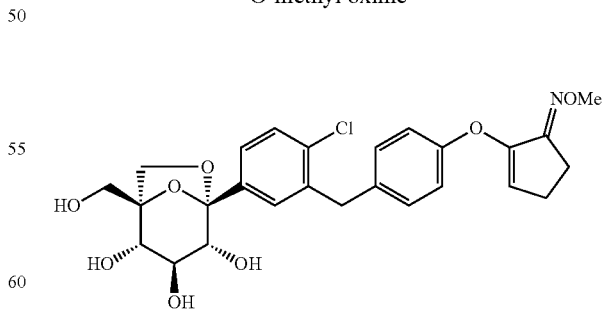

Step 1: Preparation of 2,2-dibromocyclopentanone

To a solution of cyclopentanone (2 gm, 23.81 mmol) in AcOH (238.05 mL), 10% Br₂/AcOH (24.3 mL) and catalytic amount of aqueous HBr were added at ° C. The reaction mixture was stirred for 1 h at r.t. After completion of the reaction as confirmed by TLC, the reaction mixture was diluted with ethylacetate (200 mL), washed with water (50 mL) and brine (50 mL) successively. The organic layer was dried over $Na_2SO_4$ and the volatiles were evaporated in vacuo. The residue obtained was purified by column chromatography (silica gel, 1:9 EtOAc:hexane) to provide title compound (3.85 g, 100%) as pale brown liquid.

ESIMS (m/z): 281.4 (M+18)

Step 2: Preparation of 2-(4-bromophenoxy)cyclopent-2-enone

To a solution of 4-bromophenol (500 mg, 2.9 mmol) in ACN (14.5 mL), 2,2-dibromo cyclopentanone (1.4 g, 8.7 mmol) and DIPEA (500 mg, 2.9 mmol) were added. The resulting mixture was stirred at r.t overnight. After completion of the reaction as confirmed by TLC, the reaction mixture was diluted with ethylacetate (150 mL), washed with water (50 mL) and brine (50 mL) successively. The combined organic layers were dried over $Na_2SO_4$ and the volatiles were evaporated in vacuo. The residue obtained was purified by column chromatography (silica gel, 1:9 EtOAc:hexane) to provide title compound (461 mg, 63%) as pale brown liquid.

ESIMS (m/z): 253.2 (M+1)

Step 3: Preparation of 2-(4-(4,4,5,5-tetramethyl-1,3, 2-dioxaborolan-2-yl)phenoxy)cyclopent-2-enone To a solution of 2-(4-bromophenoxy)cyclopent-2-enone (390 mg, 1.53 mmol), KOAc (456 mg, 4.5 mmol) in dioxane (7.5 mL), bis-pinacolato diborane (432 mg, 1.70 mmol) and $Pd(dppf)Cl_2$ (63 mg, 0.075 mmol) were added at r.t. The reaction mixture was heated to 80° C. for 5 h. After completion of the reaction as confirmed by TLC, the reaction mixture was diluted with ethylacetate (150 mL), washed with water (20 mL) and brine (20 mL) successively. The combined organic layers were dried over $Na_2SO_4$ and the volatiles were evaporated in vacuo. The residue obtained was purified by column chromatography (silica gel, 0.3:9.7 EtOAc:hexane) to provide title compound (294 mg, 63.6%) as off-white solid.

ESIMS (m/z): 301.1 (M+1)

Step 4: Preparation of (1R,2S,3S,4R,5S)-1-(acetoxymethyl)-5-(4-chloro-3-(4-((5-oxocyclopent-1-en-1-yl)oxy)benzyl)phenyl)-6,8-dioxabicyclo[3.2.1]octane-2,3,4-triyl triacetate To a solution of 2-(4-(4,4,5,5-tetramethyl-1,3,2-dioxaborolan-2-yl)phenoxy)cyclopent-2-enone (295 mg, 0.989 mmol), CsF (296 mg, 1.95 mmol) in dioxane (3.1 mL), (1R, 2S,3S,4R,5S)-1-(acetoxymethyl)-5-(3-(bromomethyl)-4-chlorophenyl)-6,8-dioxabicyclo[3.2.1]octane-2,3,4-triyl triacetate (369.4 mg, 0.65 mmol, Intermediate 2) and $Pd(PPh_3)$ (60 mg, 0.05 mmol) were added under $N_2$ atmosphere. The reaction mixture was heated to 110° C. for 1 h. After completion of the reaction as confirmed by TLC, the reaction mixture was diluted with ethylacetate (100 mL), washed with water (20 mL) and brine (20 mL) successively. The organic layer was dried over $Na_2SO_4$ and the volatiles were evaporated in vacuo. The residue obtained was purified by column chromatography (silica gel, 2:8 Acetone:hexane) to provide title compound (150 mg, 35%) as off-white solid.

ESIMS (m/z): 675.7 (M+18)

Step 5: Preparation of (1R,2S,3S,4R,5S)-1-(acetoxymethyl)-5-(4-chloro-3-(4-((5-(methoxyimino) cyclopent-1-en-1-yl)oxy)benzyl)phenyl)-6,8-dioxabicyclo[3.2.1]octane-2,3,4-triyl triacetate To a solution of (1R,2S,3S,4R,5S)-1-(acetoxymethyl)-5-(4-chloro-3-(4-((5-oxocyclopent-1-en-1-yl)oxy)benzyl)phenyl)-6,8-dioxabicyclo[3.2.1]octane-2,3,4-triyl triacetate (150 mg, 0.22 mmol) in ethanol (1.14 mL), O-methoxylamine.hydrochloride (35 mg, 0.45 mmol) and pyridine (0.91 mL, 1.14 mmol) were added. The reaction mixture was heated to 100° C. for 1 h. After completion of the reaction as confirmed by TLC, the reaction mixture was diluted with ethylacetate (100 mL) and the mixture was washed with 2% HCl (2×10 mL), water (50 mL) and brine (20 mL) successively. The organic layer was dried over $Na_2SO_4$ and the volatiles were evaporated in vacuo. The residue obtained was purified by column chromatography (silica gel, 1.5:8.5 Acetone:hexane) to provide title compound (110 mg, 70.2%) as off-white solid.

ESIMS (m/z): 686.8 (M+1)

Step 6: Preparation of 2-(4-(2-chloro-5-((1S,2S,3S, 4R,5S)-2,3,4-trihydroxy-1-(hydroxymethyl)-6,8-dioxabicyclo[3.2.1]octan-5-yl)benzyl)phenoxy)cyclopent-2-enone O-methyl oxime To a solution of compound (1R,2S,3S,4R,5S)-1-(acetoxymethyl)-5-(4-chloro-3-(4-((5-(methoxyimino)cyclopent-1-en-1-yl)oxy)benzyl)phenyl)-6,8-dioxabicyclo[3.2.1] octane-2,3,4-triyl triacetate (110 mg, 0.16 mmol) in MeOH: $THF:H_2O$ (0.48 mL, 0.36 mL, 0.12 mL), $LiOH.H_2O$ (10.3 mg, 0.24 mmol) was added at 0° C. The reaction mixture was stirred for 1 h at r.t. After completion of the reaction as confirmed by TLC, the solvent was evaporated in vacuo. The crude compound obtained was purified by column chromatography (silica gel, 0.4:9.6 MeOH:DCM) to provide title compound (75 mg, 90.5%) as off-white solid.

ESIMS (m/z): 518.7 (M+1)

$^1$H NMR (400 MHz, $CD_3OD$): δ 2.39-2.42 (m, 2H), 2.68-2.70 (m, 2H), 3.59 (dd, J=7.5 and 1.3 Hz, 1H), 3.68 (d, J=9.4 Hz, 1H), 3.77 (dd, J=8.3 and 1.1 Hz, 1H), 3.83 (d, J=12.5 Hz, 1H), 4.10 (s, 2H), 4.14 (d, J=7.5 Hz, 1H), 7.02 (d, J=8.4 Hz, 2H), 7.21 (d, J=8.6 Hz, 2H), 7.35-7.41 (m, 2H), 7.49 (d, J=1.9 Hz, 1H)

Example 6

Preparation of 2-(4-(2-chloro-5-((1S,2S,3S,4R,5S)-2, 3,4-trihydroxy-1-(hydroxymethyl)-6,8-dioxabicyclo [3.2.1]octan-5-yl)benzyl)phenoxy)-1-phenylethanone O-methyl oxime

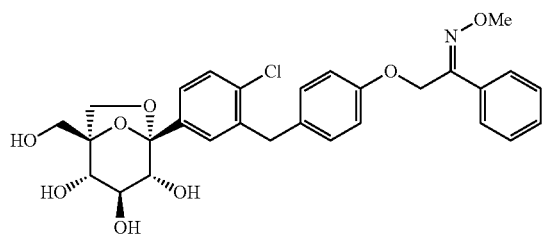 [SMILES: CO/N=C(/COc1ccc(Cc2cc([C@]34OC[C@](CO)(O3)[C@@H](O)[C@H](O)[C@H]4O)ccc2Cl)cc1)c1ccccc1]

Step 1: Preparation of (1R,2S,3S,4R,5S)-1-(acetoxymethyl)-5-(4-chloro-3-(4-hydroxybenzyl)phenyl)-6,8-dioxabicyclo[3.2.1]octane-2,3,4-triyl triacetate To a solution of 4-(4,4,5,5-tetramethyl-1,3,2-dioxaborolan-2-yl)phenol (500 mg, 2.25 mmol), CsF (865.83 mg, 5.70 mmol) in Dioxane (9.5 mL), (1R,2S,3S,4R,5S)-1-(acetoxymethyl)-5-(3-(bromomethyl)-4-chlorophenyl)-6,8-dioxabicyclo[3.2.1]octane-2,3,4-triyl triacetate (1.07 g, 1.90 mmol, Intermediate 2) and Pd(PPh$_3$) (173.3 mg, 0.15 mmol) were added under N$_2$ atmosphere. The reaction mixture was heated to 110° C. for 1 h. After completion of the reaction as confirmed by TLC, the reaction mixture was diluted with ethylacetate (100 mL) and washed with water (20 mL) and brine (20 mL) successively. The organic layer was dried over Na$_2$SO$_4$ and the volatiles were evaporated in vacuo. The residue obtained was purified by column chromatography (silica gel, 2:8 Acetone:hexane) to provide title compound (450 mg, 41.3%) as off-white solid.

ESIMS (m/z): 575.0 (M+18)

Step 2: Preparation of 2-bromo-1-phenylethanone

To a solution of acetophenone (500 mg, 4.16 mmol) in AcOH (20 mL) and catalytic amount of aq. HBr, 10% Br$_2$/AcOH (2.12 mL) was added at 0° C. The reaction mixture was stirred for 2 h at r.t. After completion of the reaction as confirmed by TLC, the reaction mixture was diluted with ethylacetate (100 mL) and washed with water (20 mL) and brine (20 mL) successively. The organic layer was dried over Na$_2$SO$_4$ and the volatiles were evaporated in vacuo. The residue obtained was purified by column chromatography (silica gel, 1:9 EtOAc:hexane) to afford the title compound (825 mg, 4.1 mmol, 100%).

ESIMS (m/z): 199.6 (M+1)

Step 3: Preparation of (1R,2S,3S,4R,5S)-1-(acetoxymethyl)-5-(4-chloro-3-(4-(2-oxo-2-phenylethoxy)benzyl)phenyl)-6,8-dioxabicyclo[3.2.1]octane-2,3,4-triyl triacetate To a solution of (1R,2S,3S,4R,5S)-1-(acetoxymethyl)-5-(4-chloro-3-(4-hydroxybenzyl)phenyl)-6,8-dioxabicyclo[3.2.1]octane-2,3,4-triyl triacetate (260 mg, 0.46 mmol) and DIPEA (0.38 mL, 2.25 mmol) in acetonitrile (2.25 mL), 2-bromo-1-phenylethanone (269 mg, 1.3 mmol) was added at r.t. and stirred overnight. After completion of the reaction as confirmed by TLC, the reaction mixture was diluted with ethylacetate (100 mL) and washed with water (20 mL) and brine (20 mL) successively. The organic layer was dried over Na$_2$SO$_4$ and the volatiles were evaporated in vacuo. The residue obtained was purified by column chromatography (silica gel, 2.2:7.8 acetone:hexane) to afford the title compound (230 mg, 0.33 mmol, 73.6%).

ESIMS (m/z): 712.3 (M+18)

Step 4: Preparation of (1R,2S,3S,4R,5S)-1-(acetoxymethyl)-5-(4-chloro-3-(4-(2-(methoxyimino)-2-phenylethoxy)benzyl)phenyl)-6,8-dioxabicyclo[3.2.1]octane-2,3,4-triyl triacetate To a solution of (1R,2S,3S,4R,5S)-1-(acetoxymethyl)-5-(4-chloro-3-(4-(2-oxo-2-phenyl ethoxy)benzyl)phenyl)-6,8-dioxabicyclo[3.2.1]octane-2,3,4-triyl triacetate (230 mg, 0.33 mmol) in ethanol (1.6 mL), pyridine (1.3 mL, 1.65 mmol) and O-methoxylamine (55.2 mg, 0.33 mmol) were added. The reaction mixture was heated to 100° C. After completion of the reaction as confirmed by TLC, the reaction mixture was diluted with ethylacetate (150 mL), washed with 2% HCl (2×20 mL), water (20 mL) and brine (20 mL) successively. The organic layer was dried over Na$_2$SO$_4$ and the volatiles were evaporated in vacuo. The residue obtained was purified by column chromatography (silica gel, 1.5:8.5 acetone:hexane) to afford the title compound (170 mg, 0.23 mmol, 70.9%).

ESIMS (m/z): 724.6 (M+1)

Step 5: Preparation of 2-(4-(2-chloro-5-((1S,2S,3S,4R,5S)-2,3,4-trihydroxy-1-(hydroxymethyl)-6,8-dioxabicyclo[3.2.1]octan-5-yl)benzyl)phenoxy)-1-phenylethanone O-methyl oxime To a solution of compound (1R,2S,3S,4R,5S)-1-(acetoxymethyl)-5-(4-chloro-3-(4-(2-(methoxyimino)-2-phenylethoxy)benzyl)phenyl)-6,8-dioxabicyclo[3.2.1]octane-2,3,4-triyl triacetate (170 mg, 0.23 mmol) in MeOH:THF:H$_2$O (0.7 mL, 0.5 mL, 0.17 mL), LiOH.H$_2$O (14.7 mg, 0.35 mmol) was added at 0° C. The reaction mixture was stirred for 1 h at r.t. After completion of the reaction as confirmed by TLC, solvent was evaporated in vacuo. The residue obtained was diluted with ethylacetate (100 mL), washed with water (10 mL) and brine (10 mL). The organic layer was dried over Na$_2$SO$_4$ and the volatiles were evaporated in vacuo. The residue obtained was purified by column chromatography (silica gel, MeOH:DCM) to afford the title compound (80 mg, 0.14 mmol, 61.8%).

ESIMS (m/z): 556.4 (M+1)

$^1$H NMR (400 MHz, CD$_3$OD): δ 3.53 (d, J=7.9 Hz, 1H), 3.58 (dd, J=7.5 and 1.1 Hz, 1H), 3.62-3.69 (m, 2H), 3.77 (d, J=8.3 Hz, 1H), 3.81-3.87 (m, 2H), 4.13 (d, J=7.5 Hz, 1H), 4.86 (s, 2H), 6.78 (d, J=8.7 Hz, 2H), 7.06 (d, J=8.6 Hz, 2H), 7.31-7.39 (m, 5H), 7.43-7.45 (m, 1H), 7.61-7.63 (m, 2H)

Example 7

Preparation of 1-(4-(4-(2-chloro-5-((1S,2S,3S,4R,5S)-2,3,4-trihydroxy-1-(hydroxylmethyl)-6,8-dioxabicyclo[3.2.1]octan-5-yl)benzyl)phenoxy)phenyl)ethanone O-ethyl oxime

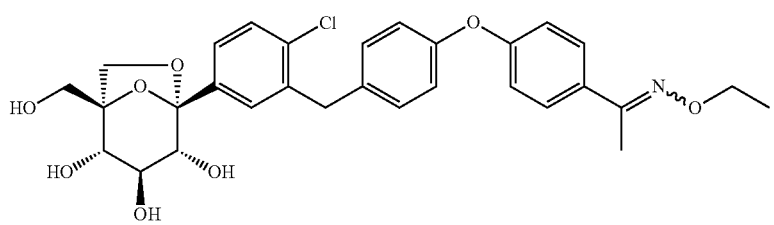 [SMILES: CCON=C(C)c1ccc(Oc2ccc(Cc3cc([C@]45OC[C@](CO)(O4)[C@@H](O)[C@H](O)[C@H]5O)ccc3Cl)cc2)cc1]

Step 1: Preparation of 1-(4-(4-nitrophenoxy)phenyl)ethanone

To a mixture of 1-fluoro-4-nitrobenzene (5.0 g, 35.43 mmol) and 4-hydroxyacetophenone (4.82 g, 35.40 mmol) in DMF (40 mL) was added potassium carbonate (9.79 g, 70.86 mmol). The reaction mixture was heated at 90° C. overnight. After the completion of the reaction as confirmed by TLC, the reaction mixture was diluted with EtOAc (200 mL) and washed with water (3×30 mL). The organic layer was separated, dried over $Na_2SO_4$ and concentrated in vacuo to afford the title compound (9.09 g, 99%) as a solid which was used as such in the next step.
ESIMS (m/z): 258.5 (M+1)

Step 2: Preparation of 1-(4-(4-aminophenoxy)phenyl)ethanone

To a solution of 1-(4-(4-nitrophenoxy)phenyl)ethanone (9.0 g, 35.02 mmol), in methanol (50 mL) under nitrogen atmosphere, was added a solution of 10% palladium on charcoal (1.80 g, 20% by weight) in methanol (20 mL). The reaction mixture was evacuated and purged with hydrogen balloon and stirred at r.t for 6 h. After the completion of reaction as confirmed by TLC, the reaction mixture was brought under nitrogen atmosphere. The reaction mixture was filtered through celite. The filtrate was concentrated in vacuo to afford the title compound (7.90 g, 99%) as a solid.

Step 3: Preparation of 1-(4-(4-iodophenoxy)phenyl)ethanone

To a solution of 1-(4-(4-aminophenoxy)phenyl)ethanone (6.0 g, 26.43 mmol), in dimethoxyethane (80 mL), was added a solution of sulphuric acid (10.9 mL, 206.19 mmol) in water (54.5 mL) dropwise. The resulting reaction mixture was cooled to 0° C. and a solution of sodium nitrite (2.74 g, 39.64 mmol) in water (18 mL) was added dropwise. The reaction mixture was stirred at 0-5° C. for additional 30 min and a solution of sodium iodide (19.81 g, 132.15 mmol) in water (54 mL) was added dropwise. The reaction mixture was stirred for additional 30 min. After the completion of reaction as confirmed by TLC, the reaction mixture was diluted with ethyl acetate (300 mL). The organic layer was separated, washed with water (100 mL), dried over $Na_2SO_4$ and concentrated in vacuo to afford crude product which was purified by column chromatography (silica gel, 3:7 EtOAc:Pet Ether) to afford the title compound (6.8 g, 76%) as a white solid.
ESIMS (m/z): 339.6 (M+2)

Step 4: Preparation of 1-(4-(4-(4,4,5,5-tetramethyl-1,3,2-dioxaborolan-2-yl)phenoxy)phenyl)ethanone To a solution of 1-(4-(4-iodophenoxy)phenyl)ethanone (5.0 g, 14.70 mmol) in 1,4-dioxane (40 mL) under nitrogen atmosphere, was added bis(pinacolato)diboron (4.51 g, 17.75 mmol), $Pd(dppf)Cl_2.CH_2Cl_2$ (483.0 mg, 0.59 mmol) and potassium acetate (4.35 g, 44.37 mmol). The reaction mixture was heated to 120° C. for 12 h. After the completion of the reaction, as confirmed by TLC, the solution was cooled to r.t. and filtered through celite. The solvent was evaporated in vacuo and the crude compound was diluted with ethyl acetate (200 mL). The organic layer was washed with water (3×30 mL), separated, dried over $Na_2SO_4$ and concentrated in vacuo to afford crude compound which was purified by column chromatography (silica gel, 3:7 EtOAc:Pet ether) to afford the title compound (3.62 g, 72%) as a white solid.
ESIMS (m/z): 339.5 (M+1)

Step 5: Preparation of (1R,2S,3S,4R,5S)-1-(acetoxymethyl)-5-(3-(4-(4-acetylphenoxy)benzyl)-4-chlorophenyl)-6,8-dioxabicyclo[3.2.1]octane-2,3,4-triyl triacetate To a mixture of (1R,2S,3S,4R,5S)-1-(acetoxymethyl)-5-(3-(bromomethyl)-4-chlorophenyl)-6,8-dioxabicyclo[3.2.1]octane-2,3,4-triyl triacetate (1.0 g, 1.77 mmol, Intermediate 2), 1-(4-(4-(4,4,5,5-tetramethyl-1,3,2-dioxaborolan-2-yl)phenoxy)phenyl)ethanone (899.0 mg, 2.66 mmol), Pd (dppf) $Cl_2$ (72 mg, 0.09 mmol) and sodium carbonate (563.0 mg, 5.31 mmol) under nitrogen atmosphere, was added DMF and $H_2O$ (9 mL, 1:1). The reaction mixture was heated at 80° C. for 1 h. After the completion of the reaction, as confirmed by TLC, the solution was cooled to r.t. and filtered through celite. The solvent was evaporated in vacuo and the crude compound was diluted with ethyl acetate (200 mL). The organic layer was washed with water (3×30 mL), separated, dried over $Na_2SO_4$ and concentrated in vacuo to afford crude compound which was purified by column chromatography (silica gel, 1:4 EtOAc:Pet ether) to afford the title compound (450 mg, 36.6%) as a white solid.
ESIMS (m/z): 717.5 (M+23), 695.6 (M+1)

Step 6: Preparation of (1R,2S,3S,4R,5S)-1-(acetoxymethyl)-5-(4-chloro-3-(4-(4-(1-(ethoxyimino)ethyl)phenoxy)benzyl)phenyl)-6,8-dioxabicyclo[3.2.1]octane-2,3,4-triyl triacetate To a solution of (1R,2S,3S,4R,5S)-1-(acetoxymethyl)-5-(3-(4-(4-acetylphenoxy)benzyl)-4-chlorophenyl)-6,8-dioxabicyclo[3.2.1]octane-2,3,4-triyl triacetate (300.0 mg, 0.43 mmol) in ethanol (5 mL) under nitrogen atmosphere, was added pyridine (0.17 mL, 2.15 mmol) and O-ethylhydroxylamine hydrochloride (84.0 mg, 0.86 mmol). The reaction mixture was heated at 80° C. for 4 h. After completion of the reaction as confirmed by TLC, the crude compound was diluted with ethyl acetate (2×20 mL). The organic layer was separated, washed with 5% HCl (10 mL), water (10 mL), dried over $Na_2SO_4$ and concentrated in vacuo to afford crude product which was purified by column chromatography (silica gel, 1:4 EtOAc:Pet Ether) to afford the title compound (230.0 mg, 72%) as a white solid.
ESIMS (m/z): 760.8 (M+23), 738.5 (M+1)

Step 7: Preparation of 1-(4-(4-(2-chloro-5-(1S,2S,3S,4R,5S)-2,3,4-trihydroxy-1-(hydroxyl methyl)-6,8-dioxabicyclo[3.2.1]octan-5-yl)benzyl)phenoxy)phenyl)ethanone O-ethyl oxime To a solution of (1R,2S,3S,4R,5S)-1-(acetoxymethyl)-5-(4-chloro-3-(4-(4-(1-(ethoxyimino)ethyl)phenoxy)benzyl)phenyl)-6,8-dioxabicyclo[3.2.1]octane-2,3,4-triyl triacetate (210.0 mg, 0.28 mmol), in THF (1.6 mL), methanol (2.4 mL) and water (0.8 mL) was added lithium hydroxide monohydrate (14.0 mg, 0.34 mmol) at 0° C. The reaction mixture was stirred at r.t. for 1 h. After the completion of reaction as confirmed by TLC, volatiles were evaporated in vacuo and the compound was diluted with ethyl acetate (50 mL). The organic layer was washed with water (2×10 mL), dried over $Na_2SO_4$ and concentrated to afford title compound (160.0 mg, 98%) as a white solid.
ESIMS (m/z): 569.9 (M+)
$^1$H NMR (400 MHz, MeOD): δ 1.29 (t, J=7.0 Hz, 3H), 2.17 (s, 3H), 3.55 (d, J=8.0 Hz, 1H), 3.59 (dd, J=7.6 Hz and 1.2 Hz, 1H), 3.65 (t, J=3.6 Hz, 1H), 3.67 (d, J=12.4 Hz, 1H), 3.77 (dd, J=8.4 Hz and 1.2 Hz, 1H), 3.83 (d, J=12.4 Hz, 1H), 4.06-4.11 (m, 2H), 4.14 (d, J=7.6 Hz, 1H), 4.18 (q, J=7.2 Hz, 2H), 6.89-6.94 (m, 4H), 7.20 (d, J=8.8 Hz, 2H), 7.36 (d, J=2.1 Hz, 1H), 7.40 (dd, J=8.4 Hz and 2.0 Hz, 1H), 7.49 (d, J=2.0 Hz, 1H), 7.60-7.63 (m, 2H).

Example 8

Preparation of 1-(4-(2-chloro-5-((2S,3R,4R,5S,6R)-3,4,5-trihydroxy-6-(hydroxyl methyl)tetrahydro-2H-pyran-2-yl)benzyl)phenyl)cyclopropane carbaldehyde O-methyl oxime

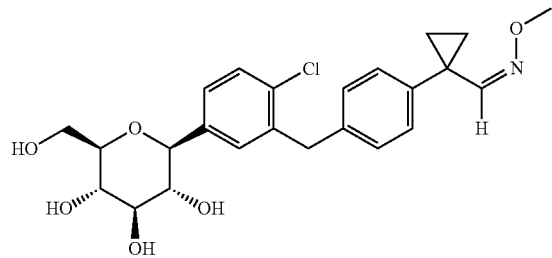 [SMILES: CO/N=C\C1(c2ccc(Cc3cc([C@@H]4O[C@H](CO)[C@@H](O)[C@H](O)[C@H]4O)ccc3Cl)cc2)CC1]

Step 1: Preparation of 1-(4-bromophenyl)cyclopropane carboxylic acid

To a mixture of 4-bromophenylacetonitrile (5.0 g, 25.44 mmol) and benzyltriethylammonium chloride (144.9 mg, 0.63 mmol) was added 1,2-dibromoethane (7.45 mL, 86.5 mmol). The reaction mixture was heated to 70° C. followed by dropwise addition of 50% aqueous sodium hydroxide solution (25 mL). The reaction mixture was heated at 70° C. for 7 h and then heated at 150° C. for 15 h. After the completion of reaction as confirmed by TLC, the reaction mixture was diluted with diethyl ether (100 mL). The aqueous layer was separated and acidified with 50% aqueous HCl to pH 1. The crude compound was diluted with ethyl acetate (500 mL). The organic layer was separated, washed with water (2×10 mL), dried over $Na_2SO_4$ and concentrated to afford title compound (3.1 g, 51%) as a solid.

ESIMS (m/z): 241.5 (M−1)

Step 2: Preparation of (1-(4-bromophenyl)cyclopropyl)methanol

To a solution of 1-(4-bromophenyl)cyclopropane carboxylic acid (3.0 g, 12.4 mmol) in dry THF (40 mL) under nitrogen atmosphere, was added borane dimethyl sulphide (8.83 mL, 19.8 mmol, 2 M solution in DCM) at 0° C. The reaction mixture was stirred at r.t for 4 h. After the completion of reaction as confirmed by TLC, the reaction mixture was quenched by dropwise addition of methanol until effervescence stopped. Volatiles were evaporated in vacuo and the compound was diluted with ethyl acetate (80 mL). The organic layer was separated; washed with water (3×10 mL), dried over $Na_2SO_4$ and concentrated. The crude product obtained was purified by column chromatography (silica gel, 1:4 EtOAc:Pet Ether) to afford title compound (2.7 g, 96%) as a solid.

ESIMS (m/z): 226.5 (M+1)

Step 3: Preparation of 1-(4-bromophenyl)cyclopropane carbaldehyde

To a solution of DMSO (2.18 mL, 30.7 mmol) in dry DCM (15.0 mL) under nitrogen atmosphere, was added oxalyl chloride (1.21 mL, 14.2 mmol) at −78° C. The reaction mixture was stirred at this temperature for 30 min followed by addition of solution of (1-(4-bromophenyl)cyclopropyl)methanol (2.7 g, 11.8 mmol), in DCM (15.0 mL). The reaction mixture was stirred at −78° C. for 45 min followed by addition of triethylamine (8.2 mL, 59.2 mmol) and further stirring at same temperature for 15 min and then at r.t. for 15 min. The reaction mixture was diluted with DCM (100 mL) and water (100 mL). The organic layer was separated, dried over $Na_2SO_4$ and concentrated in vacuo to afford title compound (2.6 g, 93%) as viscous oil which was used as such in the next step.

ESIMS (m/z): 226.5 (M+1)

Step 4: Preparation of 1-(4-(4,4,5,5-tetramethyl-1,3,2-dioxaborolan-2-yl)phenyl)cyclopropane carbaldehyde To a solution of 1-(4-bromophenyl)cyclopropane carbaldehyde (2.38 g, 10.5 mmol) in 1,4-dioxane (40 mL) under nitrogen atmosphere, was added bis(pinacolato)diboron (2.93 g, 11.5 mmol), $Pd(dppf)Cl_2 \cdot CH_2Cl_2$ (266.6 mg, 0.31 mmol) and potassium acetate (3.1 g, 31.5 mmol). The reaction mixture was heated to 120° C. for 12 h. After the completion of the reaction, as confirmed by TLC, the solution was cooled to r.t. and filtered through celite. The solvent was evaporated in vacuo and the crude compound was diluted with ethyl acetate (200 mL). The organic layer was washed with water (3×30 mL), separated, dried over $Na_2SO_4$ and concentrated in vacuo to afford crude compound which was purified by column chromatography (silica gel, 3:7 EtOAc: Pet ether) to afford the title compound (1.5 g, 53%) as a white solid.

ESIMS (m/z): 272.8 (M+1)

Step 5: Preparation of (2R,3R,4R,5S,6S)-2-(acetoxymethyl)-6-(4-chloro-3-(4-(1-formyl cyclopropyl)benzyl)phenyl)tetrahydro-2H-pyran-3,4,5-triyl triacetate To a mixture of (2R,3R,4R,5S,6S)-2-(acetoxymethyl)-6-(3-(bromomethyl)-4-chlorophenyl)tetrahydro-2H-pyran-3,4,5-triyl triacetate (1.0 g, 1.77 mmol, Intermediate 1), 1-(4-(4,4,5,5-tetramethyl-1,3,2-dioxaborolan-2-yl)phenyl) cyclopropane carbaldehyde (762.0 mg, 2.80 mmol), Pd(dppf)Cl$_2$ (76 mg, 0.09 mmol) and sodium carbonate (591.0 mg, 5.58 mmol) under nitrogen atmosphere, was added DMF and H$_2$O (9 mL, 1:1). The reaction mixture was heated at 80° C. for 1 h. After the completion of the reaction as confirmed by TLC, the solution was cooled to r.t and filtered through celite. The solvent was concentrated in vacuo. The crude compound was diluted with ethyl acetate (100 mL). The organic layer was washed with water (3×10 mL), dried over Na$_2$SO$_4$ and concentrated in vacuo. The crude compound was purified by column chromatography (silica gel, 1:4 EtOAc:Pet ether) to afford the title compound (320 mg, 29%) as a white solid ESIMS (m/z): 601.8 (M+1)

Step 6: Preparation of (2R,3R,4R,5S,6S)-2-(acetoxymethyl)-6-(4-chloro-3-(4-(1-(methoxyimino) methyl)cyclopropyl)benzyl)phenyl)tetrahydro-2H-pyran-3,4,5-triyl triacetate To a solution of (2R,3R,4R,5S,6S)-2-(acetoxymethyl)-6-(4-chloro-3-(4-(1-formylcyclopropyl)benzyl)phenyl)tetrahydro-2H-pyran-3,4,5-triyl triacetate (300.0 mg, 0.44 mmol), in ethanol (5 mL) under nitrogen atmosphere, was added pyridine (0.17 mL, 2.20 mmol) and O-methylhydroxylamine hydrochloride (73.0 mg, 0.88 mmol). The reaction mixture was heated at 80° C. for 4 h. After completion of the reaction as confirmed by TLC, the solvent was evaporated. The crude compound was diluted with ethyl acetate (40 mL). The organic layer was washed with 5% HCl (10 mL), water (10 mL), dried over $Na_2SO_4$ and concentrated in vacuo to afford crude product which was purified by column chromatography (silica gel, 1:4 EtOAc:Pet Ether) to afford the title compound (240 mg, 77%) as a white solid.

ESIMS (m/z): 630.8 (M+1)

Step 7: Preparation of 1-(4-(2-chloro-54(2S,3R,4R,5S,6R)-3,4,5-trihydroxy-6-(hydroxymethyl)tetrahydro-2H-pyran-2-yl)benzyl)phenyl)cyclopropane carbaldehyde O-methyl oxime To a solution of (2R,3R,4R,5S,6S)-2-(acetoxymethyl)-6-(4-chloro-3-(4-(1-(methoxy imino)methyl)cyclopropyl)benzyl)phenyl)tetrahydro-2-pyran-3,4,5-triyltriacetate (200.0 mg, 0.28 mmol), in THF (1.6 mL), methanol (2.4 mL) and water (0.8 mL) was added lithium hydroxide monohydrate (14.0 mg, 0.34 mmol) at 0° C. The reaction was stirred at r.t. for 1 h. After the completion of reaction as confirmed by TLC, volatiles were evaporated in vacuo and the compound was diluted with ethyl acetate (50 mL). The organic layer was washed with water (2×10 mL), dried over $Na_2SO_4$ and concentrated to afford the title compound (135 mg, 89%) as a white solid.

ESIMS (m/z): 462.6 (M+1)
$^1$H NMR (400 MHz, MeOD): δ 1.02-1.11 (m, 2H), 1.22-1.28 (m, 2H), 3.25-3.27 (m, 1H), 3.34-3.46 (m, 3H), 3.65-3.72 (m, 1H), 3.70 (s, 3H), 3.86 (dd, J=12.4 Hz and 2.0 Hz, 1H), 4.02-4.12 (m, 3H), 7.12-7.18 (m, 4H), 7.27 (dd, J=8.4 Hz and 2.4 Hz, 1H), 7.33-7.35 (m, 2H), 7.41 (s, 1H).

Example 9

Preparation of 2-(4-(2-(methoxyimino)ethoxy)benzyl)-4-((2S,3R,4R,5S,6R)-3,4,5-trihydroxy-6-(hydroxymethyl)tetrahydro-2H-pyran-2-yl)benzonitrile

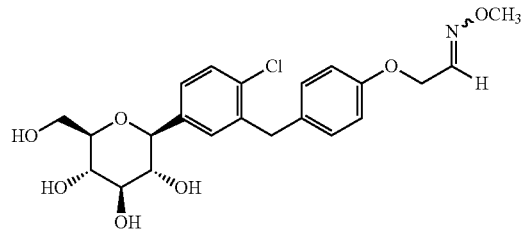 [SMILES: CON=CCOc1ccc(Cc2cc([C@@H]3O[C@H](CO)[C@@H](O)[C@H](O)[C@H]3O)ccc2Cl)cc1]

Step 1: Preparation of (2R,3R,4R,5S,6S)-2-(acetoxymethyl)-6-(3-(4-(2-((tert-butyl dimethylsilyl)oxy)ethoxy)benzyl)-4-cyanophenyl)tetrahydro-2H-pyran-3,4,5-triyl triacetate To a solution of (2R,3R,4R,5S,6S)-2-(acetoxymethyl)-6-(4-cyano-3-(4-hydroxy benzyl)phenyl)tetrahydro-2H-pyran-3,4,5-triyl triacetate (240.0 mg, 0.44 mmol, prepared by methods described in WO 2007128749) in DMF (5 mL) under nitrogen atmosphere, was added cesium carbonate (435.2 mg, 1.33 mmol) at 0° C., followed by addition of solution of 2-bromo-tert-butyl dimethyl silyl ethanol (159.6 mg, 0.66 mmol) in DMF (2 mL). The reaction mixture was stirred at r.t. overnight and heated at 60° C. for 2 h. After the completion of the reaction as confirmed by TLC, the reaction mixture was diluted with water (20 mL) and the crude compound was extracted with ethyl acetate (2×50 mL). The organic layer was washed with water (30 mL), dried over $Na_2SO_4$ and concentrated to afford the crude compound which was purified by column chromatography (silica gel, 1:49 EtOAc:Pet Ether) to afford the title compound (180 mg, 58%) as a solid.

ESIMS (m/z): 716 (M+39).

Step 2: Preparation of (2R,3R,4R,5S,6S)-2-(acetoxymethyl)-6-(4-cyano-3-(4-(2-hydroxy ethoxy)benzyl)phenyl)tetrahydro-2H-pyran-3,4,5-triyl triacetate To a solution of (2R,3R,4R,5S,6S)-2-(acetoxymethyl)-6-(3-(4-(2-((tert-butyl dimethyl silyl)oxy)ethoxy)benzyl)-4-cyanophenyl)tetrahydro-2H-pyran-3,4,5-triyl triacetate (180.0 mg, 0.25 mmol), was added acetic acid (1.5 mL) and water (0.5 mL) and the reaction mixture was stirred overnight at r.t. After the completion of the reaction as confirmed by TLC, the reaction mixture was diluted with ethyl acetate (50 mL) followed by neutralization with sodium bicarbonate solution till effervescence ceased. The organic layer was separated, washed with water (2×20 mL), dried over $Na_2SO_4$ and concentrated in vacuo to afford crude product which was purified by column chromatography (silica gel, 3:2 EtOAc:Pet Ether) to afford title compound (140.0 mg, 95%) as a solid.

ESIMS (m/z): 602 (M+39)

Step 3: Preparation of (2R,3R,4R,5S,6S)-2-(acetoxymethyl)-6-(4-cyano-3-(4-(2-oxoethoxy)benzyl)phenyl)tetrahydro-2H-pyran-3,4,5-triyl triacetate To a solution of DMSO (0.04 mL, 0.62 mmol) in dry DCM (1.0 mL) under nitrogen atmosphere, was added oxalyl chloride (0.02 mL, 0.28 mmol) at −78° C. The reaction mixture was stirred at this temperature for 5 min followed by addition of a solution of (2R,3R,4R,5S,6S)-2-(acetoxymethyl)-6-(4-cyano-3-(4-(2-hydroxyethoxy)benzyl)phenyl)tetrahydro-2H-pyran-3,4,5-triyl triacetate (140 mg, 0.24 mmol), in DCM (1 mL). The reaction mixture was stirred at −78° C. for 30 min followed by addition of triethylamine (0.16 mL, 1.20 mmol) and further stirring at same temperature for 10 min and then at r.t. for 10 min. The reaction mixture was diluted with hexane (50 mL) and filtered to remove the solids. The filtrate was dried over $Na_2SO_4$ and concentrated in vacuo to afford crude title compound (100 mg, 72%) as viscous oil which was used without purification for the next step.

Step 4: Preparation of (2R,3R,4R,5S,6S)-2-(acetoxymethyl)-6-(4-cyano-3-(4-(2-(methoxyimino)ethoxy)benzyl)phenyl)tetrahydro-2H-pyran-3,4,5-triyl triacetate To a solution of (2R,3R,4R,5S,6S)-2-(acetoxymethyl)-6-(4-cyano-3-(4-(2-oxoethoxy)benzyl)phenyl)tetrahydro-2H-pyran-3,4,5-triyl triacetate (100.0 mg, 0.17 mmol) in ethanol (4 mL) under nitrogen atmosphere, was added pyridine (0.07 mL, 0.86 mmol) and O-methylhydroxylamine hydrochloride (28.7 mg, 0.34 mmol). The reaction mixture was heated at 80° C. for 2 h. After completion of the reaction as confirmed by TLC, the solvent was evaporated. The crude compound was diluted with ethyl acetate (40 mL). The organic layer was separated, washed with 5% HCl (10 mL), water (10 mL), dried over $Na_2SO_4$ and concentrated in vacuo to afford crude product which was purified by column chromatography (silica gel, 1:49 EtOAc:Pet Ether) to afford title compound (60 mg, 43%) as solid.

ESIMS (m/z): 611.8 (M+1)

Step 5: Preparation of 2-(4-(2-(methoxyimino)ethoxy)benzyl)-4-((2S,3R,4R,5S,6R)-3,4,5-trihydroxy-6-(hydroxymethyl)tetrahydro-2H-pyran-2-yl)benzonitrile To a solution of (2R,3R,4R,5S,6S)-2-(acetoxymethyl)-6-(4-cyano-3-(4-(2-(methoxyimino)ethoxy)benzyl)phenyl)tetrahydro-2H-pyran-3,4,5-triyl triacetate (60.0 mg, 0.10 mmol), in THF (0.33 mL), methanol (0.5 mL) and water (0.16 mL) was added lithium hydroxide monohydrate (5.37 mg, 0.12 mmol) at 0° C. The reaction was stirred at r.t. for 1 h. After the completion of reaction as confirmed by TLC, volatiles were evaporated in vacuo and the compound was diluted with ethyl acetate (20 mL). The organic layer was washed with water (5 mL), dried over $Na_2SO_4$ and concentrated to afford title compound (40 mg, 93%) as a white solid.

$^1$H NMR (400 MHz, MeOD): δ 3.20-3.29 (m, 1H), 3.90-3.47 (m, 3H), 3.70 (dd, J=11.6 Hz and 5.2 Hz, 1H), 3.82 and 3.89 (two s, 3H), 4.11-4.20 (m, 3H), 4.56-4.57 (m, 2H), 4.77-4.95 (m, 1H), 6.82-6.90 (m, 2H), 7.16 (dd, J=8.8 Hz and 2.8 Hz, 2H), 7.45 (dd, J=7.6 Hz and 4.0 Hz, 1H), 7.49-7.53 (m, 2H), 7.63 and 7.654 (two s, 1H).

ESIMS (m/z): 443.8 (M+1)

The compounds listed in Table 2, 3 and 4 were prepared essentially following the procedures described for Examples I to IX.

TABLE 2

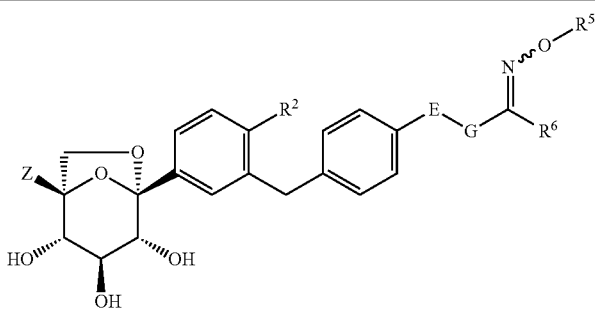

| Example No. | Z | $R^2$ | $R^5$ | $R^6$ | E | G | ESIMS (m/z) |
|---|---|---|---|---|---|---|---|
| 10 | $CH_2OH$ | Cl | $CH_3$ | H | O | $CH_2$ | 478.7 (M − 1) |
| 11 | $CH_2OH$ | Cl | $CH_3$ | H | O | $C_2H_4$ | 494.5 (M + 1) |
| 12 | $CH_2OH$ | Cl | $CH_3$ | H | O | n-decyl | 606.8 (M + 1) |
| 13 | $CH_2OH$ | Cl | $CH_3$ | H | O | p-$C_6H_4$ | 542.8 (M + 1) |
| 14 | $CH_2OH$ | Cl | $CH_3$ | H | O | o-$C_6H_4$ | 442.7 (M + 1) |
| 15 | $CH_2OH$ | Cl | $CH_3$ | $CH_3$ | O | p-$C_6H_4$ | 556.2 (M + 1) |
| 16 | $CH_2OH$ | Cl | $CH_3$ | H | Bond | —CH=CH— | 476.6 (M + 1) |
| 17 | $CH_2OH$ | Cl | $CH_3$ | H | Bond | cyclopropylene | 490.8 (M + 1) |
| 18 | $CH_2OH$ | Cl | $C_2H_5$ | H | O | $CH_2$ | 491.7 (M − 1) |
| 19 | $CH_2OH$ | Cl | $C_2H_5$ | H | O | $C_2H_4$ | 508.8 (M + 1) |
| 20 | $CH_2OCOOC_2H_5$ | Cl | $CH_3$ | H | O | $C_2H_4$ | 588.6 (M + 23) |
| 21 | $CH_2OCOOC_2H_5$ | Cl | $CH_3$ | H | O | $CH_2$ | 552.8 (M + 1) |

TABLE 3

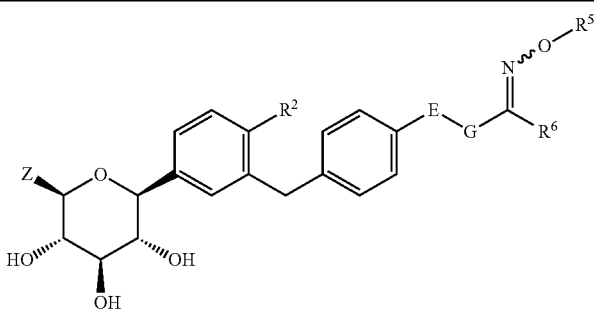

| Example No. | Z | $R^2$ | —$R^5$ | —$R^6$ | —E | —G | ESIMS (m/z) |
|---|---|---|---|---|---|---|---|
| 22 | $CH_2OH$ | H | $CH_3$ | H | O | $CH_2$ | 418.4 (M + 1) |
| 23 | $CH_2OH$ | H | $CH_3$ | H | O | $C_2H_4$ | 432.8 (M + 1) |
| 24 | $CH_2OH$ | Cl | H | $NH_2$ | O | $CH_2$ | 453.5 (M + 1) |

TABLE 3-continued

| 25 | $CH_2OH$ | Cl | $CH_3$ | H | O | $C_2H_4$ | 483.9 (M + 18) |
| 26 | $CH_2OH$ | Cl | $CH_3$ | $C_6H_5$ | O | $CH_2$ | 528.7 (M + 1) |
| 27 | $CH_2OH$ | Cl | $C_2H_5$ | H | O | $CH_2$ | 466.7 (M + 1) |
| 28 | $CH_2OH$ | Cl | $CH_3$ | H | bond | —C($CH_3$)=CH— | 462.6 (M + 1) |

TABLE 4

| Example No. | $R^5$ | $R^6$ | E | G | ESIMS (m/z) |
|---|---|---|---|---|---|
| 29 | $CH_3$ | $CH_3$ | O | $CH_2$ | 466.6 (M + 1) |
| 30 | $CH_3$ | H | O | $C_2H_4$ | 466.6 (M + 1) |

The SGLT inhibitory effects of the compounds of the present invention were demonstrated by following test procedures.

TABLE 5

| | | % inhibition of Methyl-α-D-[U-$^{14}$C] Glucopyranoside uptake (CHO-K1 cells) mediated by SGLT-2 | | |
|---|---|---|---|---|
| | Compound | | | |
| S. No. | No. | 1 nM | 10 nM | 100 nM |
| 1. | 1 | 9.28 | 34.53 | 53.07 |
| 2. | 2 | 8.98 | 27.72 | 43.02 |
| 3. | 11 | NE | 20.13 | 50.84 |
| 4. | 12 | NE | 17.03 | 45.03 |
| 5. | 19 | 56.86 | 81.55 | 91.64 |
| 6. | 21 | 54.59 | 78.69 | 91.00 |
| 7. | 23 | 25.42 | 73.32 | 93.84 |
| 8. | 25 | NE | 15.99 | 50.73 |
| 9. | 26 | NE | 22.75 | 52.21 |
| 10. | 29 | 40.24 | 37.91 | 77.19 |
| 11. | 30 | 35.57 | 37.29 | 54.00 |

NE = Not Effective

In Vitro Studies

Preparation of Mouse SGLT-2 Expressing Cells

Full-length mouse SGLT-2 cDNA was amplified from C57BL/6J mouse kidneys and introduced in the pcDNA3.1 (+) expression vector (Invitrogen, Inc.) and propagated in *Escherichia coli* strain DH5α using LuriaBertani (LB) medium containing ampicillin. Mouse SGLT-2 recombinant expression plasmid DNA was transfected into CHO-K1 cells (American Type Culture Collection) using Superfect Transfection Reagent according to a manufacturer suggested protocol. Stably transfected cells were selected using G418 antibiotic selection pressure.

Methyl-α-D-[U-$^{14}$C]Glucopyranoside Uptake Assay for SGLT-2

Cells expressing mSGLT-2 were seeded on 96-well tissue culture plates (Greiner, Inc.) in RPMI containing 10% FBS and 400 µg/mL G418 (0.8×10$^5$ cells per well in 200 µL medium) and incubated at 37° C. under 5% carbon dioxide for 24 h prior to the assay. Cells were washed twice with 200 µL of either sodium buffer (140 mM NaCl, 4.7 mM KCl, 2.2 mM $CaCl_2$, 1.2 mM $MgCl_2$, 10 mM Tris/Hepes, pH 7.4) or sodium-free buffer (137 mM N-methyl-glucamine, 4.7 mM KCl, 2.2 mM $CaCl_2$, 1.2 mM $MgCl_2$, 10 mM Tris/Hepes, pH 7.4). Reaction mixture containing test compounds at different concentrations diluted in assay buffer, 0.1 mM unlabeled Methyl-α-D-glucopyranoside and 1 µCi/well methyl-α-D-[U-$^{14}$C]glucopyranoside (American Radiochemicals) was added per well of a 96-well plate and incubated at 37° C. for 1 h. Cells were washed thrice with 200 µL of wash buffer (140 mM NaCl, 4.7 mM KCl, 2.2 mM $CaCl_2$, 1.2 mM $MgCl_2$, 10 mM Tris/Hepes, pH 7.4 containing 500 µM phlorizin) and lysed using 50 µL of 0.25N NaOH. Methyl-α-D-[U-$^{14}$C]glucopyranoside uptake was quantitated using a Top count scintillation counter (PerkinElmer, Inc.). All the test compounds were assayed in triplicates.

Preparation of Human SGLT-1 Expressing Cells

Full-length human SGLT-1 cDNA in the pCMV-XL-Neo expression vector was obtained from Origene Corporation and propagated in *Escherichia coli* strain DH5α using Luria-Bertani (LB) medium containing ampicillin. Human SGLT-1 expression plasmid DNA was transfected into CHO-K1 cells (American Type Culture Collection) using Superfect Transfection Reagent according to a manufacturer suggested protocol. Stably transfected cells were selected using G418 antibiotic selection pressure.

Methyl-α-D-[U-$^{14}$C]Glucopyranoside Uptake Assay for SGLT-1

Cells expressing hSGLT-1 were seeded on 96-well tissue culture plates (Greiner, Inc.) in RPMI containing 10% FBS and 800 µg/ml G418 (0.8×10$^5$ cells per well in 200 µL medium) and incubated at 37° C. under 5% carbon dioxide for 24 h prior to the assay. Cells were washed twice with 200 µL of either sodium buffer (140 mM NaCl, 4.7 mM KCl, 2.2 mM $CaCl_2$, 1.2 mM $MgCl_2$, 10 mM Tris/Hepes, pH 7.4) or sodium-free buffer (137 mM N-methyl-glucamine, 4.7 mM KCl, 2.2 mM $CaCl_2$, 1.2 mM $MgCl_2$, 10 mM Tris/Hepes, pH 7.4). Reaction mixture containing test compounds diluted in assay buffer, 1 mM unlabeled Methyl-α-D-glucopyranoside and 1 µCi/well methyl-α-D-[U-$^{14}$C]glucopyranoside (American Radiochemicals) was added per well of a 96-well plate and incubated at 37° C. for 1 h. Cells were washed thrice with 200 µL of wash buffer (140 mM NaCl, 4.7 mM KCl, 2.2 mM $CaCl_2$, 1.2 mM $MgCl_2$, 10 mM Tris/Hepes, pH 7.4 containing 500 µM phlorizin) and lysed using 50 µL of 0.25N NaOH. Methyl-α-D[U-$^{14}$C]glucopyranoside uptake was quantitated using a Top count scintillation counter (PerkinElmer, Inc.). All the test compounds were assayed in triplicates.

TABLE 6

| S. No. | Compound No. | % inhibition of Methyl-α-D-[U-$^{14}$C] Glucopyranoside uptake (CHO-K1 cells) mediated by SGLT-1 | | |
|---|---|---|---|---|
| | | 100 nM | 1 μM | 10 μM |
| 1. | 1 | 10.05 | 45.14 | 65.53 |
| 2. | 2 | 9.08 | 53.11 | 57.80 |
| 3. | 11 | 25.73 | 53.68 | 68.18 |
| 4. | 12 | 22.52 | 60.71 | 72.35 |
| 5. | 19 | 24.24 | 51.67 | 88.66 |
| 6. | 21 | 40.19 | 82.67 | 94.12 |
| 7. | 23 | 23.22 | 56.00 | 88.91 |
| 8. | 25 | 5.99 | 40.15 | 69.31 |
| 9. | 26 | 2.98 | 16.36 | 59.19 |
| 10. | 29 | N.E. | 70.01 | 92.90 |
| 11. | 30 | 24.02 | 26.35 | 77.94 |

N.E. = Not Effective

In Vivo Studies

Estimation of Urinary Glucose in C57BL/6J Mice

C57BL/6J mice were fasted 4 h before drug treatment. Fasted mice were weighed and randomized into different groups based on their body weight (n=6). At time $T_0$ test compounds and standard compounds suspended in 0.25% CMC or PEG 400 formulation, were administered to respective groups and kept in metabolic cages (6 mice/cage) after dosing. Animals were fed after drug administration and urine was collected over a period of 24 h. Urinary volume was measured and urinary glucose was estimated using Merckotest Glucose Reagent (Merck Specialties Pvt. Ltd., India).

TABLE 7

| S. No. | Compound No. | UGE in mice (in mg/g of feed consumed) at 3 mpk |
|---|---|---|
| 1. | 19 | 64.6 |
| 2. | 21 | 77.6 |
| 3. | 23 | 70.8 |
| 4. | 1 | 56.1 |
| 5. | 2 | 43.6 |
| 6. | 11 | 56.1 |
| 7. | 12 | 76.95 |
| 8. | 9 | 88 |

Estimation of Urinary Glucose in Rat

Rats were fasted overnight (14 hrs) before drug treatment. Fasted rats were weighed and randomized into different groups based on their body weight (n=4). At time $T_0$ test compounds and standard compound suspended in 0.25% C.M.C or PEG 400 formulation were administered to respective groups and kept the animals in metabolic cages (1 rat/cage) after dosing. Animals were fed after drug administration and urine was collected over a period of 24 hrs. Urine volume was measured and urinary glucose was estimated using Merckotest Glucose Reagent (Merck Specialties Pvt. Ltd., India).

TABLE 8

| S. No. | Compound No. | UGE in rat (in mg/g of feed consumed) at 3 mpk |
|---|---|---|
| 1. | 19 | 75.2 |
| 2. | 23 | 69.1 |

The invention claimed is:

1. A compound of Formula I,

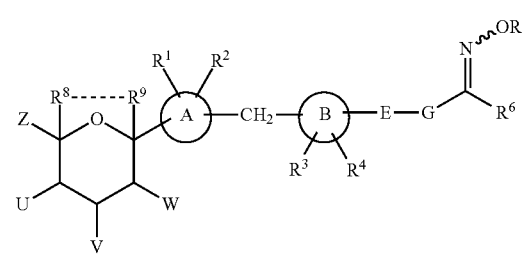

Formula I wherein:
'—' is either a single bond or absent;
ring A represents monocyclic or polycyclic $C_{3-20}$ cycloalkyl, $C_{6-10}$ aryl, 5-10 membered heteroaryl or 3-14 membered heterocyclyl ring;
ring B represents monocyclic or polycyclic $C_{3-20}$ cycloalkyl, $C_{6-10}$ aryl, 5-10 membered heteroaryl or 3-14 membered heterocyclyl ring;
U, V and W are independently selected from —H, $C_{1-12}$ alkyl, $C_{2-12}$ alkenyl, $C_{2-12}$ alkynyl, —OH, —CN, —N$_3$, —NO$_2$, —OCONH$_2$, —F, —Cl, —Br, —I, —COOH, —CONH$_2$, —CONHNH$_2$, —NH$_2$, —NHCONH$_2$, —NHCSNH$_2$, —NH(C=NH)NH$_2$, —NHNH$_2$, —NHCHO, —NHCOOH, —SH, —SO$_3$H, —CH(=NOH), —COR$^a$, —OR$^9$, —COOR$^a$, —CONR$^a$R$^b$, —NR$^a$R$^b$, —NR$^a$SO$_2$R$^b$, —NR$^a$CONR$^b$R$^c$, —NR$^a$COR$^b$, —NR$^a$COOR$^b$, —OCOR$^a$, —OCOOR$^a$, —OCONR$^a$R$^b$, —SR$^a$, —S(O)R$^a$, —S(O)$_2$R$^a$, —SO$_2$NR$^a$R$^b$, —CR$^a$(=NOR$^b$), —NHP(O) R$^a$R$^b$; wherein the said $C_{1-12}$ alkyl, $C_{2-12}$ alkenyl and $C_{2-12}$ alkynyl, may be substituted with substituents selected from R$^{11}$;
provided that atleast two out of U, V and W represent —OR$^9$;
Z represents —(CH$_2$)$_n$OR$^a$, —OR$^a$, —OCOR$^a$, —OCOOR$^a$, —OCONR$^a$R$^b$, $C_{1-12}$ alkyl, $C_{2-12}$ alkenyl, $C_{2-12}$ alkynyl, —CN, —OCONH$_2$, —CHO, —COOH, —CONH$_2$, —CONHNH$_2$, —NH$_2$, —NHCOOH, —CH$_2$OH, —OH, —SH, —SO$_3$H, —CH(=NOH), —CH(=NCN), —COR$^a$, —COOR$^a$, —CONR$^a$R$^b$, —NR$^a$R$^b$, —NR$^a$SO$_2$R$^b$, —NR$^a$CONR$^b$R$^c$, —NR$^a$NR$^b$ R$^c$, —NR$^a$COR$^b$, —NR$^a$COOR$^b$, —SR$^a$, —S(O)R$^a$, —S(O)$_2$R$^a$, —SO$_2$NR$^a$R$^b$ or —CR$^a$(=NOR$^b$); wherein the said $C_{1-12}$ alkyl, $C_{2-12}$ alkenyl and $C_{2-12}$ alkynyl, may be substituted with substituents selected from R$^{11}$;
R$^1$, R$^2$, R$^3$ and R$^4$ are independently selected from —H, $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —N$_3$, —NO$_2$, —OCONH$_2$, —F, —Cl, —Br, —I, —CHO, —COOH, —CONH$_2$, —NH$_2$, —NHCONH$_2$, —NHCHO, —NHCOOH, —OH, —OR$^a$, —SH, —SO$_3$H; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may be substituted with substituents selected from $R^{11}$;

$R^5$ represents —H, $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl or 5-10 membered heteroaryl; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may be substituted with substituents selected from $R^{11}$;

$R^6$ represents —H, $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —NH$_2$, —NHCONH$_2$, —NHCHO, —OH, —SH, —NR$^a$R$^b$, —NR$^a$CONR$^b$R$^c$, —NR$^a$COR$^b$, —OR$^a$ or —SR$^a$; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may be substituted with substituents selected from $R^{11}$;

E represents O, S, SO, SO$_2$, NR$^{10}$ or a single bond;

G represents $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl or 5-10 membered heteroaryl; each of which may be substituted with substituents selected from $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —NH(C=NH)NH$_2$, —NHNH$_2$, —NHCHO, —NHCHS, —NHCOOH, —NHCSOH, —OH, —SH, —SO$_3$H, —CH(=NOH), —CH(=NCN), —COR$^a$, —CSR$^a$, —COOR$^a$, —CSOR$^a$, —COSR$^a$, —CONR$^a$R$^b$, —CSNR$^a$R$^b$, —COCOR$^a$, —CONR$^a$NR$^b$R$^c$, —CSNR$^a$NR$^b$R$^c$, —CSNR$^a$R$^b$, —NR$^a$R$^b$, —NR$^a$SO$_2$R$^b$, —NR$^a$CONR$^b$R$^c$, —NR$^a$CSNR$^b$R$^c$, —NR$^a$(C=NR$^b$)NR$^c$R$^d$, —NR$^a$NR$^b$R$^c$, —NR$^a$COR$^b$, —NR$^a$CSR$^b$, —NR$^a$COOR$^b$, —NR$^a$CSOR$^b$, —OR$^a$, —OCOR$^a$, —OCOOR$^a$, —OCONR$^a$R$^b$, —OCSR$^a$, —OCSOR$^a$, —ONO$_2$, —OCSNR$^a$R$^b$, —SR$^a$, —S(O)R$^a$, —S(O)$_2$R$^a$, —SO$_2$NR$^a$R$^b$, —CR$^a$(=NOR$^b$), —CR$^a$(=NCOOR$^b$), —CR$^a$(=NSOR$^b$), —CR$^a$(=NSO$_2$R$^b$), —C(=NR$^a$)—NR$^b$R$^c$, —C(=NOR$^a$)—NR$^b$R$^c$, —CR$^a$(=NCN), —NCR$^a$, —P(O)R$^a$R$^b$, —P(O)OR$^a$OR$^b$, —P(O)R$^a$OR$^b$, —P(O)NR$^a$OR$^b$, —P(O)NR$^a$R$^b$, —OP(O)R$^a$R$^b$, —NHP(O)R$^a$R$^b$; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may be substituted with substituents selected from $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —NH(C=NH)NH$_2$, —NHNH$_2$, —NHCHO, —NHCHS, —NHCOOH, —NHCSOH, —OH, —SH, —SO$_3$H, —CH(=NOH), —CH(=NCN);

When E is a single bond or Nitrogen, then E and $R^6$ can be joined together to farm a saturated or unsaturated $C_{3-10}$ cycloalkyl or 3-10 membered heterocyclyl ring, which may further be fused to one or more $C_{3-10}$ cycloalkyl, 3-10 membered heterocyclyl, $C_{5-10}$ aryl or 5-10 membered heteroaryl ring. The ring thus formed may further be substituted with substituents selected from $R^{12}$;

G and $R^6$ can be joined together to form a saturated or unsaturated $C_{3-10}$ cycloalkyl or 3-10 membered heterocyclyl ring, which may further be fused to one or more $C_{3-10}$ cycloalkyl, 3-10 membered heterocyclyl, $C_{5-10}$ aryl or 5-10 membered heteroaryl ring. The ring thus formed may further be substituted with substituents selected from $R^{12}$;

$R^7$ represents —H, —OH or —OR$^9$;

$R^8$ represents —H, —CHO, —COOH, —CONH$_2$, —OH, —CH(=NOH), —COR$^a$, —COOR$^a$, —CONR$^a$R$^b$, —CR$^a$(=NOR$^b$), —OR$^a$, or —(CH$_2$)$_n$OR$^a$;

or $R^7$ and $R^8$ can be joined together to form a saturated or unsaturated ring, in which one or more methylene groups or methyne groups can be replaced with O, S, NR$^a$ or oxo; the ring thus formed may be substituted with substituents selected from $R^{12}$;

or $R^8$ and Z can be joined together to form a saturated or unsaturated ring, in which one or more methylene groups or methyne groups can be replaced with O, S, NR$^a$ or oxo; the ring thus formed may be substituted with substituents selected from $R^{12}$;

$R^9$ represents —H, $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CHO, —CONH$_2$, —COR$^a$, —CONR$^a$R$^b$, —S(O)$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$ or —P(O)NR$^a$R$^b$; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may be substituted with substituents selected from $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CHO, —CONH$_2$, —COR$^a$, —CONR$^a$R$^b$, —S(O)$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$; further wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may be substituted with substituents selected from $R^{13}$;

$R^{10}$ represents —H, $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CR$^a$(=NOR$^b$), —S(O)R$^a$, —S(O)$_2$R$^a$, —S(O)$_2$NR$^a$R$^b$, —(CH$_2$)$_n$S(O)R$^a$, —(CH$_2$)$_n$S(O)$_2$R$^a$, —P(O)R$^a$R$^b$, —COR$^a$, —CSR$^a$, —COOR$^a$, —CSOR$^a$, —COSR$^a$, —CSSR$^a$, —CONR$^a$R$^b$ or —CSNR$^a$R$^b$; wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may be substituted with substituents selected from $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —NO$_2$, NH$_2$; further wherein the said $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl and 5-10 membered heteroaryl, may be substituted with substituents selected from $R^{13}$;

$R^{11}$ represents $C_{1-12}$ alkyl, $C_{2-12}$ alkenyl, $C_{2-12}$ alkynyl, $C_{6-10}$ aryl, $C_{3-20}$ cycloalkyl, 3-14 membered heterocyclyl, 5-10 membered heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —NH(C=NH)NH$_2$, —NHNH$_2$, —NHCHO, —NHCHS, —NH-COOH, —NHCSOH, —OH, —SH, —SO$_3$H, —CH(=NOH), —CH(=NCN), —COR$^a$, —CSR$^a$, —COOR$^a$, —CSOR$^a$, —COSR$^a$, —CONR$^a$R$^b$, —CSNR$^a$R$^b$, —COCOR$^a$, —CONR$^a$NR$^b$R$^c$, —CSNR$^a$NR$^b$R$^c$, —CSNR$^a$R$^b$, —NR$^a$R$^b$, —NR$^a$SO$_2$R$^b$, —NR$^a$CONR$^b$R$^c$, —NR$^a$CSNR$^b$R$^c$, —NR$^a$(C=NR$^b$)NR$^c$R$^d$, —NR$^a$NR$^b$R$^c$, —NR$^a$COR$^b$, —NR$^a$CSR$^b$, —NR$^a$COOR$^b$, —NR$^a$CSOR$^b$, —OR$^a$, —OCOR$^a$, —OCOOR$^a$, —OCONR$^a$R$^b$, —OCSR$^a$, —OCSOR$^a$, —ONO$_2$, —OCSNR$^a$R$^b$, —SR$^a$, —S(O)R$^a$, —S(O)$_2$R$^a$, —SO$_2$NR$^a$R$^b$, —CR$^a$(=NOR$^b$), —CR$^a$(=NCOOR$^b$), —CR$^a$(=NSOR$^b$), —CR$^a$(=NSO$_2$R$^b$), —C(=NR$^a$)—NR$^b$R$^c$, —C(=NOR$^a$)—NR$^b$R$^c$, —CR$^a$(=NCN), —NCR$^a$, —P(O)R$^a$R$^b$, —P(O)OR$^a$OR$^b$, —P(O)R$^a$OR$^b$, —P(O)NR$^a$OR$^b$, —P(O)NR$^a$R$^b$, —OP(O)R$^a$R$^b$ or —NHP(O)R$^a$R$^b$; wherein the said C$_{1-12}$ alkyl, C$_{2-12}$ alkenyl, C$_{2-12}$ alkynyl, C$_{6-10}$ aryl, C$_{3-20}$ cycloalkyl, 3-14 membered heterocyclyl and 5-10 membered heteroaryl, may be substituted with substituents selected from R$^{13}$;

R$^{12}$ represents C$_{1-12}$ alkyl, C$_{2-12}$ alkenyl, C$_{2-12}$ alkynyl, C$_{6-10}$ aryl, C$_{3-20}$ cycloalkyl, 3-14 membered heterocyclyl, 5-10 membered heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —NH(C=NH)NH$_2$, —NHNH$_2$, —NHCHO, —NHCHS, —NH-COOH, —NHCSOH, —OH, —SH, —SO$_3$H, —CH(=NOH) or —CH(=NCN); wherein the said C$_{1-12}$ alkyl, C$_{2-12}$ alkenyl, C$_{2-12}$ alkynyl, C$_{6-10}$ aryl, C$_{3-20}$ cycloalkyl, 3-14 membered heterocyclyl and 5-10 membered heteroaryl, may be substituted with substituents selected from R$^{13}$;

R$^{13}$ represents C$_{1-12}$ alkyl, C$_{2-12}$ alkenyl, C$_{2-12}$ alkynyl, C$_{6-10}$ aryl, C$_{3-20}$ cycloalkyl, 3-14 membered heterocyclyl, 5-10 membered heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —NH(C=NH)NH$_2$, —NHNH$_2$, —NHCHO, —NHCHS, —NH-COOH, —NHCSOH, —OH, —SH, —SO$_3$H, —CH(=NOH) or —CH(=NCN);

R$^a$, R$^b$, R$^c$ and R$^d$ are independently selected from —H, C$_{1-12}$ alkyl, C$_{2-12}$ alkenyl, C$_{2-12}$ alkynyl, C$_{6-10}$ aryl, C$_{3-20}$ cycloalkyl, 3-14 membered heterocyclyl, 5-10 membered heteroaryl, —CN, —COCN, —N$_3$, —NO$_2$, —OCN, —NCO, —SCN, —NCS, —OCONH$_2$, —ONO$_2$, —F, —Cl, —Br, —I, —CO—, —CS—, —CHO, —CHS, —COOH, —COSH, —CONH$_2$, —CONHNH$_2$, —CSNHNH$_2$, —CSNH$_2$, —NH$_2$, —NHCONH$_2$, —NHCSNH$_2$, —NH(C=NH)NH$_2$, —NHNH$_2$, —NHCHO, —NHCHS, —NHCOOH, —NHCSOH, —OH, —SH, —SO$_3$H, —CH(=NOH), —CH(=NCN); each of which may be substituted with substituents selected from R$^{13}$;

or

R$^a$ and R$^b$ when attached to the same atom, can be joined together to form a monocyclic or polycyclic ring, in which one or more methylene groups or methyne groups can be replaced with O, S, SO, SO$_2$, NR$^a$, PR$^a$, P(=O)R$^a$ or oxo; the ring thus formed may be substituted with substituents selected from R$^{12}$;

or

R$^b$ and R$^c$ when attached to the same atom, can be joined together to form a monocyclic or polycyclic ring, in which one or more methylene groups or methyne groups can be replaced with O, S, SO, SO$_2$, NR$^a$, PR$^a$, P(=O)R$^a$ or oxo; the ring thus formed may be substituted with substituents selected from R$^{12}$;

or

R$^c$ and R$^d$ when attached to the same atom, can be joined together to form a monocyclic or polycyclic ring, in which one or more methylene groups or methyne groups can be replaced with O, S, SO, SO$_2$, NR$^a$, PR$^a$, P(=O)R$^a$ or oxo; the ring thus formed may be substituted with substituents selected from R$^{12}$;

n represents 1, 2, 3, 4 or 5; their pharmaceutically acceptable derivatives, tautomeric forms, isomers, polymorphs, prodrugs, metabolites, salts or solvates thereof.

2. The compound according to claim 1 having the Formula Ia,

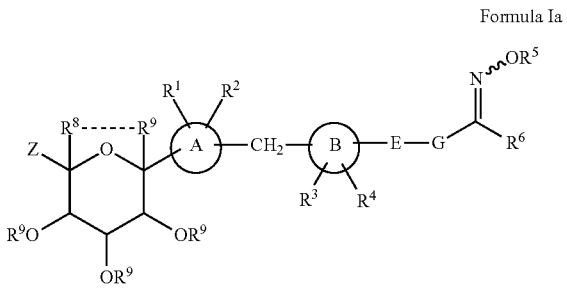

Formula Ia wherein:

Z, R$^1$, R$^2$, R$^3$, R$^4$, R$^5$, R$^6$, R$^7$, R$^8$, R$^9$, E, G, ring A and ring B are as defined in claim 1.

3. The compound according to claim 1 having the Formula Ib,

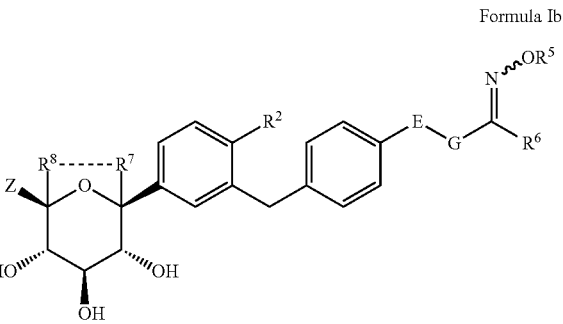

Formula Ib wherein:

Z, R$^2$, R$^5$, R$^6$, R$^7$, R$^8$, E and G are as defined in claim 1; preferably R$^2$ is Cl, F, CH$_3$, H, CN, cyclopropyl or ethynyl.

4. The compound according to claim 1, wherein Z is selected from —(CH$_2$)$_n$OR$^a$ or —OR$^a$.

5. The compound according to claim 1 having the Formula Ic,

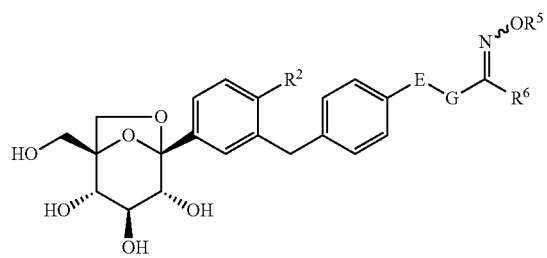

Formula Ic wherein:

R², R⁵, R⁶, E and G are as defined in claim 1.

6. The compound according to claim 1 having the Formula Id,

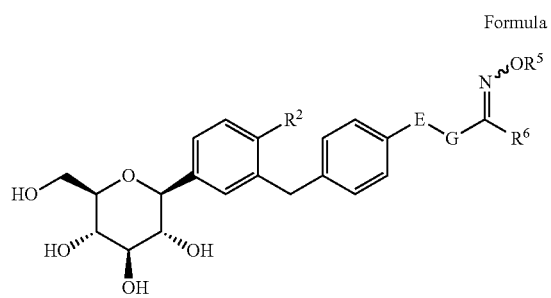

Formula Id wherein:

R², R⁵, R⁶, E and G are as defined in claim 1.

7. The compound according to claim 1 having the Formula Ie,

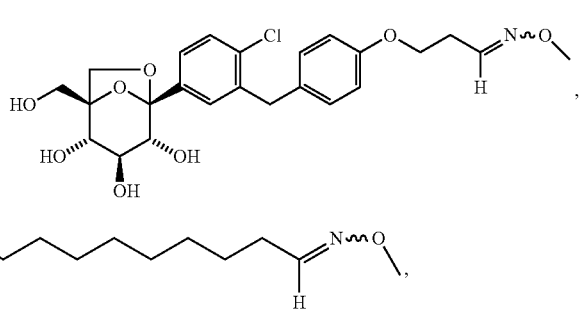

Formula Ie wherein:

R², R⁵, R⁶, E and G are as defined in claim 1.

8. The compound according to claim 1, wherein:

i) E is O or single bond;

ii) G is alkyl, alkylene, cycloalkyl or aryl;

iii) G and R⁶ can be joined together to form a saturated or unsaturated $C_{3-10}$ cycloalkyl ring;

iv) R⁵ is —H, OH or $C_{1-12}$ alkyl;

v) R⁶ is —H, $C_{1-12}$ alkyl, —NR$^a$R$^b$ or $C_{6-10}$ aryl.

9. A compound which is selected from the group consisting of:

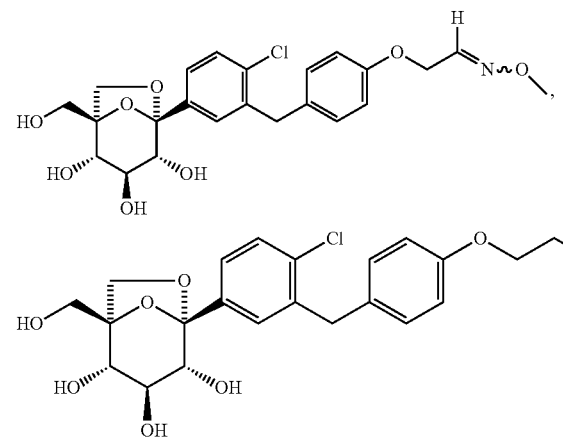

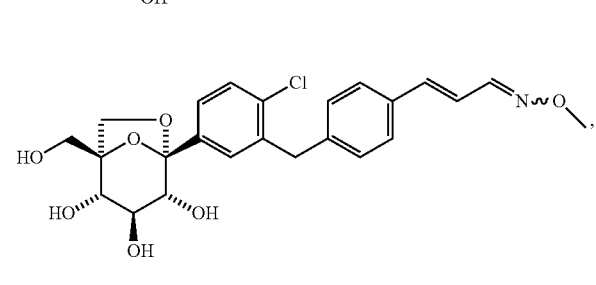

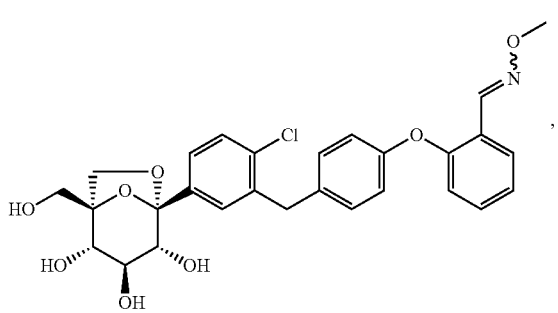

-continued
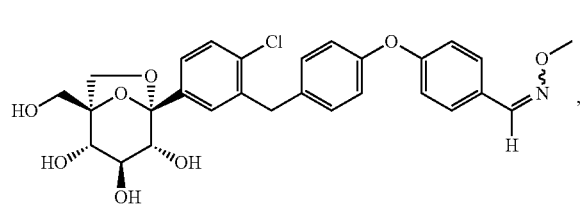
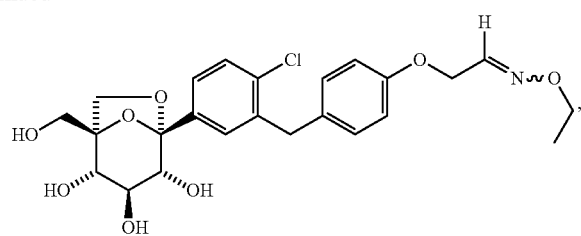
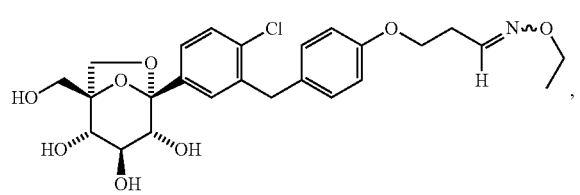
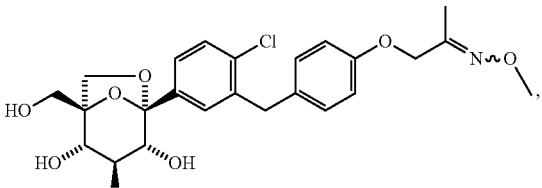
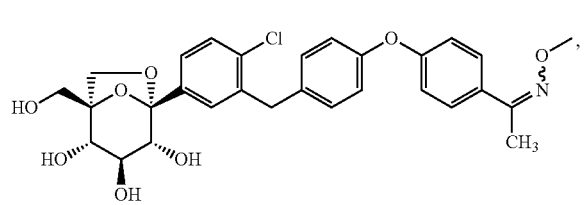
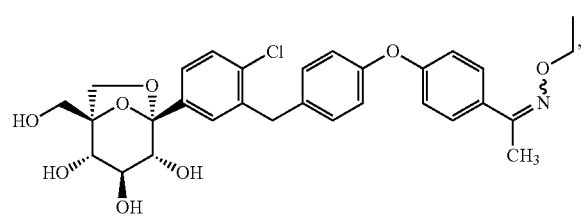
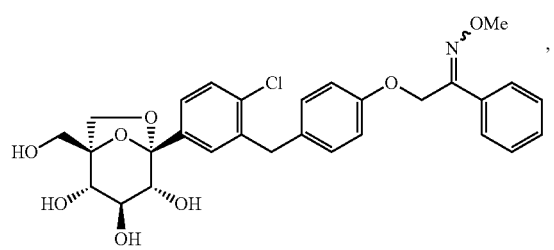
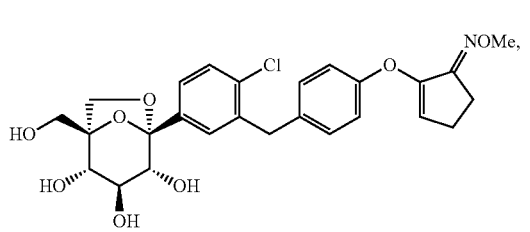
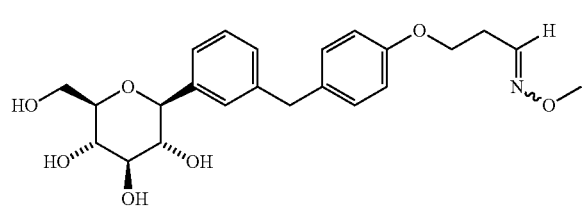
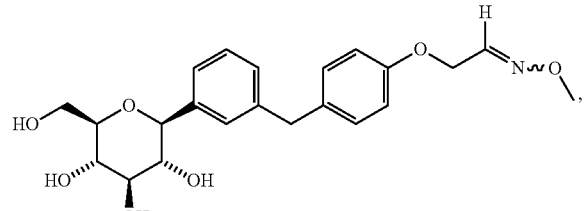
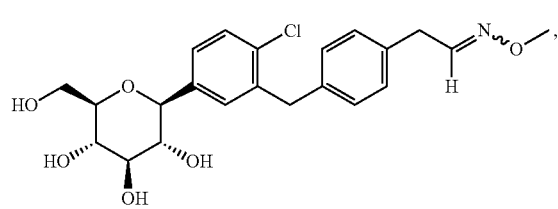
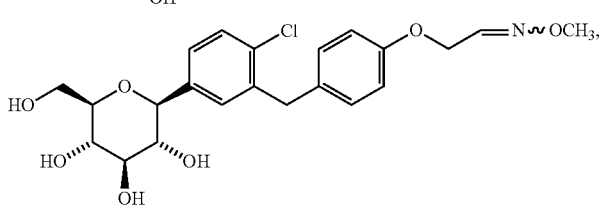
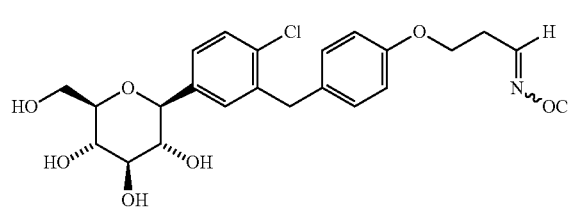
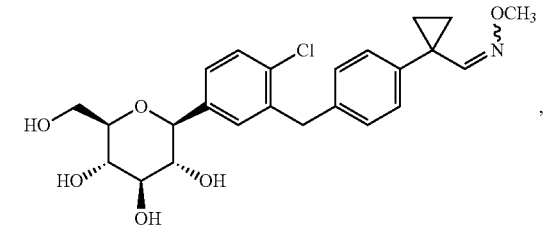

-continued
97
98
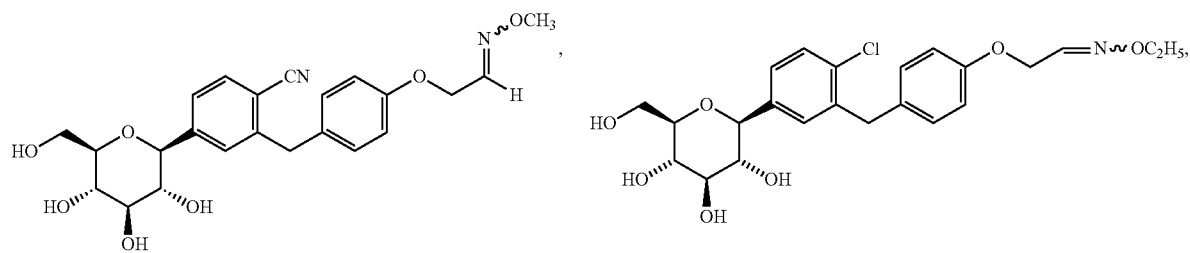
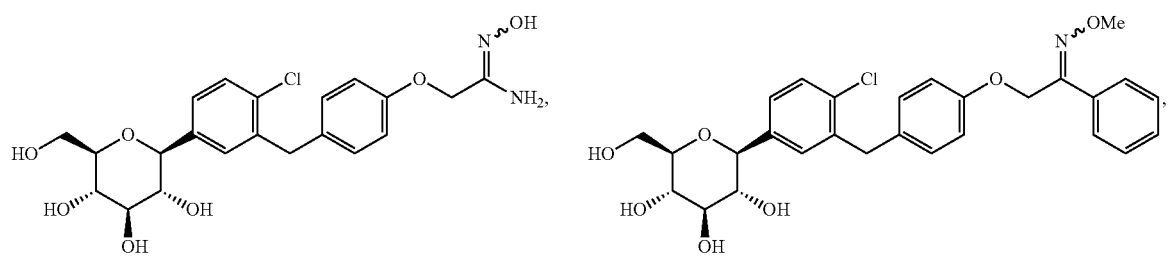
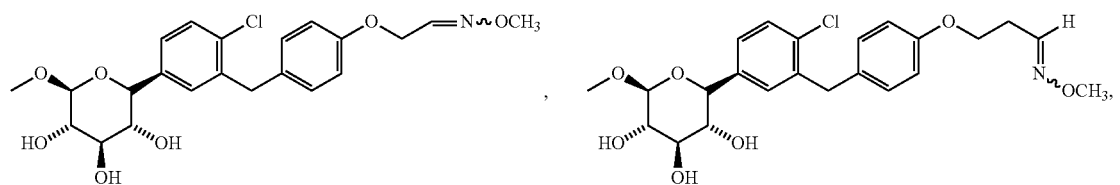
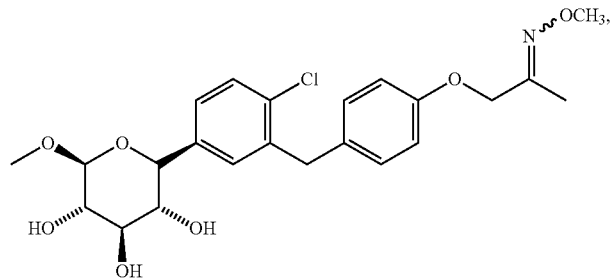

-continued

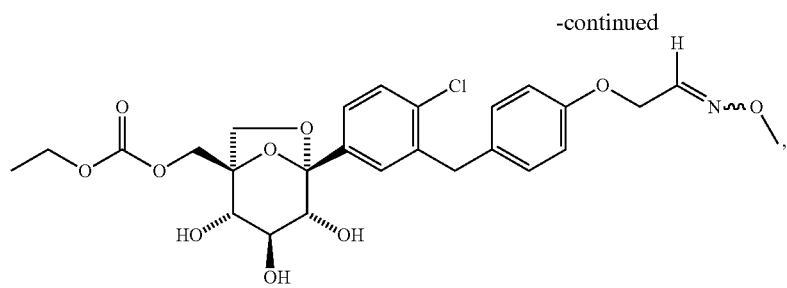

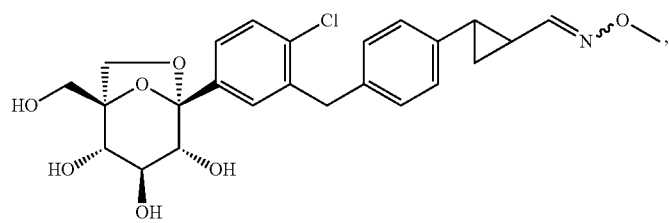

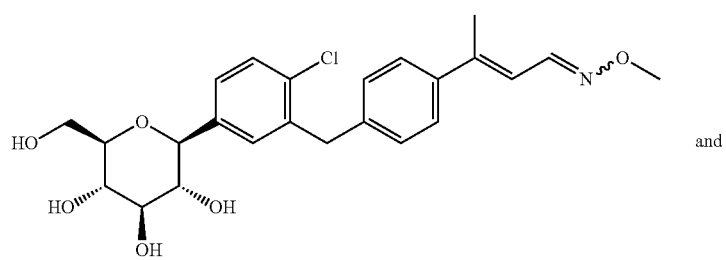

and

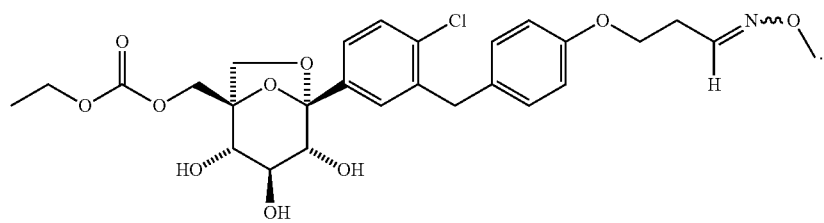

10. A process for the preparation of a compound of Formula I, according to claim 1, which comprises either of the sequences I or II:

(I) reacting compound of Formula II with compound of Formula III (R⁵ONH₂) or its salts resulting in compound of Formula I;

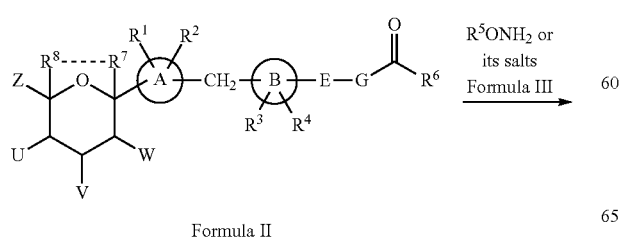

Formula II

-continued

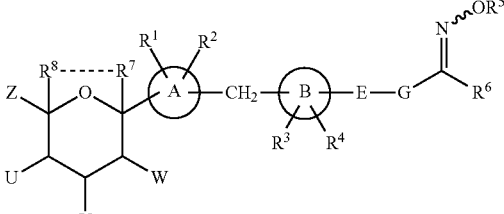

Formula I

Or (II.1) reacting compound of Formula II, with compound of Formula III (R⁵ONH₂) or its salts, to obtain compound of Formula I'
(II.2) deprotecting -OPG' of compound of Formula I', resulting in compound of Formula I;

101

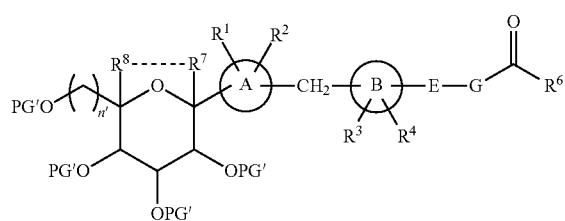

Formula II'

102

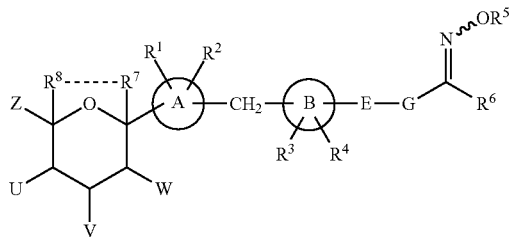

Formula I

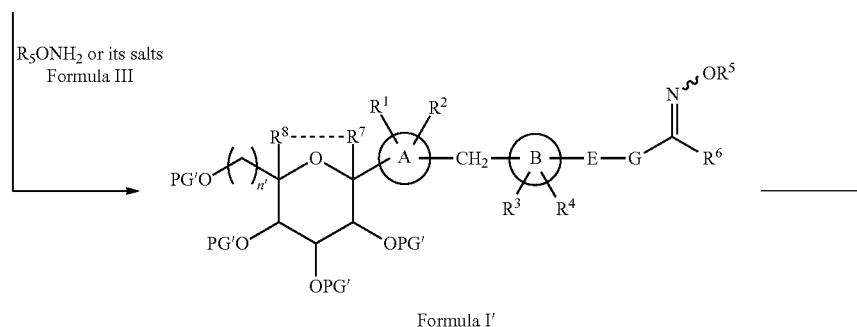

Formula I' n' = 0 or 1 wherein:
E, G, $R^1$, $R^2$, $R^3$, $R^4$, $R^5$, $R^6$, $R^7$, $R^8$, ring A and ring B are as defined in claim 1; U, V and W are OPG' and Z is —(CH$_2$)$_{n'}$—OPG'; OPG' represents protected hydroxyl groups, preferably O-acetyl, O-benzyl O-allyl, O-p-methoxybenzyl and O-silyl; n' represents 0 or 1.

11. A pharmaceutical composition, comprising a compound according to claim 1, in combination with one or more pharmaceutically acceptable carriers.

12. A method for the treatment of diabetes Type II in a subject in need thereof, which comprises administering a therapeutically effective amount of compound according to claim 1.

\* \* \* \* \*